US010131948B2

(12) United States Patent
Hare et al.

(10) Patent No.: US 10,131,948 B2
(45) Date of Patent: Nov. 20, 2018

(54) TRANSCRIPTOMIC BIOMARKERS FOR INDIVIDUAL RISK ASSESSMENT IN NEW ONSET HEART FAILURE

(71) Applicant: University of Miami, Miami, FL (US)

(72) Inventors: Joshua M. Hare, Miami Beach, FL (US); Bettina Heidecker, Miami, FL (US)

(73) Assignee: UNIVERSITY OF MIAMI, Miami, FL (US)

( * ) Notice: Subject to any disclaimer, the term of this patent is extended or adjusted under 35 U.S.C. 154(b) by 567 days.

(21) Appl. No.: 14/334,024

(22) Filed: Jul. 17, 2014

(65) Prior Publication Data

US 2014/0329710 A1   Nov. 6, 2014

Related U.S. Application Data

(63) Continuation of application No. 12/610,529, filed on Nov. 2, 2009, now abandoned, which is a continuation-in-part of application No. PCT/US2008/062281, filed on May 1, 2008.

(60) Provisional application No. 61/019,749, filed on Jan. 8, 2008, provisional application No. 60/915,224, filed on May 1, 2007, provisional application No. 60/915,215, filed on May 1, 2007.

(51) Int. Cl.
  *C12P 19/34* (2006.01)
  *C12Q 1/6883* (2018.01)
  *G01N 33/68* (2006.01)

(52) U.S. Cl.
  CPC ....... *C12Q 1/6883* (2013.01); *G01N 33/6893* (2013.01); *C12Q 2600/118* (2013.01); *C12Q 2600/136* (2013.01); *C12Q 2600/158* (2013.01); *C12Q 2600/16* (2013.01); *G01N 2800/325* (2013.01); *G01N 2800/50* (2013.01)

(58) Field of Classification Search
  CPC ............ C12Q 1/6883; C12Q 2600/118; C12Q 2600/136; C12Q 2600/158; C12Q 2600/16; G01N 2800/325; G01N 2800/50; G01N 33/6893
  USPC ...................................................... 435/91.2
  See application file for complete search history.

(56) References Cited

U.S. PATENT DOCUMENTS

| 4,016,043 A | 4/1977 | Schuurs et al. |
|---|---|---|
| 4,018,653 A | 4/1977 | Mennen |
| 4,424,279 A | 1/1984 | Bohn et al. |
| 4,683,202 A | 7/1987 | Mullis |
| 4,843,155 A | 6/1989 | Chomczynski |
| 5,030,015 A | 7/1991 | Baker et al. |
| 5,445,934 A | 8/1995 | Fodor et al. |
| 5,445,935 A | 8/1995 | Royer |
| 5,700,637 A | 12/1997 | Southern |
| 5,807,522 A | 9/1998 | Brown et al. |
| 5,854,033 A | 12/1998 | Lizardi |
| 2001/0051344 A1 | 12/2001 | Shalon et al. |
| 2003/0026793 A1 | 2/2003 | Guy |
| 2004/0132013 A1 | 7/2004 | DeBold |
| 2004/0167067 A1 | 8/2004 | Griggs et al. |
| 2005/0143628 A1 | 6/2005 | Dai et al. |
| 2005/0196764 A1 | 9/2005 | Liew |
| 2006/0094038 A1 | 5/2006 | Wagner et al. |
| 2006/0172311 A1* | 8/2006 | Cohen .................. C07K 14/705 435/6.16 |
| 2006/0246495 A1 | 11/2006 | Garrett et al. |
| 2007/0031873 A1 | 2/2007 | Wang et al. |
| 2007/0292345 A1 | 12/2007 | Khowlton et al. |
| 2008/0305512 A1 | 12/2008 | Mattingly et al. |
| 2009/0215042 A1* | 8/2009 | Sella-Tavor ........... C07K 14/47 435/6.16 |
| 2010/0112587 A1 | 5/2010 | Hare et al. |
| 2010/0152055 A1 | 6/2010 | Kozono et al. |

FOREIGN PATENT DOCUMENTS

| CA | 2553665 A1 | 2/2007 |
|---|---|---|
| EP | 1930426 A1 | 6/2008 |
| WO | WO 2001/075166 A2 | 10/2001 |
| WO | WO 2006084272 A2 | 8/2006 |
| WO | WO 2008/137586 A1 | 11/2008 |

OTHER PUBLICATIONS

Kim, Seon-Young, BMC Bioinformatics, vol. 10, No. 147, pp. 1-10, May 16, 2009.*
Davies et al., BMJ. vol. 320, pp. 428-431, Feb. (Year: 2000).*
Kittleson and Hare, Future Cardiol. 1 (6), 793-808 (Year: 2005).*
International Search Report dated Aug. 6, 2008 for corresponding application WO2008/137586A1.
European Supplemental Search Report dated Sep. 15, 2010 for corresponding application EP 08747396.
Japanese Office Action dated Apr. 2, 2013 for corresponding application JP Application No. 2010-506649.
Japanese Office Action dated Mar. 4, 2014 for corresponding application JP Application No. 2010-506649.
Archacki et al., "Expression profiling of cardiovascular disease", *Human Genomics*, (Apr. 2004) 1(5):355-370.
Archacki et al., "Identification of new genes differentially expressed in coronary artery disease by expression profiling", *Physiological Genomics*, (Sep. 2003), 15(1):65-74.
Azuaje et al., "Computational Biology for Cardiovascular Biomarker Discovery", *Briefings in Bioinformatics*, (Mar. 10, 2009) 10(4):367-377.

(Continued)

*Primary Examiner* — Cynthia B Wilder
(74) *Attorney, Agent, or Firm* — Pepper Hamilton LLP

(57) ABSTRACT

A novel transcriptomic biomarker for prognosis in heart failure has a direct clinical application in prediction of prognosis in new onset heart failure, heart disease, heart disorders and associated heart conditions. This approach should improve individualization of cardiac care and help identify patients at highest risk for circulatory collapse within the first years of presentation with heart failure.

3 Claims, 9 Drawing Sheets

(56) References Cited

OTHER PUBLICATIONS

Barth et al., "The potential for the transcriptome to serve as a clinical biomarker for cardiovascular diseases", *Circulation Research*, (2006) 98:1459-61.

Boyle et al., "Is stem cell therapy ready for patients? Stem Cell Therapy for Cardiac Repair. Ready for the Next Step", *Circulation* (2006) 114:339-352.

Chakravarti et al., "Nature, nurture and human disease", *Nature* (2003) 421:412-4.

Chen et al., "Expression of ssDNA in mammalian cells", *BioTechniques* (Jan. 2003) 34(1):167-171.

Cooper et al., "The role of endomyocardial biopsy in the management of cardiovascular disease: a scientific statement from the American Heart Association, the American College of Cardiology, and the European Society of Cardiology", *Circulation* (2007), 116:2216-2233.

Dafforn et al., "Linear mRNA amplification from as little as 5 ng total RNA for global gene expression analysis", *Biotechniques* (Nov. 2004), 37:854-857.

Deng et al., "Noninvasive discrimination of rejection in cardiac allograft recipients using gene expression profiling", *American Journal of Transplantation* (2006), 6:150-160.

Depre et al., "Unloaded heart in vivo replicates fetal gene expression of cardiac hypertrophy", *Nature Medicine* (Nov. 1998), 4:1269-1275.

Diaz et al., "Prediction of outcome in dilated cardiomyopathy", *Br Heart* (1987), 58:393-399.

Felker et al., "The problem of decompensated heart failure: nomenclature, classification, and risk stratification", *Am Heart J* (Feb. 2003), 145:S18-S25.

Felker et al., "Underlying causes and long-term survival in patients with initially unexplained cardiomyopathy", *N Engl J Med* (Apr. 2000) 342:1077-1084.

Geisler et al., "Obscurin-like 1, OBSL1, is a novel cytoskeletal protein related to obscurin", *Genomics* (Apr. 2007), 89:521-531.

Guatelli et al., "Isothermal, in vitro amplification of nucleic acids by a multienzyme reaction modeled after retroviral replication" *Proc. Natl. Acad. Sci. USA*, (Mar. 1990) 87:1874-1878.

Hajjar et al, "Prospects for gene therapy for heart failure", *Circ Res* (2000), 6:616-621.

Hall et al., "Molecular signature of recovery following combination left ventricular assist device (LVAD) support and pharmacologic therapy", *Eur Heart J* (2007);28:613-627.

Hare, "The dilated, restrictive and infiltrative cardiomyopathies", In: Zipes DP, Libby P, Bonow R, Braunwald E, editor, Braunwald's Heart Disease. 8 ed. Elsevier; 2007.

Heidbreder et al, "Hypoxia rapidly activates HIF-3alpha mRNA expression", *FASEB J* (Jun. 2003), 17:1541-1543.

Heidecker et al., "The use of transcriptomic biomarkers for personalized medicine", *Heart Fail Rev* (Mar. 2007), 12:1-11.

Heidecker et al., "Transcriptomic Biomarkers for Individual Risk Assessment in New-Onset Heart Failure", *Circulation* (Jun. 30, 2008), 118(3):238-246.

Ito et al., "A novel WD40 repeat protein, WDC146, highly expressed during spermatogenesis in a stage-specific manner", *Biochem Biophys Res Commun* (2001) ;280:656-663.

Kittleson et al., "Gene expression analysis of ischemic and nonischemic cardiomyopathy: Shared and distinct genes in the development of heart failure", *Physiological Genomics*, (Mar. 2005) 12(3):299-307.

Kittleson et al., "Gene expression in giant cell myocarditis: Altered expression of immune response genes", *International Journal of Cardiology*, (2005), 102(2):333-340.

Kittleson et al., "Identification of a gene expression profile that differentiates between ischemic and nonischemic cardiomyopathy", *Circulation* (2004), 110(22):3444-3451.

Kittleson et al., "Increased levels of uric acid predict haemodynamic compromise in patients with heart failure independently of B-type natriuretic peptide levels", *Heart* (2007),93:365-367.

Kroese et al., "Genetic tests and their evaluation: Can we answer the key questions?", *Genetics in Medicine* (Nov./Dec. 2004) 6(6):475-480.

Kwoh et al., "Transcription-based amplification system and detection of amplified human immunodeficiency virus type 1 with a bead-based sandwich hybridization format", *Proc. Natl. Acad. Sci. USA*, (Feb. 1989) 86:1173-1177.

Liew et al., "The peripheral blood transcriptome dynamically reflects system wide biology: a potential diagnostic tool", *J Lab Clin Med* (2006), 147:126-132.

Lowes et al., "Serial Gene Expression Profiling in the Intact Human Heart", *J. Heart Lung Transplant*, (May 2006), 25(5):579-588.

Lowes et al., "Myocardial gene expression in dilated cardiomyopathy treated with beta-blocking agents", *N Engl J Med* (May 2002), 346(18):1357-1365.

Lucentini, "Gene Association Studies Typically Wrong", *The Scientist*, (Dec. 20, 2004), 18(24):20.

Luo et al., "Disruption of mRad50 causes embryonic stem cell lethality, abnormal embryonic development, and sensitivity to ionizing radiation", *Proc Natl Acad Sci USA* (Jun. 1999), 96:7376-7381.

Maisel, "B-type natriuretic peptide levels: diagnostic and prognostic in congestive heart failure: what's next?", *Circulation* (2002), 105:2328-2331.

Margulies et al., "Mixed messages: transcription patterns in failing and recovering human myocardium", *Circ Res* (Feb. 2005), 96:592-599.

Mazhari et al., "Advances in cell-based therapy for structural heart disease", *Prog Cardiovasc Dis* (May/Jun. 2007), 49:387-395.

Moore et al., "Stem cells and their niches", *Science* (Mar. 2006), 311:1880-1885.

Morgun et al., "Molecular profiling improves diagnoses of rejection and infection in transplanted organs", *Circ Res* (May 2006), 98:e74-e83.

Mukherjee et al., "Estimating dataset size requirements for classifying DNA microarray data", *Journal of Computational Biology* (Nov. 2003), 10:119-142.

Negishi et al., "Identification and cDNA cloning of single- stranded DNA binding proteins that interact with the region upstream of the human c- myc gene", *Oncogene* (1994), 9:1133-1143.

Ota et al., "Complete sequencing and characterization of 21,243 full-length human cDNAs", *Nature Genetics* (Jan. 2004), 36:40-45.

Perou et al., "Molecular portraits of human breast tumours", *Nature* (Aug. 2000), 406:747-752.

Raeker et al., "Obscurin is required for the lateral alignment of striated myofibrils in Zebrafish", *Developmental Dynamics* (2006), 235:2018-2029.

Semenza, "Pulmonary vascular responses to chronic hypoxia mediated by hypoxia-inducible factor 1", *Proc Am Thorac Soc* (2005), 2:68-70.

Sharma et al., "DNA microarray analysis for human congenital heart disease", *Cell Biochemistry and Biophysics* (2006), 44(1):1-9.

Singh et al., "Microarray-based comparison of three amplification methods for nanogram amounts of total RNA", *Am J Physiol Cell Physiol* (2005), 288:C1179-C1189.

Stec et al., Comparison of the Predictive Accuracy of DNA Array-Based Multigene Classifiers across cDNA Arrays and Affymetrix GeneChips, *J Mol Diagn.* (Aug. 2005), 7(3):357-67.

Steenman et al., "Transcriptomal analysis of failing and nonfailing human hearts", *Physiol Genomics* (2003), 12:97-112.

Storey, "A direct approach to false discovery rates", *Journal of the Royal Statistical Society* (2002), 64:479-498.

Tang et al., "Microarray Analysis Reveals the Role of Matrix Metalloproteinases in Mouse Experimental Autoimmune Myocarditis Induced by Cardiac Myosin Peptides", *Cellular & Molecular Biology Letters*, (Apr. 2007), 12(2):176-191.

Thomas, "Hybridization of denatured RNA and small DNA fragments transferred to nitrocellulose", *Proc. Natl. Acad. Sci. USA* (Sep. 1980), 77:5201-5205.

Tibshirani et al., "Diagnosis of multiple cancer types by shrunken centroids of gene expression", *Proc Natl Acad Sci USA* (May 2002), 99(10):6567-6572.

(56) References Cited

OTHER PUBLICATIONS

Tusher et al., "Significance analysis of microarrays applied to the ionizing radiation response", *Proc Natl Acad Sci USA* (Apr. 2001), 98(9):5116-121.

van Haaften et al., "Biologically relevant effects of mRNA amplification on gene expression profiles", *BMC Bioinformatics* (2006), 7:200.

Watanabe et al., "Gene Expression Profiles of Cardiomyocytes in Rat Autoimmune Myocarditis by DNA Microarray and Increase of Regenerating Gene Family", *Translational Research* (Sep. 2008), 152(3):119-127.

Boyle et al., "Is stem cell therapy ready for patients? Stem Cell Therapy for Cardia Repair. Ready for the Next Step." Circulation (2006) 114:339-352.

Cheung et al., "Making and Reading Microarrays," Nature Genetics Suppl. (Jan. 1999) 21:15-19.

Database Gene Expression Omnibus, *NCBI* (2003), Affymetrix Human Genome U133 Plus 2.0 Array.

Franz et al., "Serum troponin T: diagnostic marker for acute myocarditis," *Clin. Chem.* (1996), 42(2):340-341.

Grzeskowiak et al., "Expression profiling of human idiopathic dilated cardiomyopathy," *Cardiovascular Res.* (2003), 59:400-411.

Harper, "Can sensitivity and specificity estimates from research studies be made more meaningful for clinincal practice?" Opthal. Physiol. Opt. (2002), 22:271-273.

Heidecker et al., "Transcriptomic Biomarkers for the Accurate Diagnosis of Myocarditis," *Circ.* (2011), 123(11):1174-1184.

Huang et al., "A comparative study of discriminating human heart failure etiology using gene expression profiles," *BMC Bioinform.* (Aug. 24, 2005), Biomed Central, London, 6(205):1-15.

International Search Report dated Sep. 21, 2010 for corresponding application PCT/US2010/037018.

International Search Report dated Jul. 30, 2008 for corresponding application PCT/US2008/062290.

Lockart, *Nature Biotech.*(1996)14: 1675-1680.

McManus et al., "Genetic Determinants of Coxsackievirus B3 Pathogenesis" *Ann. N.Y. Acad. Sci.* (2002), 975:169-179.

Nanni et al., "Differential gene expression profiling in genetic and multifactorial cardiovascular diseases," *J. Mol. Cell. Cardio.* (2006), 41(6):934-948.

Rudy et al., "Differential function of CD80- and CD86-transfected human melanoma cells in the presence of IL-12 and IFN-gamma," *Int. Immunol.* (1997), 9(6):853-860.

Written Opinion of the International Searching Authority dated Jul. 30, 2008 for corresponding International Application No. PCT/US2008/062290.

Yanagawa et al., "Affymetrix Oligonucleotide Analysis of Gene Expression in the Injured Heart,"*Methods in Mol. Med.* (2005), 112:305-320.

* cited by examiner

TRANSCRIPTOMIC BIOMARKERS FOR INDIVIDUAL RISK ASSESSMENT IN NEW ONSET HEART FAILURE

CROSS-REFERENCE TO RELATED APPLICATIONS

The present application is a continuation of U.S. patent application Ser. No. 12/610,529, filed Nov. 2, 2009, which is a continuation in part of International Application No. PCT/US2008/62281, international filing date May 1, 2008, which in turn claims priority to U.S. Provisional Application No. 61/019,749, filed Jan. 8, 2018 Jan. 8, 2008, U.S. provisional patent application No. 60/915,224, filed May 1, 2007, and U.S. Provision Patent Application No. 60/915, 215, filed May 1, 2007, each of which are incorporated herein by reference in their entirety.

STATEMENT REGARDING FEDERALLY SPONSORED RESEARCH

This invention was made with U.S. government support under grant numbers M400-217-2954 and RO-1 HL-65455 both awarded by the National Institutes of Health. The U.S. government may have certain rights in the invention.

FIELD OF THE INVENTION

This invention relates to biomarkers of heart disease novel drug therapeutic targets, compositions and methods of predicting, diagnosing and treating heart diseases and related disorders thereof. More specifically, the invention concerns methods and compositions based on unique molecular signatures associated with various aspects of cardiac diseases and disorders.

BACKGROUND

The clinical course of patients with newly diagnosed heart failure varies drastically, with some patients recovering and returning to completely normal levels of ejection fraction (EF), while others develop severe symptoms of cardiac decompensation that require insertion of a left ventricular assist device (LVAD) or a cardiac transplant. Accurate risk assessment and prediction of prognosis at first presentation are crucial for appropriate allocation of therapy monitoring and patient management. Prediction tools based on standard criteria have had limited accuracy.

SUMMARY

This Summary is provided to present a summary of the invention to briefly indicate the nature and substance of the invention. It is submitted with the understanding that it will not be used to interpret or limit the scope or meaning of the claims.

Identifying patients early on in a disease or identifying those at risk of developing cardiovascular diseases and related disorders, would provide both the individual patients and governments with substantial financial savings. There is thus a need for accurate prognostic assessment allowing for the adjustment of treatment appropriately and early enough.

Transcriptomic biomarkers comprise biomolecules and allow for the prediction in the prognostic outcome of heart diseases and disorders thereof. Methods for the prognosis and identification of novel drug targets are provided.

The transcriptomic biomarkers, methods and assays disclosed herein are directed to the examination of expression of transcriptomic biomarkers in a mammalian biological sample, e.g. tissue or cell sample, wherein the determination of that expression of one or more such transcriptomic biomarkers is predictive of prognostic outcome or diagnostic of cardiac and cardiovascular diseases and disorders, such as for example, myocarditis, Coronary Heart Disease, angina, Acute Coronary Syndrome, Aortic Aneurysm and Dissection, arrhythmias, Cardiomyopathy, Congenital Heart Disease, congestive heart failure or chronic heart failure, pericarditis, and the like.

In a preferred embodiment a molecular composition comprises gene or nucleic acid sequences: 232669_at (Hypoxia inducible factor 3, alpha subunit), 214951_at (solute carrier family 26, member 10), 243482_at (Epidermal growth factor receptor pathway substrate 15-like 1), 226210_s_at (maternally expressed 3), 232159_at (Epidermal growth factor receptor pathway substrate 15-like 1), 233026_s_at (PDZ domain containing), 211996_s_at (KIAA0220-like protein hypothetical gene LOC 283846), 243774_at (mucin 20, cell surface associated), 242551_at (Chromosome 18 open reading frame), 244548_at (Rho GTPase activating protein 26), 244208_at (Checkpoint suppressor 1), 239984_at (Sodium channel, voltage-gated, type VII, alpha), 230683_at (CDNA:FLJ20892 fis, clone ADKA03430), 214869_at (apolipoprotein L, 6), 241597_at (Arginine-glutamic acid dipeptide (RE) repeats), 235887_at (Smg-6 homolog, nonsense mediated mRNA decay factor (*C. elegans*)), 229957_at (transmembrane protein 91), 223546_x_at (LUC7L-like (*S. cerevisiae*)), 239567_at (Rho GTPase activating protein 10), 242194_at (Cullin 4A), 1558525_at (hypothetical protein LOC283901), 227178_at (CUG triplet repeat, RNA binding protein 2), 228198_s_at (Mitochondrial ribosomal protein S9), 202379_s_at (natural killer-tumor recognition sequence), 224260_at (CDNA clone), 238643_at (Neuroblastoma, suppression of tumorigenicity 1), 232253_at (RAD50 homolog (*S. cerevisiae*)), 227968_at (Parkinson disease 7 domain containing 1), 233197_at (kelch-like 9 (*Drosophila*)), 244512_at (transcribed locus strongly similar to XP 0010813421), 233443_at (hypothetical protein LOC389362), 231275_at (FLJ42875 protein), 226419_s_at (hypothetical protein LOC64546), 201221_s_at small nuclear ribonucleoprotein 70 kDa polypeptide), 209354_at (tumor necrosis factor receptor family member 14), 226571_s_at (protein tyrosine phosphatase receptor type, S), 220728_at (EST), 203071_at (sema domain, immunoglobulin domain (Ig), short basic domain), 213946_s_at obscurin-like 1, similar to titin isoform N2-B), 201394_s_at (RNA binding motif protein 5), 203748_x_at (RNA binding motif, single stranded interacting protein 1), 223147_s_at (WD repeat domain 33), 213773_x_at (NOL/NOP2/Sun domain family, member 5), 1560049_at CUG triplet repeat, RNA binding protein 2), 243974_at (CDNA clone IMAGE:4821815), 201510_at E74-like factor 3 (ets domain transcription factor, epithelial specific complementary sequences, fragments, alleles, variants and/or gene products thereof.

In another preferred embodiment, the detection in a cell or patient of the biomolecules, complementary sequences, fragments, alleles, variants, derivatives and/or gene products thereof, is prognostic of a good clinical prognosis in heart failure, biomarkers is predictive of prognostic outcome or diagnostic of cardiac and cardiovascular diseases and disorders, such as for example, myocarditis, Coronary Heart Disease, angina, Acute Coronary Syndrome, Aortic Aneurysm and Dissection, arrhythmias, Cardiomyopathy, Congenital Heart Disease, congestive heart failure or chronic heart failure, pericarditis, and the like.

In another preferred embodiment, the biomolecules, complementary sequences, fragments, alleles, variants, derivatives and/or gene products thereof, are modulated or over-expressed at levels by at least 1% to a 100% or more in a cell or patient as compared to levels in a normal cell or normal subject.

In another preferred embodiment, the biomolecules, complementary sequences, fragments, alleles, variants, derivatives and/or gene products thereof, are modulated or over expressed by about 50% in a cell or a patient as compared to levels in a control, normal cell or normal subject.

In another preferred embodiment, the biomolecules, complementary sequences, fragments, alleles, variants, derivatives and/or gene products thereof, are modulated or over expressed by about 75% in a cell or a patient as compared to levels in a control, normal cell or normal subject.

In another preferred embodiment, at least ten biomolecules are prognostic in individual risk assessment in a patient for onset of heart failure, cardiac and cardiovascular diseases and disorders, such as for example, myocarditis, Coronary Heart Disease, angina, Acute Coronary Syndrome, Aortic Aneurysm and Dissection, arrhythmias, Cardiomyopathy, Congenital Heart Disease, congestive heart failure or chronic heart failure, pericarditis, and the like.

In another preferred embodiment, a plurality of biomolecules are prognostic in individual risk assessment in a patient for onset of heart failure and predictive of prognostic outcome or diagnostic of cardiac and cardiovascular diseases and disorders, such as for example, myocarditis, Coronary Heart Disease, angina, Acute Coronary Syndrome, Aortic Aneurysm and Dissection, arrhythmias, Cardiomyopathy, Congenital Heart Disease, congestive heart failure or chronic heart failure, pericarditis, and the like.

In another preferred embodiment, a biomarker (TBB) for predicting a prognosis of heart failure, comprising nucleic acid sequences/biomolecules comprising: 232669_at (Hypoxia inducible factor 3, alpha subunit), 214951_at (solute carrier family 26, member 10), 243482_at (Epidermal growth factor receptor pathway substrate 15-like 1), 226210_s_at (maternally expressed 3), 232159_at (Epidermal growth factor receptor pathway substrate 15-like 1), 233026_s_at (PDZ domain containing), 211996_s_at (KIAA0220-like protein hypothetical gene LOC 283846), 243774_at (mucin 20, cell surface associated), 242551_at (Chromosome 18 open reading frame), 244548_at (Rho GTPase activating protein 26), 244208_at (Checkpoint suppressor 1), 239984_at (Sodium channel, voltage-gated, type VII, alpha), 230683_at (CDNA:FLJ20892 fis, clone ADKA03430), 214869_at (apolipoprotein L, 6), 241597_at (Arginine-glutamic acid dipeptide (RE) repeats), 235887_at (Smg-6 homolog, nonsense mediated mRNA decay factor (*C. elegans*)), 229957_at (transmembrane protein 91), 223546_x_at (LUC7L-like (*S. cerevisiae*)), 239567_at (Rho GTPase activating protein 10), 242194_at (Cullin 4A), 1558525_at (hypothetical protein LOC283901), 227178_at (CUG triplet repeat, RNA binding protein 2), 228198_s_at (Mitochondrial ribosomal protein S9), 202379_s_at (natural killer-tumor recognition sequence), 224260_at (CDNA clone), 238643_at (Neuroblastoma, suppression of tumorigenicity 1), 232253_at (RAD50 homolog (*S. cerevisiae*)), 227968_at (Parkinson disease 7 domain containing 1), 233197_at (kelch-like 9 (*Drosophila*)), 244512_at (transcribed locus strongly similar to XP 0010813421), 233443_at (hypothetical protein LOC389362), 231275_at (FLJ42875 protein), 226419_s_at (hypothetical protein LOC64546), 201221_s_at small nuclear ribonucleoprotein 70 kDa polypeptide), 209354_at (tumor necrosis factor receptor family member 14), 226571_s_at (protein tyrosine phosphatase receptor type, S), 220728_at (EST), 203071_at (sema domain, immunoglobulin domain (Ig), short basic domain), 213946_s_at obscurin-like 1, similar to titin isoform N2-B), 201394_s_at (RNA binding motif protein 5), 203748_x_at (RNA binding motif, single stranded interacting protein 1), 223147_s_at (WD repeat domain 33), 213773_x_at (NOL/NOP2/Sun domain family, member 5), 1560049_at CUG triplet repeat, RNA binding protein 2), 243974_at (CDNA clone IMAGE:4821815), 201510_at E74-like factor 3 (ets domain transcription factor, epithelial specific), complementary sequences, fragments, alleles, derivatives, variants and/or gene products thereof.

In another preferred embodiment, the biomolecules of the biomarker comprising biomolecules, complementary sequences, fragments, alleles, derivatives, variants and gene products thereof, are modulated and/or over-expressed at levels by at least 1% to a 100% or more in a cell or patient as compared to levels in a normal cell or normal subject.

In another preferred embodiment, the biomolecules of the biomarker comprising biomolecules, complementary sequences, fragments, alleles, derivatives, variants and gene products thereof, comprise a molecular signature wherein the biomolecules are modulated with respect to each other and normal controls are prognostic of increased risk of disease or the outcome of a disease. Thus, one or more biomolecules which comprise a molecular signature or expression profile for a specific disease may be up-regulated or down-regulated in relation to each other.

In another preferred embodiment, the nucleic acid sequences, complementary sequences, fragments, alleles, variants, derivatives and/or gene products thereof, are modulated and/or over-expressed by about 50% in a cell or a patient as compared to levels in a normal cell or normal subject.

In another preferred embodiment, the nucleic acid sequences, complementary sequences, fragments, alleles, variants, derivatives and/or gene products thereof, are modulated and/or over-expressed by about 75% in a cell or a patient as compared to levels in a normal cell or normal subject.

In another preferred embodiment, an antibody or aptamer specific for each gene sequence comprising: 232669_at (Hypoxia inducible factor 3, alpha subunit), 214951_at (solute carrier family 26, member 10), 243482_at (Epidermal growth factor receptor pathway substrate 15-like 1), 226210_s_at (maternally expressed 3), 232159_at (Epidermal growth factor receptor pathway substrate 15-like 1), 233026_s_at (PDZ domain containing), 211996_s_at (KIAA0220-like protein hypothetical gene LOC 283846), 243774_at (mucin 20, cell surface associated), 242551_at (Chromosome 18 open reading frame), 244548_at (Rho GTPase activating protein 26), 244208_at (Checkpoint suppressor 1), 239984_at (Sodium channel, voltage-gated, type VII, alpha), 230683_at (CDNA:FLJ20892 fis, clone ADKA03430), 214869_at (apolipoprotein L, 6), 241597_at (Arginine-glutamic acid dipeptide (RE) repeats), 235887_at (Smg-6 homolog, nonsense mediated mRNA decay factor (*C. elegans*)), 229957_at (transmembrane protein 91), 223546_x_at (LUC7L-like (*S. cerevisiae*)), 239567_at (Rho GTPase activating protein 10), 242194_at (Cullin 4A), 1558525_at (hypothetical protein LOC283901), 227178_at (CUG triplet repeat, RNA binding protein 2), 228198_s_at (Mitochondrial ribosomal protein S9), 202379_s_at (natural killer-tumor recognition sequence), 224260_at (CDNA clone), 238643_at (Neuroblastoma, suppression of tumorigenicity 1), 232253_at (RAD50 homolog (*S. cerevisiae*)), 227968_at (Parkinson disease 7 domain containing 1), 233197_at (kelch-like 9 (*Drosophila*)), 244512_at (transcribed locus strongly similar to XP 0010813421), 233443_at (hypothetical protein LOC389362), 231275_at (FLJ42875 protein), 226419_s_at (hypothetical protein LOC64546), 201221_s_at small nuclear ribonucleoprotein 70 kDa polypeptide), 209354_at (tumor necrosis factor receptor family member 14), 226571_s_at (protein tyrosine phosphatase receptor type, S), 220728_at (EST), 203071_at (sema domain, immunoglobulin domain (Ig), short basic domain), 213946_s_at obscurin-like 1, similar to titin isoform N2-B), 201394_s_at (RNA binding motif protein 5), 203748_x_at (RNA binding motif, single stranded interacting protein 1), 223147_s_at (WD repeat domain 33), 213773_x_at (NOL/NOP2/Sun domain family, member 5), 1560049_at CUG triplet repeat, RNA binding protein 2), 243974_at (CDNA clone IMAGE:4821815), 201510_at E74-like factor 3 (ets domain transcription factor, epithelial specific), complementary sequences, fragments, alleles, derivatives, variants and/or gene products thereof.

In another preferred embodiment, a biochip comprises nucleic acid sequences: 232669_at (Hypoxia inducible factor 3, alpha subunit), 214951_at (solute carrier family 26, member 10), 243482_at (Epidermal growth factor receptor pathway substrate 15-like 1), 226210_s_at (maternally expressed 3), 232159_at (Epidermal growth factor receptor pathway substrate 15-like 1), 233026_s_at (PDZ domain containing), 211996_s_at (KIAA0220-like protein hypothetical gene LOC 283846), 243774_at (mucin 20, cell surface associated), 242551_at (Chromosome 18 open reading frame), 244548_at (Rho GTPase activating protein 26), 244208_at (Checkpoint suppressor 1), 239984_at (Sodium channel, voltage-gated, type VII, alpha), 230683_at (CDNA:FLJ20892 fis, clone ADKA03430), 214869_at (apolipoprotein L, 6), 241597_at (Arginine-glutamic acid dipeptide (RE) repeats), 235887_at (Smg-6 homolog, nonsense mediated mRNA decay factor (*C. elegans*)), 229957_at (transmembrane protein 91), 223546_x_at (LUC7L-like (*S. cerevisiae*)), 239567_at (Rho GTPase activating protein 10), 242194_at (Cullin 4A), 1558525_at (hypothetical protein LOC283901), 227178_at (CUG triplet repeat, RNA binding protein 2), 228198_s_at (Mitochondrial ribosomal protein S9), 202379_s_at (natural killer-tumor recognition sequence), 224260_at (CDNA clone), 238643_at (Neuroblastoma, suppression of tumorigenicity 1), 232253_at (RAD50 homolog (*S. cerevisiae*)), 227968_at (Parkinson disease 7 domain containing 1), 233197_at (kelch-like 9 (*Drosophila*)), 244512_at (transcribed locus strongly similar to XP 0010813421), 233443_at (hypothetical protein LOC389362), 231275_at (FLJ42875 protein), 226419_s_at (hypothetical protein LOC64546), 201221_s_at small nuclear ribonucleoprotein 70 kDa polypeptide), 209354_at (tumor necrosis factor receptor family member 14), 226571_s_at (protein tyrosine phosphatase receptor type, S), 220728_at (EST), 203071_at (sema domain, immunoglobulin domain (Ig), short basic domain), 213946_s_at obscurin-like 1, similar to titin isoform N2-B), 201394_s_at (RNA binding motif protein 5), 203748_x_at (RNA binding motif, single stranded interacting protein 1), 223147_s_at (WD repeat domain 33), 213773_x_at (NOL/NOP2/Sun domain family, member 5), 1560049_at CUG triplet repeat, RNA binding protein 2), 243974_at (CDNA clone IMAGE:4821815), 201510_at E74-like factor 3 (ets domain transcription factor, epithelial specific), complementary sequences, fragments, alleles, derivatives, variants and/or gene products thereof.

In one embodiment, the biochip comprises at least ten nucleic acid sequences, complementary sequences, fragments, alleles, variants, derivatives and/or gene products thereof.

In a preferred embodiment, a method of assessing identifying and distinguishing between patients at a high risk of heart disease and patients with a good prognosis for recovery comprising: identifying in a biological sample from a patient a molecular signature comprising a transcriptomic based biomarker (TBB): 232669_at (Hypoxia inducible factor 3, alpha subunit), 214951_at (solute carrier family 26, member 10), 243482_at (Epidermal growth factor receptor pathway substrate 15-like 1), 226210_s_at (maternally expressed 3), 232159_at (Epidermal growth factor receptor pathway substrate 15-like 1), 233026_s_at (PDZ domain containing), 211996_s_at (KIAA0220-like protein hypothetical gene LOC 283846), 243774_at (mucin 20, cell surface associated), 242551_at (Chromosome 18 open reading frame), 244548_at (Rho GTPase activating protein 26), 244208_at (Checkpoint suppressor 1), 239984_at (Sodium channel, voltage-gated, type VII, alpha), 230683_at (CDNA:FLJ20892 fis, clone ADKA03430), 214869_at (apolipoprotein L, 6), 241597_at (Arginine-glutamic acid dipeptide (RE) repeats), 235887_at (Smg-6 homolog, nonsense mediated mRNA decay factor (*C. elegans*)), 229957_at (transmembrane protein 91), 223546_x_at (LUC7L-like (*S. cerevisiae*)), 239567_at (Rho GTPase activating protein 10), 242194_at (Cullin 4A), 1558525_at (hypothetical protein LOC283901), 227178_at (CUG triplet repeat, RNA binding protein 2), 228198_s_at (Mitochondrial ribosomal protein S9), 202379_s_at (natural killer-tumor recognition sequence), 224260_at (CDNA clone), 238643_at (Neuroblastoma, suppression of tumorigenicity 1), 232253_at (RAD50 homolog (*S. cerevisiae*)), 227968_at (Parkinson disease 7 domain containing 1), 233197_at (kelch-like 9 (*Drosophila*)), 244512_at (transcribed locus strongly similar to XP_0010813421), 233443_at (hypothetical protein LOC389362), 231275_at (FLJ42875 protein), 226419_s_at (hypothetical protein LOC64546), 201221_s_at small nuclear ribonucleoprotein 70 kDa polypeptide), 209354_at (tumor necrosis factor receptor family member 14), 226571_s_at (protein tyrosine phosphatase receptor type, S), 220728_at (EST), 203071_at (sema domain, immunoglobulin domain (Ig), short basic domain), 213946_s_at obscurin-like 1, similar to titin isoform N2-B), 201394_s_at (RNA binding motif protein 5), 203748_x_at (RNA binding motif, single stranded interacting protein 1), 223147_s_at (WD repeat domain 33), 213773_x_at (NOL/NOP2/Sun domain family, member 5), 1560049_at CUG triplet repeat, RNA binding protein 2), 243974_at (CDNA clone IMAGE:4821815), 201510_at E74-like factor 3 (ets domain transcription factor, epithelial specific), complementary sequences, fragments, alleles, derivatives, variants and/or gene products thereof; assessing the probability of identification of each component gene in each sample; assigning each to a class; and, differentiating between idiopathic cardiomyopathy and myocarditis.

In another preferred embodiment, the transcriptomic biomarker comprises an expression profile or molecular signature of the biomolecules. For example, the expression profile of each biomolecule with respect to each other and/or to controls is prognostic or diagnostic of a disease. For example, in some aspects, some of the biomolecules are up-regulated, down-regulated or not expressed relative to each other. This is a molecular signature which would be diagnostic or prognostic, risk assessment etc of a specific disease.

In a preferred embodiment, a method of assessing identifying and distinguishing between patients at a high risk of heart disease and patients with a good prognosis for recovery comprising: identifying in a biological sample from a patient a molecular signature comprising a transcriptomic based biomarker (TBB): 232669_at (Hypoxia inducible factor 3, alpha subunit), 214951_at (solute carrier family 26, member 10), 243482_at (Epidermal growth factor receptor pathway substrate 15-like 1), 226210_s_at (maternally expressed 3), 232159_at (Epidermal growth factor receptor pathway substrate 15-like 1), 233026_s_at (PDZ domain containing), 211996_s_at (KIAA0220-like protein hypothetical gene LOC 283846), 243774_at (mucin 20, cell surface associated), 242551_at (Chromosome 18 open reading frame), 244548_at (Rho GTPase activating protein 26), 244208_at (Checkpoint suppressor 1), 239984_at (Sodium channel, voltage-gated, type VII, alpha), 230683_at (CDNA:FLJ20892 fis, clone ADKA03430), 214869_at (apolipoprotein L, 6), 241597_at (Arginine-glutamic acid dipeptide (RE) repeats), 235887_at (Smg-6 homolog, nonsense mediated mRNA decay factor (*C. elegans*)), 229957_at (transmembrane protein 91), 223546_x_at (LUC7L-like (*S. cerevisiae*)), 239567_at (Rho GTPase activating protein 10), 242194_at (Cullin 4A), 1558525_at (hypothetical protein LOC283901), 227178_at (CUG triplet repeat, RNA binding protein 2), 228198_s_at (Mitochondrial ribosomal protein S9), 202379_s_at (natural killer-tumor recognition sequence), 224260_at (CDNA clone), 238643_at (Neuroblastoma, suppression of tumorigenicity 1), 232253_at (RAD50 homolog (*S. cerevisiae*)), 227968_at (Parkinson disease 7 domain containing 1), 233197_at (kelch-like 9 (*Drosophila*)), 244512_at (transcribed locus strongly similar to XP 0010813421), 233443_at (hypothetical protein LOC389362), 231275_at (FLJ42875 protein), 226419_s_at (hypothetical protein LOC64546), 201221_s_at small nuclear ribonucleoprotein 70 kDa polypeptide), 209354_at (tumor necrosis factor receptor family member 14), 226571_s_at (protein tyrosine phosphatase receptor type, S), 220728_at (EST), 203071_at (sema domain, immunoglobulin domain (Ig), short basic domain), 213946_s_at obscurin-like 1, similar to titin isoform N2-B), 201394_s_at (RNA binding motif protein 5), 203748_x_at (RNA binding motif, single stranded interacting protein 1), 223147_s_at (WD repeat domain 33), 213773_x_at (NOL/NOP2/Sun domain family, member 5), 1560049_at CUG triplet repeat, RNA binding protein 2), 243974_at (CDNA clone IMAGE:4821815), and 201510_at E74-like factor 3 (ets domain transcription factor, epithelial specific).

In a preferred embodiment, the biomarker is identified from a patient by isolating nucleic acids obtained from a biological sample.

In another preferred embodiment, the nucleic acids are hybridized to the biochip and raw intensity values from microarray hybridization are normalized and phenotype specific differences in gene expression are identified. The differences in gene expression are identified by significance analysis of microarrays, wherein significance is defined with a q-value and multiple comparisons comprise an adjusted p-value.

In another preferred embodiment, the phenotype specificity is identified by creating a classifier in a training set comprising about 66% of data obtained, with subsequent validation in a test set comprising about 33% of data obtained and defining a phenotype specific nearest shrunken centroid for classification. The phenotype specific nearest shrunken centroid comprises balancing about a 10-fold cross validation in a training set.

In another preferred embodiment, a method of predicting a prognostic outcome for heart disease or recovery from heart failure comprising: identifying in a biological sample from a patient a composition comprising biomoelcules: 232669_at (Hypoxia inducible factor 3, alpha subunit), 214951_at (solute carrier family 26, member 10), 243482_at (Epidermal growth factor receptor pathway substrate 15-like 1), 226210_s_at (maternally expressed 3), 232159_at (Epidermal growth factor receptor pathway substrate 15-like 1), 233026_s_at (PDZ domain containing), 211996_s_at (KIAA0220-like protein hypothetical gene LOC 283846), 243774_at (mucin 20, cell surface associated), 242551_at (Chromosome 18 open reading frame), 244548_at (Rho GTPase activating protein 26), 244208_at (Checkpoint suppressor 1), 239984_at (Sodium channel, voltage-gated, type VII, alpha), 230683_at (CDNA:FLJ20892 fis, clone ADKA03430), 214869_at (apolipoprotein L, 6), 241597_at (Arginine-glutamic acid dipeptide (RE) repeats), 235887_at (Smg-6 homolog, nonsense mediated mRNA decay factor (*C. elegans*)), 229957_at (transmembrane protein 91), 223546_x_at (LUC7L-like (*S. cerevisiae*)), 239567_at (Rho GTPase activating protein 10), 242194_at (Cullin 4A), 1558525_at (hypothetical protein LOC283901), 227178_at (CUG triplet repeat, RNA binding protein 2), 228198_s_at (Mitochondrial ribosomal protein S9), 202379_s_at (natural killer-tumor recognition sequence), 224260_at (CDNA clone), 238643_at (Neuroblastoma, suppression of tumorigenicity 1), 232253_at (RAD50 homolog (*S. cerevisiae*)), 227968_at (Parkinson disease 7 domain containing 1), 233197_at (kelch-like 9 (*Drosophila*)), 244512_at (transcribed locus strongly similar to XP 0010813421), 233443_at (hypothetical protein LOC389362), 231275_at (FLJ42875 protein), 226419_s_at (hypothetical protein LOC64546), 201221_s_at small nuclear ribonucleoprotein 70 kDa polypeptide), 209354_at (tumor necrosis factor receptor family member 14), 226571_s_at (protein tyrosine phosphatase receptor type, S), 220728_at (EST), 203071_at (sema domain, immunoglobulin domain (Ig), short basic domain), 213946_s_at obscurin-like 1, similar to titin isoform N2-B), 201394_s_at (RNA binding motif protein 5), 203748_x_at (RNA binding motif, single stranded interacting protein 1), 223147_s_at (WD repeat domain 33), 213773_x_at (NOL/NOP2/Sun domain family, member 5), 1560049_at CUG triplet repeat, RNA binding protein 2), 243974_at (CDNA clone IMAGE:4821815), 201510_at E74-like factor 3 (ets domain transcription factor, epithelial specific), complementary sequences, fragments, alleles, derivatives, variants and/or gene products thereof; and, assessing the probability of identification of each component gene in each sample; assigning each to a class; and, predicting the prognostic outcome for heart disease or recovery from heart failure.

In one embodiment, the biomolecules are over-expressed by at least about 5% as compared to a normal cell or normal subject.

In another preferred embodiment, a method of identifying and distinguishing between patients at a high risk of heart disease and patients with a good prognosis for recovery comprising: identifying biomolecules comprising: 232669_at (Hypoxia inducible factor 3, alpha subunit), 214951_at (solute carrier family 26, member 10), 243482_at (Epidermal growth factor receptor pathway substrate 15-like 1), 226210_s_at (maternally expressed 3), 232159_at (Epidermal growth factor receptor pathway substrate 15-like 1), 233026_s_at (PDZ domain containing), 211996_s_at (KIAA0220-like protein hypothetical gene LOC 283846), 243774_at (mucin 20, cell surface associated), 242551_at (Chromosome 18 open reading frame), 244548_at (Rho GTPase activating protein 26), 244208_at (Checkpoint suppressor 1), 239984_at (Sodium channel, voltage-gated, type VII, alpha), 230683_at (CDNA:FLJ20892 fis, clone ADKA03430), 214869_at (apolipoprotein L, 6), 241597_at (Arginine-glutamic acid dipeptide (RE) repeats), 235887_at (Smg-6 homolog, nonsense mediated mRNA decay factor (*C. elegans*)), 229957_at (transmembrane protein 91), 223546_x_at (LUC7L-like (*S. cerevisiae*)), 239567_at (Rho GTPase activating protein 10), 242194_at (Cullin 4A), 1558525_at (hypothetical protein LOC283901), 227178_at (CUG triplet repeat, RNA binding protein 2), 228198_s_at (Mitochondrial ribosomal protein S9), 202379_s_at (natural killer-tumor recognition sequence), 224260_at (CDNA clone), 238643_at (Neuroblastoma, suppression of tumorigenicity 1), 232253_at (RAD50 homolog (*S. cerevisiae*)), 227968_at (Parkinson disease 7 domain containing 1), 233197_at (kelch-like 9 (*Drosophila*)), 244512_at (transcribed locus strongly similar to XP 0010813421), 233443_at (hypothetical protein LOC389362), 231275_at (FLJ42875 protein), 226419_s_at (hypothetical protein LOC64546), 201221_s_at small nuclear ribonucleoprotein 70 kDa polypeptide), 209354_at (tumor necrosis factor receptor family member 14), 226571_s_at (protein tyrosine phosphatase receptor type, S), 220728_at (EST), 203071_at (sema domain, immunoglobulin domain (Ig), short basic domain), 213946_s_at obscurin-like 1, similar to titin isoform N2-B), 201394_s_at (RNA binding motif protein 5), 203748_x_at (RNA binding motif, single stranded interacting protein 1), 223147_s_at (WD repeat domain 33), 213773_x_at (NOL/NOP2/Sun domain family, member 5), 1560049_at CUG triplet repeat, RNA binding protein 2), 243974_at (CDNA clone IMAGE:4821815), 201510_at E74-like factor 3 (ets domain transcription factor, epithelial specific), complementary sequences, fragments, alleles, derivatives, variants and/or gene products thereof; assessing the probability of identification of each component gene in each sample; assigning each to a class; and, identifying and distinguishing between patients at a high risk of heart disease and patients with a good prognosis for recovery.

In another preferred embodiment, a molecular composition comprising biomolecules: 1558458_at (Hypothetical LOC401320), 1560049_at (CUG triplet repeat, RNA binding protein 2, CUGBP2), 201394_s_at (RNA binding motif protein 5, RBM5), 201655_s_at (heparan sulfate proteoglycan 2 (perlecan), HSPG2), 202379_s_at (natural killer-tumor recognition sequence, NKTR), 202808_at, 203071_at (sema domain, immunoglobulin domain (Ig), short basic domain, secreted, (semaphorin) 3B, SEMA3B), 203748_x_at (RNA binding motif, single stranded interacting protein 1, RBMS1), 203981_s_at (ATP-binding cassette, sub-family D (ALD), member 4, ABCD4), 204737_s_at (myosin, heavy chain 6, myosin, heavy chain 7, MYH6///MYH7), 204978_at (splicing factor, arginine/serine-rich 16, SFRS16), 206209_s_at (carbonic anhydrase IV, CA4), 207541_s_at (exosome component 10, EXOSC10), 207798_s_at (ataxin 2-like, ATXN2L), 208978_at (cysteine-rich protein 2, CRIP2), 209354_at (tumor necrosis factor receptor superfamily, member 14 TNFRSF14), 210628_x_at (latent transforming growth factor beta binding protein 4, LTBP4), 211909_x_at (prostaglandin E receptor 3 (subtype EP3), PTGER3), 211996_at (KIAA0220-like protein, nuclear pore complex (LOC23117), 212487_at (G patch domain containing 8, GPATCH8), 213946_s_at (obscurin-like 1, OBSL1), 214951_at (solute carrier family 26, member 10, SLC26A10), 220219_s_at (leucine rich repeat containing 37A, LRRC37A), 221071_at, 221780_s_at (DEAD (Asp-Glu-Ala-Asp) box polypeptide 27DDX27), 221806_s_at (SET domain containing 5, SETD5), 221833_at (Lon peptidase 2, peroxisomal, LONP2), 223546_x_at (LUC7-like (*S. cerevisiae*), LUC7L), 224260_at (CDNA clone IMAGE:4478733), 225562_at (AS p21 protein activator 3, RASA3), 226040_at (MRNA; cDNA DKFZp762N156 (from clone DKFZp762N156), 227968_at (Parkinson disease 7 domain containing 1, PDDC1), 228198_s_at (Mitochondrial ribosomal protein S9, MRPS9), 229830_at (Transcribed locus), 230683_at (CDNA: FLJ20892 fis, clone ADKA03430), 238185_at (RNA binding motif, single stranded interacting protein 1, RBMS1), 241597_at (Arginine-glutamic acid dipeptide (RE) repeats, RERE), 242551_at (Chromosome 18 open reading frame 1, C18orf1), 244208_at (Checkpoint suppressor 1, CHES1), 244494_at (Zinc finger, DHHC-type containing 1, ZDHHC1), and 244548_at (Rho GTPase activating protein 26, ARHGAP26) complementary sequences, fragments, derivatives, alleles, variants and/or gene products thereof.

Preferably, the detection in a cell or patient of the biomolecules, complementary sequences, fragments, alleles, derivatives, variants and gene products thereof, is predictive of clinical diagnostic outcome and prognosis of heart failure, predictive of prognostic outcome or diagnostic of cardiac and cardiovascular diseases and disorders, such as for example, myocarditis, Coronary Heart Disease, angina, Acute Coronary Syndrome, Aortic Aneurysm and Dissection, arrhythmias, Cardiomyopathy, Congenital Heart Disease, congestive heart failure or chronic heart failure, pericarditis, and the like.

Preferably, the biomolecules, complementary sequences, fragments, alleles, variants, derivatives and/or gene products thereof, are modulated and/or over-expressed at levels by at least 1% to a 100%, 200%, 300% or more in a cell or patient as compared to levels in a normal cell or normal subject.

Preferably, the biomolecules, complementary sequences, fragments, alleles, derivatives, variants and gene products thereof, produce a molecular signature or expression profile, wherein one or more biomolecules are differentially expressed to each other and to normal controls.

In an alternative embodiment, at least nine biomolecules are prognostic in individual risk assessment in a patient, predictive of clinical diagnostic outcome and prognosis of heart failure.

In another preferred embodiment, a plurality of gene sequences are prognostic in individual risk assessment in a patient for onset of heart failure.

In another preferred embodiment, a biomarker (TBB) predictive of clinical diagnostic outcome and prognosis of heart failure, comprising nucleic acid sequences/biomolecules comprising: 1558458_at (Hypothetical LOC401320), 1560049_at (CUG triplet repeat, RNA binding protein 2, CUGBP2), 201394_s_at (RNA binding motif protein 5, RBM5), 201655_s_at (heparan sulfate proteoglycan 2 (perlecan), HSPG2), 202379_s_at (natural killer-tumor recognition sequence, NKTR), 202808_at, 203071_at (sema domain, immunoglobulin domain (Ig), short basic domain, secreted, (semaphorin) 3B, SEMA3B), 203748_x_at (RNA binding motif, single stranded interacting protein 1, RBMS1), 203981_s_at (ATP-binding cassette, sub-family D (ALD), member 4, ABCD4), 204737_s_at (myosin, heavy chain 6, myosin, heavy chain 7, MYH6///MYH7), 204978_at (splicing factor, arginine/serine-rich 16, SFRS16), 206209_s_at (carbonic anhydrase IV, CA4), 207541_s_at (exosome component 10, EXOSC10), 207798_s_at (ataxin 2-like, ATXN2L), 208978_at (cysteine-rich protein 2, CRIP2), 209354_at (tumor necrosis factor receptor superfamily, member 14 TNFRSF14), 210628_x_at (latent transforming growth factor beta binding protein 4, LTBP4), 211909_x_at (prostaglandin E receptor 3 (subtype EP3), PTGER3), 211996_at (KIAA0220-like protein, nuclear pore complex (LOC23117), 212487_at (G patch domain containing 8, GPATCH8), 213946_s_at (obscurin-like 1, OBSL1), 214951_at (solute carrier family 26, member 10, SLC26A10), 220219_s_at (leucine rich repeat containing 37A, LRRC37A), 221071_at, 221780_s_at (DEAD (Asp-Glu-Ala-Asp) box polypeptide 27DDX27), 221806_s_at (SET domain containing 5, SETD5), 221833_at (Lon peptidase 2, peroxisomal, LONP2), 223546_x_at (LUC7-like (*S. cerevisiae*), LUC7L), 224260_at (CDNA clone IMAGE:4478733), 225562_at (AS p21 protein activator 3, RASA3), 226040_at (MRNA; cDNA DKFZp762N156 (from clone DKFZp762N156), 227968_at (Parkinson disease 7 domain containing 1, PDDC1), 228198_s_at (Mitochondrial ribosomal protein S9, MRPS9), 229830_at (Transcribed locus), 230683_at (CDNA: FLJ20892 fis, clone ADKA03430), 238185_at (RNA binding motif, single stranded interacting protein 1, RBMS1), 241597_at (Arginine-glutamic acid dipeptide (RE) repeats, RERE), 242551_at (Chromosome 18 open reading frame 1, C18orf1), 244208_at (Checkpoint suppressor 1, CHES1), 244494_at (Zinc finger, DHHC-type containing 1, ZDHHC1), and 244548_at (Rho GTPase activating protein 26, ARHGAP26) complementary sequences, fragments, alleles, derivatives, variants and/or gene products thereof.

In one embodiment, detection in a cell or patient of the gene sequences, complementary sequences, fragments, alleles, derivatives, variants and gene products thereof, is predictive of clinical diagnostic outcome and prognosis of heart failure, and is predictive of prognostic outcome or diagnostic of cardiac and cardiovascular diseases and disorders, such as for example, myocarditis, Coronary Heart Disease, angina, Acute Coronary Syndrome, Aortic Aneurysm and Dissection, arrhythmias, Cardiomyopathy, Congenital Heart Disease, congestive heart failure or chronic heart failure, pericarditis, and the like.

In another a biochip comprises nucleic acid sequences: 1558458_at (Hypothetical LOC401320), 1560049_at (CUG triplet repeat, RNA binding protein 2, CUGBP2), 201394_s_at (RNA binding motif protein 5, RBM5), 201655_s_at (heparan sulfate proteoglycan 2 (perlecan), HSPG2), 202379_s_at (natural killer-tumor recognition sequence, NKTR), 202808_at, 203071_at (sema domain, immunoglobulin domain (Ig), short basic domain, secreted, (semaphorin) 3B, SEMA3B), 203748_x_at (RNA binding motif, single stranded interacting protein 1, RBMS1), 203981_s_at (ATP-binding cassette, sub-family D (ALD), member 4, ABCD4), 204737_s_at (myosin, heavy chain 6, myosin, heavy chain 7, MYH6///MYH7), 204978_at (splicing factor, arginine/serine-rich 16, SFRS16), 206209_s_at (carbonic anhydrase IV, CA4), 207541_s_at (exosome component 10, EXOSC10), 207798_s_at (ataxin 2-like, ATXN2L), 208978_at (cysteine-rich protein 2, CRIP2), 209354_at (tumor necrosis factor receptor superfamily, member 14 TNFRSF14), 210628_x_at (latent transforming growth factor beta binding protein 4, LTBP4), 211909_x_at (prostaglandin E receptor 3 (subtype EP3), PTGER3), 211996_at (KIAA0220-like protein, nuclear pore complex (LOC23117), 212487_at (G patch domain containing 8, GPATCH8), 213946_s_at (obscurin-like 1, OBSL1), 214951_at (solute carrier family 26, member 10, SLC26A10), 220219_s_at (leucine rich repeat containing 37A, LRRC37A), 221071_at, 221780_s_at (DEAD (Asp-Glu-Ala-Asp) box polypeptide 27DDX27), 221806_s_at (SET domain containing 5, SETD5), 221833_at (Lon peptidase 2, peroxisomal, LONP2), 223546_x_at (LUC7-like (*S. cerevisiae*), LUC7L), 224260_at (CDNA clone IMAGE:4478733), 225562_at (AS p21 protein activator 3, RASA3), 226040_at (MRNA; cDNA DKFZp762N156 (from clone DKFZp762N156), 227968_at (Parkinson disease 7 domain containing 1, PDDC1), 228198_s_at (Mitochondrial ribosomal protein S9, MRPS9), 229830_at (Transcribed locus), 230683_at (CDNA: FLJ20892 fis, clone ADKA03430), 238185_at (RNA binding motif, single stranded interacting protein 1, RBMS1), 241597_at (Arginine-glutamic acid dipeptide (RE) repeats, RERE), 242551_at (Chromosome 18 open reading frame 1, C18orf1), 244208_at (Checkpoint suppressor 1, CHES1), 244494_at (Zinc finger, DHHC-type containing 1, ZDHHC1), and 244548_at (Rho GTPase activating protein 26, ARHGAP26), complementary sequences, fragments, alleles, derivatives, variants and/or gene products thereof.

In one embodiment, the biochip comprises at least ten nucleic acid sequences, complementary sequences, fragments, alleles, variants, derivatives and/or gene products thereof.

In another preferred embodiment, an antibody or aptamer is specific for each of: 1558458_at (Hypothetical LOC401320), 1560049_at (CUG triplet repeat, RNA binding protein 2, CUGBP2), 201394_s_at (RNA binding motif protein 5, RBM5), 201655_s_at (heparan sulfate proteoglycan 2 (perlecan), HSPG2), 202379_s_at (natural killer-tumor recognition sequence, NKTR), 202808_at, 203071_at (sema domain, immunoglobulin domain (Ig), short basic domain, secreted, (semaphorin) 3B, SEMA3B), 203748_x_at (RNA binding motif, single stranded interacting protein 1, RBMS1), 203981_s_at (ATP-binding cassette, sub-family D (ALD), member 4, ABCD4), 204737_s_at (myosin, heavy chain 6, myosin, heavy chain 7, MYH6///MYH7), 204978_at (splicing factor, arginine/serine-rich 16, SFRS16), 206209_s_at (carbonic anhydrase IV, CA4), 207541_s_at (exosome component 10, EXOSC10), 207798_s_at (ataxin 2-like, ATXN2L), 208978_at (cysteine-rich protein 2, CRIP2), 209354_at (tumor necrosis factor receptor superfamily, member 14 TNFRSF14), 210628_x_at (latent transforming growth factor beta binding protein 4, LTBP4), 211909_x_at (prostaglandin E receptor 3 (subtype EP3), PTGER3), 211996_at (KIAA0220-like protein, nuclear pore complex (LOC23117), 212487_at (G patch domain containing 8, GPATCH8), 213946_s_at (obscurin-like 1, OBSL1), 214951_at (solute carrier family 26, member 10, SLC26A10), 220219_s_at (leucine rich repeat containing 37A, LRRC37A), 221071_at, 221780_s_at (DEAD (Asp-Glu-Ala-Asp) box polypeptide 27DDX27), 221806_s_at (SET domain containing 5, SETD5), 221833_at (Lon peptidase 2, peroxisomal, LONP2), 223546_x_at (LUC7-like (*S. cerevisiae*), LUC7L), 224260_at (CDNA clone IMAGE:4478733), 225562_at (AS p21 protein activator 3, RASA3), 226040_at (MRNA; cDNA DKFZp762N156 (from clone DKFZp762N156), 227968_at (Parkinson disease 7 domain containing 1, PDDC1), 228198_s_at (Mitochondrial ribosomal protein S9, MRPS9), 229830_at (Transcribed locus), 230683_at (CDNA: FLJ20892 fis, clone ADKA03430), 238185_at (RNA binding motif, single stranded interacting protein 1, RBMS1), 241597_at (Arginine-glutamic acid dipeptide (RE) repeats, RERE), 242551_at (Chromosome 18 open reading frame 1, C18orf1), 244208_at (Checkpoint suppressor 1, CHES1), 244494_at (Zinc finger, DHHC-type containing 1, ZDHHC1), and 244548_at (Rho GTPase activating protein 26, ARHGAP26) complementary sequences, fragments, derivatives, alleles, variants and/or gene products thereof.

In another preferred embodiment, a method of assessing, identifying and distinguishing between patients at a high risk of heart disease and patients with a good prognosis for recovery comprises identifying in a biological sample from a patient a molecular signature comprising a transcriptomic based biomarker (TBB): 1558458_at (Hypothetical LOC401320), 1560049_at (CUG triplet repeat, RNA binding protein 2, CUGBP2), 201394_s_at (RNA binding motif protein 5, RBM5), 201655_s_at (heparan sulfate proteoglycan 2 (perlecan), HSPG2), 202379_s_at (natural killer-tumor recognition sequence, NKTR), 202808_at, 203071_at (sema domain, immunoglobulin domain (Ig), short basic domain, secreted, (semaphorin) 3B, SEMA3B), 203748_x_at (RNA binding motif, single stranded interacting protein 1, RBMS1), 203981_s_at (ATP-binding cassette, sub-family D (ALD), member 4, ABCD4), 204737_s_at (myosin, heavy chain 6, myosin, heavy chain 7, MYH6///MYH7), 204978_at (splicing factor, arginine/serine-rich 16, SFRS16), 206209_s_at (carbonic anhydrase IV, CA4), 207541_s_at (exosome component 10, EXOSC10), 207798_s_at (ataxin 2-like, ATXN2L), 208978_at (cysteine-rich protein 2, CRIP2), 209354_at (tumor necrosis factor receptor superfamily, member 14 TNFRSF14), 210628_x_at (latent transforming growth factor beta binding protein 4, LTBP4), 211909_x_at (prostaglandin E receptor 3 (subtype EP3), PTGER3), 211996_at (KIAA0220-like protein, nuclear pore complex (LOC23117), 212487_at (G patch domain containing 8, GPATCH8), 213946_s_at (obscurin-like 1, OBSL1), 214951_at (solute carrier family 26, member 10, SLC26A10), 220219_s_at (leucine rich repeat containing 37A, LRRC37A), 221071_at, 221780_s_at (DEAD (Asp-Glu-Ala-Asp) box polypeptide 27DDX27), 221806_s_at (SET domain containing 5, SETD5), 221833_at (Lon peptidase 2, peroxisomal, LONP2), 223546_x_at (LUC7-like (S. cerevisiae), LUC7L), 224260_at (CDNA clone IMAGE:4478733), 225562_at (AS p21 protein activator 3, RASA3), 226040_at (MRNA; cDNA DKFZp762N156 (from clone DKFZp762N156), 227968_at (Parkinson disease 7 domain containing 1, PDDC1), 228198_s_at (Mitochondrial ribosomal protein S9, MRPS9), 229830_at (Transcribed locus), 230683_at (CDNA: FLJ20892 fis, clone ADKA03430), 238185_at (RNA binding motif, single stranded interacting protein 1, RBMS1), 241597_at (Arginine-glutamic acid dipeptide (RE) repeats, RERE), 242551_at (Chromosome 18 open reading frame 1, C18orf1), 244208_at (Checkpoint suppressor 1, CHES1), 244494_at (Zinc finger, DHHC-type containing 1, ZDHHC1), and 244548_at (Rho GTPase activating protein 26, ARHGAP26), complementary sequences, fragments, alleles, derivatives, variants and/or gene products thereof; and, assessing the probability of identification of each component gene in each sample; assigning each to a class; and, predicting heart disease or cardiomyopathy.

In another preferred embodiment, a method of identifying and distinguishing between patients at a high risk of heart disease and patients with a good prognosis for recovery comprises identifying gene sequences comprising: 1558458_at (Hypothetical LOC401320), 1560049_at (CUG triplet repeat, RNA binding protein 2, CUGBP2), 201394_s_at (RNA binding motif protein 5, RBM5), 201655_s_at (heparan sulfate proteoglycan 2 (perlecan), HSPG2), 202379_s_at (natural killer-tumor recognition sequence, NKTR), 202808_at, 203071_at (sema domain, immunoglobulin domain (Ig), short basic domain, secreted, (semaphorin) 3B, SEMA3B), 203748_x_at (RNA binding motif, single stranded interacting protein 1, RBMS1), 203981_s_at (ATP-binding cassette, sub-family D (ALD), member 4, ABCD4), 204737_s_at (myosin, heavy chain 6, myosin, heavy chain 7, MYH6///MYH7), 204978_at (splicing factor, arginine/serine-rich 16, SFRS16), 206209_s_at (carbonic anhydrase IV, CA4), 207541_s_at (exosome component 10, EXOSC10), 207798_s_at (ataxin 2-like, ATXN2L), 208978_at (cysteine-rich protein 2, CRIP2), 209354_at (tumor necrosis factor receptor superfamily, member 14 TNFRSF14), 210628_x_at (latent transforming growth factor beta binding protein 4, LTBP4), 211909_x_at (prostaglandin E receptor 3 (subtype EP3), PTGER3), 211996_at (KIAA0220-like protein, nuclear pore complex (LOC23117), 212487_at (G patch domain containing 8, GPATCH8), 213946_s_at (obscurin-like 1, OBSL1), 214951_at (solute carrier family 26, member 10, SLC26A10), 220219_s_at (leucine rich repeat containing 37A, LRRC37A), 221071_at, 221780_s_at (DEAD (Asp-Glu-Ala-Asp) box polypeptide 27DDX27), 221806_s_at (SET domain containing 5, SETD5), 221833_at (Lon peptidase 2, peroxisomal, LONP2), 223546_x_at (LUC7-like (*S. cerevisiae*), LUC7L), 224260_at (CDNA clone IMAGE: 4478733), 225562_at (AS p21 protein activator 3, RASA3), 226040_at (MRNA; cDNA DKFZp762N156 (from clone DKFZp762N156), 227968_at (Parkinson disease 7 domain containing 1, PDDC1), 228198_s_at (Mitochondrial ribosomal protein S9, MRPS9), 229830_at (Transcribed locus), 230683_at (CDNA: FLJ20892 fis, clone ADKA03430), 238185_at (RNA binding motif, single stranded interacting protein 1, RBMS1), 241597_at (Arginine-glutamic acid dipeptide (RE) repeats, RERE), 242551_at (Chromosome 18 open reading frame 1, C18orf1), 244208_at (Checkpoint suppressor 1, CHES1), 244494_at (Zinc finger, DHHC-type containing 1, ZDHHC1), and 244548_at (Rho GTPase activating protein 26, ARHGAP26) complementary sequences, fragments, alleles, derivatives, variants and/or gene products thereof; assessing the probability of identification of each component gene in each sample; assigning each to a class; and, identifying and distinguishing between patients at a high risk of heart disease and patients with a good prognosis for recovery.

In another preferred embodiment, a cell expressing any one or more of nucleic acid sequences or products thereof: 232669_at (Hypoxia inducible factor 3, alpha subunit), 214951_at (solute carrier family 26, member 10), 243482_at (Epidermal growth factor receptor pathway substrate 15-like 1), 226210_s_at (maternally expressed 3), 232159_at (Epidermal growth factor receptor pathway substrate 15-like 1), 233026_s_at (PDZ domain containing), 211996_s_at (KIAA0220-like protein hypothetical gene LOC 283846), 243774_at (mucin 20, cell surface associated), 242551_at (Chromosome 18 open reading frame), 244548_at (Rho GTPase activating protein 26), 244208_at (Checkpoint suppressor 1), 239984_at (Sodium channel, voltage-gated, type VII, alpha), 230683_at (CDNA:FLJ20892 fis, clone ADKA03430), 214869_at (apolipoprotein L, 6), 241597_at (Arginine-glutamic acid dipeptide (RE) repeats), 235887_at (Smg-6 homolog, nonsense mediated mRNA decay factor (*C. elegans*)), 229957_at (transmembrane protein 91), 223546_x_at (LUC7L-like (*S. cerevisiae*)), 239567_at (Rho GTPase activating protein 10), 242194_at (Cullin 4A), 1558525_at (hypothetical protein LOC283901), 227178_at (CUG triplet repeat, RNA binding protein 2), 228198_s_at (Mitochondrial ribosomal protein S9), 202379_s_at (natural killer-tumor recognition sequence), 224260_at (CDNA clone), 238643_at (Neuroblastoma, suppression of tumorigenicity 1), 232253_at (RAD50 homolog (*S. cerevisiae*)), 227968_at (Parkinson disease 7 domain containing 1), 233197_at (kelch-like 9 (*Drosophila*)), 244512_at (transcribed locus strongly similar to XP 0010813421), 233443_at (hypothetical protein LOC389362), 231275_at (FLJ42875 protein), 226419_s_at (hypothetical protein LOC64546), 201221_s_at small nuclear ribonucleoprotein 70 kDa polypeptide), 209354_at (tumor necrosis factor receptor family member 14), 226571_s_at (protein tyrosine phosphatase receptor type, S), 220728_at (EST), 203071_at (sema domain, immunoglobulin domain (Ig), short basic domain), 213946_s_at obscurin-like 1, similar to titin isoform N2-B), 201394_s_at (RNA binding motif protein 5), 203748_x_at (RNA binding motif, single stranded interacting protein 1), 223147_s_at (WD repeat domain 33), 213773_x_at (NOL/NOP2/Sun domain family, member 5), 1560049_at CUG triplet repeat, RNA binding protein 2), 243974_at (CDNA clone IMAGE:4821815), 201510_at E74-like factor 3 (ets domain transcription factor, epithelial specific).

In another preferred embodiment, a vector expressing any one or more nucleic acid products comprising: 232669_at (Hypoxia inducible factor 3, alpha subunit), 214951_at (solute carrier family 26, member 10), 243482_at (Epidermal growth factor receptor pathway substrate 15-like 1), 226210_s_at (maternally expressed 3), 232159_at (Epidermal growth factor receptor pathway substrate 15-like 1), 233026_s_at (PDZ domain containing), 211996_s_at (KIAA0220-like protein hypothetical gene LOC 283846), 243774_at (mucin 20, cell surface associated), 242551_at (Chromosome 18 open reading frame), 244548_at (Rho GTPase activating protein 26), 244208_at (Checkpoint suppressor 1), 239984_at (Sodium channel, voltage-gated, type VII, alpha), 230683_at (CDNA:FLJ20892 fis, clone ADKA03430), 214869_at (apolipoprotein L, 6), 241597_at (Arginine-glutamic acid dipeptide (RE) repeats), 235887_at (Smg-6 homolog, nonsense mediated mRNA decay factor (*C. elegans*)), 229957_at (transmembrane protein 91), 223546_x_at (LUC7L-like (*S. cerevisiae*)), 239567_at (Rho GTPase activating protein 10), 242194_at (Cullin 4A), 1558525_at (hypothetical protein LOC283901), 227178_at (CUG triplet repeat, RNA binding protein 2), 228198_s_at (Mitochondrial ribosomal protein S9), 202379_s_at (natural killer-tumor recognition sequence), 224260_at (CDNA clone), 238643_at (Neuroblastoma, suppression of tumorigenicity 1), 232253_at (RAD50 homolog (*S. cerevisiae*)), 227968_at (Parkinson disease 7 domain containing 1), 233197_at (kelch-like 9 (*Drosophila*)), 244512_at (transcribed locus strongly similar to XP 0010813421), 233443_at (hypothetical protein LOC389362), 231275_at (FLJ42875 protein), 226419_s_at (hypothetical protein LOC64546), 201221_s_at small nuclear ribonucleoprotein 70 kDa polypeptide), 209354_at (tumor necrosis factor receptor family member 14), 226571_s_at (protein tyrosine phosphatase receptor type, S), 220728_at (EST), 203071_at (sema domain, immunoglobulin domain (Ig), short basic domain), 213946_s_at obscurin-like 1, similar to titin isoform N2-B), 201394_s_at (RNA binding motif protein 5), 203748_x_at (RNA binding motif, single stranded interacting protein 1), 223147_s_at (WD repeat domain 33), 213773_x_at (NOL/NOP2/Sun domain family, member 5), 1560049_at CUG triplet repeat, RNA binding protein 2), 243974_at (CDNA clone IMAGE: 4821815), 201510_at E74-like factor 3 (ets domain transcription factor, epithelial specific) or combinations thereof.

In another preferred embodiment, a cell expresses any one or more of nucleic acid sequences or products thereof comprising: 1558458_at (Hypothetical LOC401320), 1560049_at (CUG triplet repeat, RNA binding protein 2, CUGBP2), 201394_s_at (RNA binding motif protein 5, RBM5), 201655_s_at (heparan sulfate proteoglycan 2 (perlecan), HSPG2), 202379_s_at (natural killer-tumor recognition sequence, NKTR), 202808_at, 203071_at (sema domain, immunoglobulin domain (Ig), short basic domain, secreted, (semaphorin) 3B, SEMA3B), 203748_x_at (RNA binding motif, single stranded interacting protein 1, RBMS1), 203981_s_at (ATP-binding cassette, sub-family D (ALD), member 4, ABCD4), 204737_s_at (myosin, heavy chain 6, myosin, heavy chain 7, MYH6///MYH7), 204978_at (splicing factor, arginine/serine-rich 16, SFRS16), 206209_s_at (carbonic anhydrase IV, CA4), 207541_s_at (exosome component 10, EXOSC10), 207798_s_at (ataxin 2-like, ATXN2L), 208978_at (cysteine-rich protein 2, CRIP2), 209354_at (tumor necrosis factor receptor superfamily, member 14 TNFRSF14), 210628_x_at (latent transforming growth factor beta binding protein 4, LTBP4), 211909_x_at (prostaglandin E receptor 3 (subtype EP3), PTGER3), 211996_at (KIAA0220-like protein, nuclear pore complex (LOC23117), 212487_at (G patch domain containing 8, GPATCH8), 213946_s_at (obscurin-like 1, OBSL1), 214951_at (solute carrier family 26, member 10, SLC26A10), 220219_s_at (leucine rich repeat containing 37A, LRRC37A), 221071_at, 221780_s_at (DEAD (Asp-Glu-Ala-Asp) box polypeptide 27DDX27), 221806_s_at (SET domain containing 5, SETD5), 221833_at (Lon peptidase 2, peroxisomal, LONP2), 223546_x_at (LUC7-like (S. cerevisiae), LUC7L), 224260_at (CDNA clone IMAGE:4478733), 225562_at (AS p21 protein activator 3, RASA3), 226040_at (MRNA; cDNA DKFZp762N156 (from clone DKFZp762N156), 227968_at (Parkinson disease 7 domain containing 1, PDDC1), 228198_s_at (Mitochondrial ribosomal protein S9, MRPS9), 229830_at (Transcribed locus), 230683_at (CDNA: FLJ20892 fis, clone ADKA03430), 238185_at (RNA binding motif, single stranded interacting protein 1, RBMS1), 241597_at (Arginine-glutamic acid dipeptide (RE) repeats, RERE), 242551_at (Chromosome 18 open reading frame 1, C18orf1), 244208_at (Checkpoint suppressor 1, CHES1), 244494_at (Zinc finger, DHHC-type containing 1, ZDHHC1), and 244548_at (Rho GTPase activating protein 26, ARHGAP26) complementary sequences, fragments, alleles, derivatives, variants and/or gene products thereof.

In another preferred embodiment, a vector expresses any one or more of nucleic acid sequences comprising: 1558458_at (Hypothetical LOC401320), 1560049_at (CUG triplet repeat, RNA binding protein 2, CUGBP2), 201394_s_at (RNA binding motif protein 5, RBM5), 201655_s_at (heparan sulfate proteoglycan 2 (perlecan), HSPG2), 202379_s_at (natural killer-tumor recognition sequence, NKTR), 202808_at, 203071_at (sema domain, immunoglobulin domain (Ig), short basic domain, secreted, (semaphorin) 3B, SEMA3B), 203748_x_at (RNA binding motif, single stranded interacting protein 1, RBMS1), 203981_s_at (ATP-binding cassette, sub-family D (ALD), member 4, ABCD4), 204737_s_at (myosin, heavy chain 6, myosin, heavy chain 7, MYH6///MYH7), 204978_at (splicing factor, arginine/serine-rich 16, SFRS16), 206209_s_at (carbonic anhydrase IV, CA4), 207541_s_at (exosome component 10, EXOSC10), 207798_s_at (ataxin 2-like, ATXN2L), 208978_at (cysteine-rich protein 2, CRIP2), 209354_at (tumor necrosis factor receptor superfamily, member 14 TNFRSF14), 210628_x_at (latent transforming growth factor beta binding protein 4, LTBP4), 211909_x_at (prostaglandin E receptor 3 (subtype EP3), PTGER3), 211996_at (KIAA0220-like protein, nuclear pore complex (LOC23117), 212487_at (G patch domain containing 8, GPATCH8), 213946_s_at (obscurin-like 1, OBSL1), 214951_at (solute carrier family 26, member 10, SLC26A10), 220219_s_at (leucine rich repeat containing 37A, LRRC37A), 221071_at, 221780_s_at (DEAD (Asp-Glu-Ala-Asp) box polypeptide 27DDX27), 221806_s_at (SET domain containing 5, SETD5), 221833_at (Lon peptidase 2, peroxisomal, LONP2), 223546_x_at (LUC7-like (S. cerevisiae), LUC7L), 224260_at (CDNA clone IMAGE: 4478733), 225562_at (AS p21 protein activator 3, RASA3), 226040_at (MRNA; cDNA DKFZp762N156 (from clone DKFZp762N156), 227968_at (Parkinson disease 7 domain containing 1, PDDC1), 228198_s_at (Mitochondrial ribosomal protein S9, MRPS9), 229830_at (Transcribed locus), 230683_at (CDNA: FLJ20892 fis, clone ADKA03430), 238185_at (RNA binding motif, single stranded interacting protein 1, RBMS1), 241597_at (Arginine-glutamic acid dipeptide (RE) repeats, RERE), 242551_at (Chromosome 18 open reading frame 1, C18orf1), 244208_at (Checkpoint suppressor 1, CHES1), 244494_at (Zinc finger, DHHC-type containing 1, ZDHHC1), and 244548_at (Rho GTPase activating protein 26, ARHGAP26) complementary sequences, fragments, alleles, variants, derivatives and/or gene products thereof.

Other aspects of the invention are described infra.

BRIEF DESCRIPTION OF THE DRAWINGS

The invention is pointed out with particularity in the appended claims. The above and further advantages of this invention may be better understood by referring to the following description taken in conjunction with the accompanying drawings, in which:

DETAILED DESCRIPTION

Figure 1:
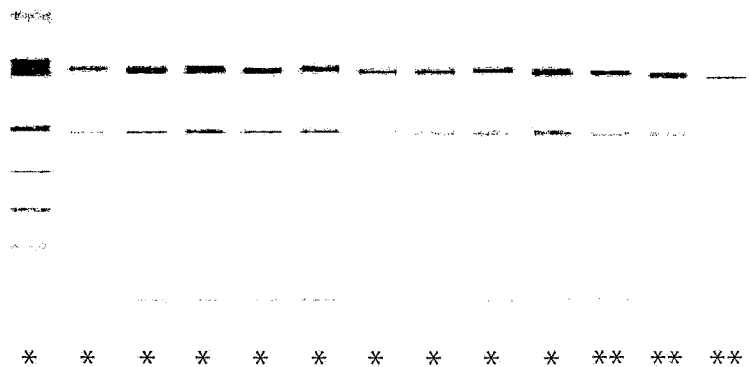
FIG. 1 is a scan of a photograph showing an analysis of extracted total RNA with Agilent 2100 Bioanalyzer: Every sample was tested for its integrity and purity before microarray hybridization. The photograph depicts a gel of 12 samples with consistent bands of 18S and 28S RNA. The left lane contains the reference marker.

The invention comprises molecular signatures that function as very sensitive prognostic biomarker for heart failure, heart diseases, myocarditis, and other heart disorders.

Prediction of prognosis remains a major unmet need in new onset heart failure (HF). While several clinical tests are in use, none accurately distinguish between patients with poor vs. excellent survival. A transcriptomic signature, generated from an endomyocardial biopsy (EMB), serves as a novel prognostic biomarker in HF.

Several aspects of the invention are described below with reference to example applications for illustration. It should be understood that numerous specific details, relationships, and methods are set forth to provide a full understanding of the invention. One having ordinary skill in the relevant art, however, will readily recognize that the invention can be practiced without one or more of the specific details or with other methods. In other instances, well-known structures or operations are not shown in detail to avoid obscuring the invention. The present invention is not limited by the illustrated ordering of acts or events, as some acts may occur in different orders and/or concurrently with other acts or events. Furthermore, not all illustrated acts or events are required to implement a methodology in accordance with the present invention.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

All genes, gene names, and gene products disclosed herein are intended to correspond to homologs from any species for which the compositions and methods disclosed herein are applicable. Thus, the terms include, but are not limited to genes and gene products from humans and mice. It is understood that when a gene or gene product from a particular species is disclosed, this disclosure is intended to be exemplary only, and is not to be interpreted as a limitation unless the context in which it appears clearly indicates. Thus, for example, for the genes disclosed herein, which in some embodiments relate to mammalian nucleic acid and amino acid sequences are intended to encompass homologous and/or orthologous genes and gene products from other animals including, but not limited to other mammals, fish, amphibians, reptiles, and birds. In preferred embodiments, the genes or nucleic acid sequences are human.

Definitions

The terminology used herein is for the purpose of describing particular embodiments only and is not intended to be limiting of the invention. As used herein, the singular forms "a", "an" and "the" are intended to include the plural forms as well, unless the context clearly indicates otherwise. Furthermore, to the extent that the terms "including", "includes", "having", "has", "with", or variants thereof are used in either the detailed description and/or the claims, such terms are intended to be inclusive in a manner similar to the term "comprising."

The term "about" or "approximately" means within an acceptable error range for the particular value as determined by one of ordinary skill in the art, which will depend in part on how the value is measured or determined, i.e., the limitations of the measurement system. For example, "about" can mean within 1 or more than 1 standard deviation, per the practice in the art. Alternatively, "about" can mean a range of up to 20%, preferably up to 10%, more preferably up to 5%, and more preferably still up to 1% of a given value. Alternatively, particularly with respect to biological systems or processes, the term can mean within an order of magnitude, preferably within 5-fold, and more preferably within 2-fold, of a value. Where particular values are described in the application and claims, unless otherwise stated the term "about" meaning within an acceptable error range for the particular value should be assumed.

As used herein, a "molecular signature" or "signature" or "biomarker" or "transcriptomic based biomarker" are used interchangeably herein and refers to all the biomolecules identified in, for example, Tables 2, and 8. Thus, Table 2 comprising the biomolecules listed therein, represents one biomarker or molecular signature; Table 8 comprising the biomolecules listed therein, represents another one biomarker or molecular signature; and so forth. As more biomolecules are discovered, each newly identified biomolecules can be assigned to any one or more biomarker or molecular signature. Each biomolecule can also be removed, reassigned or reallocated to a molecular signature. Thus, in some embodiments the molecular signature comprises at least ten biomolecules. Any one of the biomarkers or combinations thereof can be used in the prognosis of cardiovascular diseases.

The terms "biomolecule" or "markers" are used interchangeably herein and refer to DNA, RNA (including mRNA, rRNA, tRNA and tmRNA), nucleotides, nucleosides, analogs, polynucleotides, peptides and any combinations thereof.

A base "position" as used herein refers to the location of a given base or nucleotide residue within a nucleic acid.

As used herein, the term "array" refers to an ordered spatial arrangement, particularly an arrangement of immobilized biomolecules.

As used herein, the term "addressable array" refers to an array wherein the individual elements have precisely defined x and y coordinates, so that a given element at a particular position in the array can be identified.

As used herein, the terms "probe" and "biomolecular probe" refer to a biomolecule used to detect a complementary biomolecule. Examples include antigens that detect antibodies, oligonucleotides that detect complimentary oligonucleotides, and ligands that detect receptors. Such probes are preferably immobilized on a microelectrode comprising a substrate.

As used herein, the terms "bioarray," "biochip" and "biochip array" refer to an ordered spatial arrangement of immobilized biomolecules on a microelectrode arrayed on a solid supporting substrate. Preferred probe molecules include aptamers, nucleic acids, oligonucleotides, peptides, ligands, antibodies and antigens; peptides and proteins are the most preferred probe species. Biochips, as used in the art, encompass substrates containing arrays or microarrays, preferably ordered arrays and most preferably ordered, addressable arrays, of biological molecules that comprise one member of a biological binding pair. Typically, such arrays are oligonucleotide arrays comprising a nucleotide sequence that is complementary to at least one sequence that may be or is expected to be present in a biological sample. Alternatively, and preferably, proteins, peptides or other small molecules can be arrayed in such biochips for performing, inter alia, immunological analyses (wherein the arrayed molecules are antigens) or assaying biological receptors (wherein the arrayed molecules are ligands, agonists or antagonists of said receptors).

Expression/amount of a gene, biomolecule, or biomarker in a first sample is at a level "greater than" the level in a second sample if the expression level/amount of the gene or biomarker in the first sample is at least about 1 time, 1.2 times, 1.5 times, 1.75 times, 2 times, 3 times, 4 times, 5 times, 6 times, 7 times, 8 times, 9 times, 10 times, 20 times, 30 times, the expression level/amount of the gene or biomarker in the second sample or a normal sample. Expression levels/amounts can be determined based on any suitable criterion known in the art, including but not limited to mRNA, cDNA, proteins, protein fragments and/or gene copy. Expression levels/amounts can be determined qualitatively and/or quantitatively.

By the term "modulate," it is meant that any of the mentioned activities, are, e.g., increased, enhanced, increased, agonized (acts as an agonist), promoted, decreased, reduced, suppressed blocked, or antagonized (acts as an antagonist). Modulation can increase activity more than 1-fold, 2-fold, 3-fold, 5-fold, 10-fold, 100-fold, etc., over baseline values. Modulation can also decrease its activity below baseline values.

The term, "complementary" means that two sequences are complementary when the sequence of one can bind to the sequence of the other in an anti-parallel sense wherein the 3'-end of each sequence binds to the 5'-end of the other sequence and each A, T(U), G, and C of one sequence is then aligned with a T(U), A, C, and G, respectively, of the other sequence. Normally, the complementary sequence of the oligonucleotide has at least 80% or 90%, preferably 95%, most preferably 100%, complementarity to a defined sequence. Preferably, alleles or variants thereof can be identified. A BLAST program also can be employed to assess such sequence identity.

The term "complementary sequence" as it refers to a polynucleotide sequence, relates to the base sequence in another nucleic acid molecule by the base-pairing rules. More particularly, the term or like term refers to the hybridization or base pairing between nucleotides or nucleic acids, such as; for instance, between the two strands of a double stranded DNA molecule or between an oligonucleotide primer and a primer binding site on a single stranded nucleic acid to be sequenced or amplified. Complementary nucleotides are, generally, A and T (or A and U), or C and G. Two single stranded RNA or DNA molecules are said to be substantially complementary when the nucleotides of one strand, optimally aligned and compared and with appropriate nucleotide insertions or deletions, pair with at least about 95% of the nucleotides of the other strand, usually at least about 98%, and more preferably from about 99% to about 100%. Complementary polynucleotide sequences can be identified by a variety of approaches including use of well-known computer algorithms and software, for example the BLAST program.

An "allele" or "variant" is an alternative form of a gene. Variants may result from at least one mutation in the nucleic acid sequence and may result in altered mRNAs or in polypeptides whose structure or function may or may not be altered. Any given natural or recombinant gene may have none, one, or many allelic forms. Common mutational changes that give rise to variants are generally ascribed to natural deletions, additions, or substitutions of nucleotides. Each of these types of changes may occur alone, or in combination with the others, one or more times in a given sequence. The term "variant," when used in the context of a polynucleotide sequence, may encompass a polynucleotide sequence related to a wild type gene. This definition may also include, for example, "allelic," "splice," "species," or "polymorphic" variants. A splice variant may have significant identity to a reference molecule, but will generally have a greater or lesser number of polynucleotides due to alternate splicing of exons during mRNA processing. The corresponding polypeptide may possess additional functional domains or an absence of domains. Species variants are polynucleotide sequences that vary from one species to another. Of particular utility in the invention are variants of wild type gene products. Variants may result from at least one mutation in the nucleic acid sequence and may result in altered mRNAs or in polypeptides whose structure or function may or may not be altered. Any given natural or recombinant gene may have none, one, or many allelic forms. Common mutational changes that give rise to variants are generally ascribed to natural deletions, additions, or substitutions of nucleotides. Each of these types of changes may occur alone, or in combination with the others, one or more times in a given sequence.

The resulting polypeptides generally will have significant amino acid identity relative to each other. A polymorphic variant is a variation in the polynucleotide sequence of a particular gene between individuals of a given species. Polymorphic variants also may encompass "single nucleotide polymorphisms" (SNPs) or single base mutations in which the polynucleotide sequence varies by one base. The presence of SNPs may be indicative of, for example, a certain population with a propensity for a disease state, that is susceptibility versus resistance.

Derivative polynucleotides include nucleic acids subjected to chemical modification, for example, replacement of hydrogen by an alkyl, acyl, or amino group. Derivatives, e.g., derivative oligonucleotides, may comprise non-naturally-occurring portions, such as altered sugar moieties or inter-sugar linkages. Exemplary among these are phosphorothioate and other sulfur containing species which are known in the art. Derivative nucleic acids may also contain labels, including radionucleotides, enzymes, fluorescent agents, chemiluminescent agents, chromogenic agents, substrates, cofactors, inhibitors, magnetic particles, and the like.

A "derivative" polypeptide or peptide is one that is modified, for example, by glycosylation, pegylation, phosphorylation, sulfation, reduction/alkylation, acylation, chemical coupling, or mild formalin treatment. A derivative may also be modified to contain a detectable label, either directly or indirectly, including, but not limited to, a radioisotope, fluorescent, and enzyme label.

As used herein, the term "aptamer" or "selected nucleic acid binding species" shall include non-modified or chemically modified RNA or DNA. The method of selection may be by, but is not limited to, affinity chromatography and the method of amplification by reverse transcription (RT) or polymerase chain reaction (PCR).

As used herein, the term "signaling aptamer" shall include aptamers with reporter molecules, preferably a fluorescent dye, appended to a nucleotide in such a way that upon conformational changes resulting from the aptamer's interaction with a ligand, the reporter molecules yields a differential signal, preferably a change in fluorescence intensity.

As used herein, the term "fragment or segment", as applied to a nucleic acid sequence, gene or polypeptide, will ordinarily be at least about 5 contiguous nucleic acid bases (for nucleic acid sequence or gene) or amino acids (for polypeptides), typically at least about 10 contiguous nucleic acid bases or amino acids, more typically at least about 20 contiguous nucleic acid bases or amino acids, usually at least about 30 contiguous nucleic acid bases or amino acids, preferably at least about 40 contiguous nucleic acid bases or amino acids, more preferably at least about 50 contiguous nucleic acid bases or amino acids, and even more preferably at least about 60 to 80 or more contiguous nucleic acid bases or amino acids in length. "Overlapping fragments" as used herein, refer to contiguous nucleic acid or peptide fragments which begin at the amino terminal end of a nucleic acid or protein and end at the carboxy terminal end of the nucleic acid or protein. Each nucleic acid or peptide fragment has at least about one contiguous nucleic acid or amino acid position in common with the next nucleic acid or peptide fragment, more preferably at least about three contiguous nucleic acid bases or amino acid positions in common, most preferably at least about ten contiguous nucleic acid bases amino acid positions in common.

"Biological samples" include solid and body fluid samples. Preferably, the sample is obtained from heart. However, the biological samples used in the present invention can include cells, protein or membrane extracts of cells, blood or biological fluids such as ascites fluid or brain fluid (e.g., cerebrospinal fluid). Examples of solid biological samples include, but are not limited to, samples taken from tissues of the central nervous system, bone, breast, kidney, cervix, endometrium, head/neck, gallbladder, parotid gland, prostate, pituitary gland, muscle, esophagus, stomach, small intestine, colon, liver, spleen, pancreas, thyroid, heart, lung, bladder, adipose, lymph node, uterus, ovary, adrenal gland, testes, tonsils and thymus. Examples of "body fluid samples" include, but are not limited to blood, serum, semen, prostate fluid, seminal fluid, urine, saliva, sputum, mucus, bone marrow, lymph, and tears.

"Sample" is used herein in its broadest sense. A sample comprising polynucleotides, polypeptides, peptides, antibodies and the like may comprise a bodily fluid; a soluble fraction of a cell preparation, or media in which cells were grown; a chromosome, an organelle, or membrane isolated or extracted from a cell; genomic DNA, RNA, or cDNA, polypeptides, or peptides in solution or bound to a substrate; a cell; a tissue; a tissue print; a fingerprint, skin or hair; and the like.

The term "diagnosis", as used in this specification refers to predict the type of disease or condition from a set of marker values and/or patient symptoms. This is in contrast to disease prediction, which is to predict the occurrence of disease before it occurs, and the term "prognosis", which is to predict disease progression at a future point in time from one or more indicator value(s) at a previous point in time.

The term "correlating," as used in this specification refers to a process in which a set of examples of clinical inputs from subjects, such as marker levels, and their corresponding outputs, such as whether a subject suffered from heart failure, are related to each other. This relationship can be determined by comparing such examples to examples from a control and/or disease-free population at a later point in time, and selecting those indicators which can differentiate between the two disease states as a function of time alone or in combination at a certain probability level. The selection process is described herein. The selected markers, each at a certain level range which might be a simple threshold, are said to be correlative or associative with one of the disease states. Said correlated markers can be then be used for disease detection, diagnosis, prognosis and/or treatment outcome. Preferred methods of correlating markers is by performing marker selection as described in detail in the examples section which follows. Methods can include a feature selection algorithm, statistics and classification by mapping functions described herein. A preferred probability level is a 3% chance, 5% chance, a 7% chance, a 10% chance, a 15% chance, a 20% chance, a 25% chance, a 30% chance, a 35% chance, a 40% chance, a 45% chance, a 50% chance, a 55% chance, a 60% chance, a 65% chance, a 70% chance, a 75% chance, a 80% chance, a 85% chance, a 90% chance, a 95% chance, and a 100% chance. Each of these values of probability is plus or minus 2% or less.

The terms "detecting", "detect", "identifying", "quantifying" includes assaying, quantitating, imaging or otherwise establishing the presence or absence of the transcriptomic biomarker, or combinations of biomolecules comprising the biomarker, and the like, or assaying for, imaging, ascertaining, establishing, or otherwise determining the prognosis and/or diagnosis of heart failure or any other cardiovascular diseases or conditions.

Transcriptomic Biomarker/Molecular Signatures

In a preferred embodiment, a biomarker for the prognosis of the outcome of heart failure comprises: biomolecules/ nucleic acid sequences comprising gene sequences: 232669_at (Hypoxia inducible factor 3, alpha subunit), 214951_at (solute carrier family 26, member 10), 243482_at (Epidermal growth factor receptor pathway substrate 15-like 1), 226210_s_at (maternally expressed 3), 232159_at (Epidermal growth factor receptor pathway substrate 15-like 1), 233026_s_at (PDZ domain containing), 211996_s_at (KIAA0220-like protein hypothetical gene LOC 283846), 243774_at (mucin 20, cell surface associated), 242551_at (Chromosome 18 open reading frame), 244548_at (Rho GTPase activating protein 26), 244208_at (Checkpoint suppressor 1), 239984_at (Sodium channel, voltage-gated, type VII, alpha), 230683_at (CDNA:FLJ20892 fis, clone ADKA03430), 214869_at (apolipoprotein L, 6), 241597_at (Arginine-glutamic acid dipeptide (RE) repeats), 235887_at (Smg-6 homolog, nonsense mediated mRNA decay factor (*C. elegans*)), 229957_at (transmembrane protein 91), 223546_x_at (LUC7L-like (*S. cerevisiae*)), 239567_at (Rho GTPase activating protein 10), 242194_at (Cullin 4A), 1558525_at (hypothetical protein LOC283901), 227178_at (CUG triplet repeat, RNA binding protein 2), 228198_s_at (Mitochondrial ribosomal protein S9), 202379_s_at (natural killer-tumor recognition sequence), 224260_at (CDNA clone), 238643_at (Neuroblastoma, suppression of tumorigenicity 1), 232253_at (RAD50 homolog (*S. cerevisiae*)), 227968_at (Parkinson disease 7 domain containing 1), 233197_at (kelch-like 9 (*Drosophila*)), 244512_at (transcribed locus strongly similar to XP 0010813421), 233443_at (hypothetical protein LOC389362), 231275_at (FLJ42875 protein), 226419_s_at (hypothetical protein LOC64546), 201221_s_at small nuclear ribonucleoprotein 70 kDa polypeptide), 209354_at (tumor necrosis factor receptor family member 14), 226571_s_at (protein tyrosine phosphatase receptor type, S), 220728_at (EST), 203071_at (sema domain, immunoglobulin domain (Ig), short basic domain), 213946_s_at obscurin-like 1, similar to titin isoform N2-B), 201394_s_at (RNA binding motif protein 5), 203748_x_at (RNA binding motif, single stranded interacting protein 1), 223147_s_at (WD repeat domain 33), 213773_x_at (NOL/NOP2/Sun domain family, member 5), 1560049_at CUG triplet repeat, RNA binding protein 2), 243974_at (CDNA clone IMAGE:4821815), 201510_at E74-like factor 3 (ets domain transcription factor, epithelial specific), complementary sequences, fragments, alleles, variants, derivatives and/or gene products thereof, is diagnostic of myocardial disorders. Preferably, the nucleic acid sequences, complementary sequences, fragments, alleles, variants, derivatives and/or gene products thereof, are modulated and/or over-expressed at levels by at least between about 1%, 1.2%, 2% 5%, 10%, 20% in a cell or patient as compared to levels in a normal cell or normal subject; more preferably, the nucleic acid sequences, complementary sequences, fragments, alleles, variants, derivatives and/or gene products thereof, are modulated and/or over-expressed by about 50% in a cell or a patient as compared to levels in a normal cell or normal subject; more preferably, the nucleic acid sequences, complementary sequences, fragments, alleles, variants, derivatives and/or gene products thereof, are modulated and/or over-expressed by about 75% in a cell or a patient as compared to levels in a normal cell or normal subject.

In another preferred embodiment, a biomarker comprises nucleic acid sequences: 1558458_at (Hypothetical LOC401320), 1560049_at (CUG triplet repeat, RNA binding protein 2, CUGBP2), 201394_s_at (RNA binding motif protein 5, RBM5), 201655_s_at (heparan sulfate proteoglycan 2 (perlecan), HSPG2), 202379_s_at (natural killer-tumor recognition sequence, NKTR), 202808_at, 203071_at (sema domain, immunoglobulin domain (Ig), short basic domain, secreted, (semaphorin) 3B, SEMA3B), 203748_x_at (RNA binding motif, single stranded interacting protein 1, RBMS1), 203981_s_at (ATP-binding cassette, sub-family D (ALD), member 4, ABCD4), 204737_s_at (myosin, heavy chain 6, myosin, heavy chain 7, MYH6/// MYH7), 204978_at (splicing factor, arginine/serine-rich 16, SFRS16), 206209_s_at (carbonic anhydrase IV, CA4), 207541_s_at (exosome component 10, EXOSC10), 207798_s_at (ataxin 2-like, ATXN2L), 208978_at (cysteine-rich protein 2, CRIP2), 209354_at (tumor necrosis factor receptor superfamily, member 14 TNFRSF14), 210628_x_at (latent transforming growth factor beta binding protein 4, LTBP4), 211909_x_at (prostaglandin E receptor 3 (subtype EP3), PTGER3), 211996_s_at (KIAA0220-like protein, nuclear pore complex (LOC23117), 212487_at (G patch domain containing 8, GPATCH8), 213946_s_at (obscurin-like 1, OBSL1), 214951_at (solute carrier family 26, member 10, SLC26A10), 220219_s_at (leucine rich repeat containing 37A, LRRC37A), 221071_at, 221780_s_at (DEAD (Asp-Glu-Ala-Asp) box polypeptide 27DDX27), 221806_s_at (SET domain containing 5, SETD5), 221833_at (Lon peptidase 2, peroxisomal, LONP2), 223546_x_at (LUC7-like (*S. cerevisiae*), LUC7L), 224260_at (CDNA clone IMAGE:4478733), 225562_at (AS p21 protein activator 3, RASA3), 226040_at (MRNA; cDNA DKFZp762N156 (from clone DKFZp762N156), 227968_at (Parkinson disease 7 domain containing 1, PDDC1), 228198_s_at (Mitochondrial ribosomal protein S9, MRPS9), 229830_at (Transcribed locus), 230683_at (CDNA: FLJ20892 fis, clone ADKA03430), 238185_at (RNA binding motif, single stranded interacting protein 1, RBMS1), 241597_at (Arginine-glutamic acid dipeptide (RE) repeats, RERE), 242551_at (Chromosome 18 open reading frame 1, C18orf1), 244208_at (Checkpoint suppressor 1, CHES1), 244494_at (Zinc finger, DHHC-type containing 1, ZDHHC1), and 244548_at (Rho GTPase activating protein 26, ARHGAP26) complementary sequences, fragments, alleles, variants, derivatives and/or gene products thereof.

In another preferred embodiment, a biochip comprises a molecular signature/biomarker comprising nucleic acid sequences: a biomarker comprises gene sequences: 232669_at (Hypoxia inducible factor 3, alpha subunit), 214951_at (solute carrier family 26, member 10), 243482_at (Epidermal growth factor receptor pathway substrate 15-like 1), 226210_s_at (maternally expressed 3), 232159_at (Epidermal growth factor receptor pathway substrate 15-like 1), 233026_s_at (PDZ domain containing), 211996_s_at (KIAA0220-like protein hypothetical gene LOC 283846), 243774_at (mucin 20, cell surface associated), 242551_at (Chromosome 18 open reading frame), 244548_at (Rho GTPase activating protein 26), 244208_at (Checkpoint suppressor 1), 239984_at (Sodium channel, voltage-gated, type VII, alpha), 230683_at (CDNA:FLJ20892 fis, clone ADKA03430), 214869_at (apolipoprotein L, 6), 241597_at (Arginine-glutamic acid dipeptide (RE) repeats), 235887_at (Smg-6 homolog, nonsense mediated mRNA decay factor (*C. elegans*)), 229957_at (transmembrane protein 91), 223546_x_at (LUC7L-like (*S. cerevisiae*)), 239567_at (Rho GTPase activating protein 10), 242194_at (Cullin 4A), 1558525_at (hypothetical protein LOC283901), 227178_at (CUG triplet repeat, RNA binding protein 2), 228198_s_at (Mitochondrial ribosomal protein S9), 202379_s_at (natural killer-tumor recognition sequence), 224260_at (CDNA clone), 238643_at (Neuroblastoma, suppression of tumorigenicity 1), 232253_at (RAD50 homolog (*S. cerevisiae*)), 227968_at (Parkinson disease 7 domain containing 1), 233197_at (kelch-like 9 (*Drosophila*)), 244512_at (transcribed locus strongly similar to XP 0010813421), 233443_at (hypothetical protein LOC389362), 231275_at (FLJ42875 protein), 226419_s_at (hypothetical protein LOC64546), 201221_s_at small nuclear ribonucleoprotein 70 kDa polypeptide), 209354_at (tumor necrosis factor receptor family member 14), 226571_s_at (protein tyrosine phosphatase receptor type, S), 220728_at (EST), 203071_at (sema domain, immunoglobulin domain (Ig), short basic domain), 213946_s_at obscurin-like 1, similar to titin isoform N2-B), 201394_s_at (RNA binding motif protein 5), 203748_x_at (RNA binding motif, single stranded interacting protein 1), 223147_s_at (WD repeat domain 33), 213773_x_at (NOL/NOP2/Sun domain family, member 5), 1560049_at CUG triplet repeat, RNA binding protein 2), 243974_at (CDNA clone IMAGE:4821815), 201510_at E74-like factor 3 (ets domain transcription factor, epithelial specific), complementary sequences, fragments, alleles, variants, derivatives and/or gene products thereof.

In another preferred embodiment a biochip comprises nucleic acid sequences: 1558458_at (Hypothetical LOC401320), 1560049_at (CUG triplet repeat, RNA binding protein 2, CUGBP2), 201394_s_at (RNA binding motif protein 5, RBMS), 201655_s_at (heparan sulfate proteoglycan 2 (perlecan), HSPG2), 202379_s_at (natural killer-tumor recognition sequence, NKTR), 202808_at, 203071_at (sema domain, immunoglobulin domain (Ig), short basic domain, secreted, (semaphorin) 3B, SEMA3B), 203748_x_at (RNA binding motif, single stranded interacting protein 1, RBMS1), 203981_s_at (ATP-binding cassette, sub-family D (ALD), member 4, ABCD4), 204737_s_at (myosin, heavy chain 6, myosin, heavy chain 7, MYH6///MYH7), 204978_at (splicing factor, arginine/serine-rich 16, SFRS16), 206209_s_at (carbonic anhydrase IV, CA4), 207541_s_at (exosome component 10, EXOSC10), 207798_s_at (ataxin 2-like, ATXN2L), 208978_at (cysteine-rich protein 2, CRIP2), 209354_at (tumor necrosis factor receptor superfamily, member 14 TNFRSF14), 210628_x_at (latent transforming growth factor beta binding protein 4, LTBP4), 211909_x_at (prostaglandin E receptor 3 (subtype EP3), PTGER3), 211996_at (KIAA0220-like protein, nuclear pore complex (LOC23117), 212487_at (G patch domain containing 8, GPATCH8), 213946_s_at (obscurin-like 1, OBSL1), 214951_at (solute carrier family 26, member 10, SLC26A10), 220219_s_at (leucine rich repeat containing 37A, LRRC37A), 221071_at, 221780_s_at (DEAD (Asp-Glu-Ala-Asp) box polypeptide 27DDX27), 221806_s_at (SET domain containing 5, SETD5), 221833_at (Lon peptidase 2, peroxisomal, LONP2), 223546_x_at (LUC7-like (*S. cerevisiae*), LUC7L), 224260_at (CDNA clone IMAGE:4478733), 225562_at (AS p21 protein activator 3, RASA3), 226040_at (MRNA; cDNA DKFZp762N156 (from clone DKFZp762N156), 227968_at (Parkinson disease 7 domain containing 1, PDDC1), 228198_s_at (Mitochondrial ribosomal protein S9, MRPS9), 229830_at (Transcribed locus), 230683_at (CDNA: FLJ20892 fis, clone ADKA03430), 238185_at (RNA binding motif, single stranded interacting protein 1, RBMS1), 241597_at (Arginine-glutamic acid dipeptide (RE) repeats, RERE), 242551_at (Chromosome 18 open reading frame 1, C18orf1), 244208_at (Checkpoint suppressor 1, CHES1), 244494_at (Zinc finger, DHHC-type containing 1, ZDHHC1), and 244548_at (Rho GTPase activating protein 26, ARHGAP26) complementary sequences, fragments, alleles, variants, derivatives and/or gene products thereof.

In another preferred embodiment, a method of prognosis of heart failure comprises identifying in a biological sample from a patient a molecular signature comprising a transcriptomic based biomarker (TBB): a biomarker comprises gene sequences: 232669_at (Hypoxia inducible factor 3, alpha subunit), 214951_at (solute carrier family 26, member 10), 243482_at (Epidermal growth factor receptor pathway substrate 15-like 1), 226210_s_at (maternally expressed 3), 232159_at (Epidermal growth factor receptor pathway substrate 15-like 1), 233026_s_at (PDZ domain containing), 211996_s_at (KIAA0220-like protein hypothetical gene LOC 283846), 243774_at (mucin 20, cell surface associated), 242551_at (Chromosome 18 open reading frame), 244548_at (Rho GTPase activating protein 26), 244208_at (Checkpoint suppressor 1), 239984_at (Sodium channel, voltage-gated, type VII, alpha), 230683_at (CDNA: FLJ20892 fis, clone ADKA03430), 214869_at (apolipoprotein L, 6), 241597_at (Arginine-glutamic acid dipeptide (RE) repeats), 235887_at (Smg-6 homolog, nonsense mediated mRNA decay factor (*C. elegans*)), 229957_at (transmembrane protein 91), 223546_x_at (LUC7L-like (*S. cerevisiae*)), 239567_at (Rho GTPase activating protein 10), 242194_at (Cullin 4A), 1558525_at (hypothetical protein LOC283901), 227178_at (CUG triplet repeat, RNA binding protein 2), 228198_s_at (Mitochondrial ribosomal protein S9), 202379_s_at (natural killer-tumor recognition sequence), 224260_at (CDNA clone), 238643_at (Neuroblastoma, suppression of tumorigenicity 1), 232253_at (RAD50 homolog (*S. cerevisiae*)), 227968_at (Parkinson disease 7 domain containing 1), 233197_at (kelch-like 9 (*Drosophila*)), 244512_at (transcribed locus strongly similar to XP 0010813421), 233443_at (hypothetical protein LOC389362), 231275_at (FLJ42875 protein), 226419_s_at (hypothetical protein LOC64546), 201221_s_at small nuclear ribonucleoprotein 70 kDa polypeptide), 209354_at (tumor necrosis factor receptor family member 14), 226571_s_at (protein tyrosine phosphatase receptor type, S), 220728_at (EST), 203071_at (sema domain, immunoglobulin domain (Ig), short basic domain), 213946_s_at obscurin-like 1, similar to titin isoform N2-B), 201394_s_at (RNA binding motif protein 5), 203748_x_at (RNA binding motif, single stranded interacting protein 1), 223147_s_at (WD repeat domain 33), 213773_x_at (NOL/NOP2/Sun domain family, member 5), 1560049_at CUG triplet repeat, RNA binding protein 2), 243974_at (CDNA clone IMAGE: 4821815), 201510_at E74-like factor 3 (ets domain transcription factor, epithelial specific), complementary sequences, fragments, alleles, variants, derivatives and/or gene products thereof; assessing the probability of identification of each component gene in each sample; and assigning each to a class.

In another preferred embodiment, a method of predicting the clinical outcome and prognosis in heart failure comprises detection of a biomarker comprising: 1558458_at (Hypothetical LOC401320), 1560049_at (CUG triplet repeat, RNA binding protein 2, CUGBP2), 201394_s_at (RNA binding motif protein 5, RBM5), 201655_s_at (heparan sulfate proteoglycan 2 (perlecan), HSPG2), 202379_s_at (natural killer-tumor recognition sequence, NKTR), 202808_at, 203071_at (sema domain, immunoglobulin domain (Ig), short basic domain, secreted, (semaphorin) 3B, SEMA3B), 203748_x_at (RNA binding motif, single stranded interacting protein 1, RBMS1), 203981_s_at (ATP-binding cassette, sub-family D (ALD), member 4, ABCD4), 204737_s_at (myosin, heavy chain 6, myosin, heavy chain 7, MYH6///MYH7), 204978_at (splicing factor, arginine/serine-rich 16, SFRS16), 206209_s_at (carbonic anhydrase IV, CA4), 207541_s_at (exosome component 10, EXOSC10), 207798_s_at (ataxin 2-like, ATXN2L), 208978_at (cysteine-rich protein 2, CRIP2), 209354_at (tumor necrosis factor receptor superfamily, member 14 TNFRSF14), 210628_x_at (latent transforming growth factor beta binding protein 4, LTBP4), 211909_x_at (prostaglandin E receptor 3 (subtype EP3), PTGER3), 211996_at (KIAA0220-like protein, nuclear pore complex (LOC23117), 212487_at (G patch domain containing 8, GPATCH8), 213946_s_at (obscurin-like 1, OBSL1), 214951_at (solute carrier family 26, member 10, SLC26A10), 220219_s_at (leucine rich repeat containing 37A, LRRC37A), 221071_at, 221780_s_at (DEAD (Asp-Glu-Ala-Asp) box polypeptide 27DDX27), 221806_s_at (SET domain containing 5, SETD5), 221833_at (Lon peptidase 2, peroxisomal, LONP2), 223546_x_at (LUC7-like (*S. cerevisiae*), LUC7L), 224260_at (CDNA clone IMAGE: 4478733), 225562_at (AS p21 protein activator 3, RASA3), 226040_at (MRNA; cDNA DKFZp762N156 (from clone DKFZp762N156), 227968_at (Parkinson disease 7 domain containing 1, PDDC1), 228198_s_at (Mitochondrial ribosomal protein S9, MRPS9), 229830_at (Transcribed locus), 230683_at (CDNA: FLJ20892 fis, clone ADICA03430), 238185_at (RNA binding motif, single stranded interacting protein 1, RBMS1), 241597_at (Arginine-glutamic acid dipeptide (RE) repeats, RERE), 242551_at (Chromosome 18 open reading frame 1, C18orf1), 244208_at (Checkpoint suppressor 1, CHES1), 244494_at (Zinc finger, DHHC-type containing 1, ZDHHC1), and 244548_at (Rho GTPase activating protein 26, ARHGAP26) complementary sequences, fragments, alleles, variants, derivatives and/or gene products thereof.

In a preferred embodiment, phenotype specificity is identified by creating a classifier in a training set comprising about 66% of data obtained, with subsequent validation in a test set comprising about 33% of data obtained and defining a phenotype specific nearest shrunken centroid for classification.

In another preferred embodiment, a method of identifying and distinguishing between patients at a high risk of heart disease and patients with a good prognosis for recovery comprising: identifying in a biological sample from a patient a molecular signature comprising a transcriptomic based biomarker (TBB): a biomarker comprises gene sequences: 232669_at (Hypoxia inducible factor 3, alpha subunit), 214951_at (solute carrier family 26, member 10), 243482_at (Epidermal growth factor receptor pathway substrate 15-like 1), 226210_s_at (maternally expressed 3), 232159_at (Epidermal growth factor receptor pathway substrate 15-like 1), 233026_s_at (PDZ domain containing), 211996_s_at (KIAA0220-like protein hypothetical gene LOC 283846), 243774_at (mucin 20, cell surface associated), 242551_at (Chromosome 18 open reading frame), 244548_at (Rho GTPase activating protein 26), 244208_at (Checkpoint suppressor 1), 239984_at (Sodium channel, voltage-gated, type VII, alpha), 230683_at (CDNA:FLJ20892 fis, clone ADKA03430), 214869_at (apolipoprotein L, 6), 241597_at (Arginine-glutamic acid dipeptide (RE) repeats), 235887_at (Smg-6 homolog, nonsense mediated mRNA decay factor (*C. elegans*)), 229957_at (transmembrane protein 91), 223546_x_at (LUC7L-like (*S. cerevisiae*)), 239567_at (Rho GTPase activating protein 10), 242194_at (Cullin 4A), 1558525_at (hypothetical protein LOC283901), 227178_at (CUG triplet repeat, RNA binding protein 2), 228198_s_at (Mitochondrial ribosomal protein S9), 202379_s_at (natural killer-tumor recognition sequence), 224260_at (CDNA clone), 238643_at (Neuroblastoma, suppression of tumorigenicity 1), 232253_at (RAD50 homolog (*S. cerevisiae*)), 227968_at (Parkinson disease 7 domain containing 1), 233197_at (kelch-like 9 (*Drosophila*)), 244512_at (transcribed locus strongly similar to XP_0010813421), 233443_at (hypothetical protein LOC389362), 231275_at (FLJ42875 protein), 226419_s_at (hypothetical protein LOC64546), 201221_s_at small nuclear ribonucleoprotein 70 kDa polypeptide), 209354_at (tumor necrosis factor receptor family member 14), 226571_s_at (protein tyrosine phosphatase receptor type, S), 220728_at (EST), 203071_at (sema domain, immunoglobulin domain (Ig), short basic domain), 213946_s_at obscurin-like 1, similar to titin isoform N2-B), 201394_s_at (RNA binding motif protein 5), 203748_x_at (RNA binding motif, single stranded interacting protein 1), 223147_s_at (WD repeat domain 33), 213773_x_at (NOL/NOP2/Sun domain family, member 5), 1560049_at CUG triplet repeat, RNA binding protein 2), 243974_at (CDNA clone IMAGE:4821815), 201510_at E74-like factor 3 (ets domain transcription factor, epithelial specific), complementary sequences, fragments, alleles, variants, derivatives and/or gene products thereof; assessing the probability of identification of each component gene in each sample; assigning each to a class; and, identifying and distinguishing between patients at a high risk of heart disease and patients with a good prognosis for recovery.

In another preferred embodiment, a method of identifying and distinguishing between patients at a high risk of heart disease and patients with a good prognosis for recovery comprising: identifying in a biological sample from a patient a molecular signature comprising a transcriptomic based biomarker (TBB): a biomarker comprises gene sequences: 1558458_at (Hypothetical LOC401320), 1560049_at (CUG triplet repeat, RNA binding protein 2, CUGBP2), 201394_s_at (RNA binding motif protein 5, RBM5), 201655_s_at (heparan sulfate proteoglycan 2 (perlecan), HSPG2), 202379_s_at (natural killer-tumor recognition sequence, NKTR), 202808_at, 203071_at (sema domain, immunoglobulin domain (Ig), short basic domain, secreted, (semaphorin) 3B, SEMA3B), 203748_x_at (RNA binding motif, single stranded interacting protein 1, RBMS1), 203981_s_at (ATP-binding cassette, sub-family D (ALD), member 4, ABCD4), 204737_s_at (myosin, heavy chain 6, myosin, heavy chain 7, MYH6///MYH7), 204978_at (splicing factor, arginine/serine-rich 16, SFRS16), 206209_s_at (carbonic anhydrase IV, CA4), 207541_s_at (exosome component 10, EXOSC10), 207798_s_at (ataxin 2-like, ATXN2L), 208978_at (cysteine-rich protein 2, CRIP2), 209354_at (tumor necrosis factor receptor superfamily, member 14 TNFRSF14), 210628_x_at (latent transforming growth factor beta binding protein 4, LTBP4), 211909_x_at (prostaglandin E receptor 3 (subtype EP3), PTGER3), 211996_at (KIAA0220-like protein, nuclear pore complex (LOC23117), 212487_at (G patch domain containing 8, GPATCH8), 213946_s_at (obscurin-like 1, OBSL1), 214951_at (solute carrier family 26, member 10, SLC26A10), 220219_s_at (leucine rich repeat containing 37A, LRRC37A), 221071_at, 221780_s_at (DEAD (Asp-Glu-Ala-Asp) box polypeptide 27DDX27), 221806_s_at (SET domain containing 5, SETD5), 221833_at (Lon peptidase 2, peroxisomal, LONP2), 223546_x_at (LUC7-like (S. cerevisiae), LUC7L), 224260_at (CDNA clone IMAGE: 4478733), 225562_at (AS p21 protein activator 3, RASA3), 226040_at (MRNA; cDNA DKFZp762N156 (from clone DKFZp762N156), 227968_at (Parkinson disease 7 domain containing 1, PDDC1), 228198_s_at (Mitochondrial ribosomal protein S9, MRPS9), 229830_at (Transcribed locus), 230683_at (CDNA: FLJ20892 fis, clone ADKA03430), 238185_at (RNA binding motif, single stranded interacting protein 1, RBMS1), 241597_at (Arginine-glutamic acid dipeptide (RE) repeats, RERE), 242551_at (Chromosome 18 open reading frame 1, C18orf1), 244208_at (Checkpoint suppressor 1, CHES1), 244494_at (Zinc finger, DHHC-type containing 1, ZDHHC1), and 244548_at (Rho GTPase activating protein 26, ARHGAP26) complementary sequences, fragments, alleles, variants, derivatives and/or gene products thereof; assessing the probability of identification of each component gene in each sample; assigning each to a class; and, identifying and distinguishing between patients at a high risk of heart disease and patients with a good prognosis for recovery.

In another preferred embodiment, prediction of prognosis of heart-failure comprises detecting at least ten molecules having gene sequences comprising: 232669_at (Hypoxia inducible factor 3, alpha subunit), 214951_at (solute carrier family 26, member 10), 243482_at (Epidermal growth factor receptor pathway substrate 15-like 1), 226210_s_at (maternally expressed 3), 232159_at (Epidermal growth factor receptor pathway substrate 15-like 1), 233026_s_at (PDZ domain containing), 211996_s_at (KIAA0220-like protein hypothetical gene LOC 283846), 243774_at (mucin 20, cell surface associated), 242551_at (Chromosome 18 open reading frame), 244548_at (Rho GTPase activating protein 26), 244208_at (Checkpoint suppressor 1), 239984_at (Sodium channel, voltage-gated, type VII, alpha), 230683_at (CDNA:FLJ20892 fis, clone ADKA03430), 214869_at (apolipoprotein L, 6), 241597_at (Arginine-glutamic acid dipeptide (RE) repeats), 235887_at (Smg-6 homolog, non-sense mediated mRNA decay factor (C. elegans)), 229957_at (transmembrane protein 91), 223546_x_at (LUC7L-like (S. cerevisiae)), 239567_at (Rho GTPase activating protein 10), 242194_at (Cullin 4A), 1558525_at (hypothetical protein LOC283901), 227178_at (CUG triplet repeat, RNA binding protein 2), 228198_s_at (Mitochondrial ribosomal protein S9), 202379_s_at (natural killer-tumor recognition sequence), 224260_at (CDNA clone), 238643_at (Neuroblastoma, suppression of tumorigenicity 1), 232253_at (RAD50 homolog (S. cerevisiae)), 227968_at (Parkinson disease 7 domain containing 1), 233197_at (kelch-like 9 (Drosophila)), 244512_at (transcribed locus strongly similar to XP 0010813421), 233443_at (hypothetical protein LOC389362), 231275_at (FLJ42875 protein), 226419_s_at (hypothetical protein LOC64546), 201221_s_at small nuclear ribonucleoprotein 70 kDa polypeptide), 209354_at (tumor necrosis factor receptor family member 14), 226571_s_at (protein tyrosine phosphatase receptor type, S), 220728_at (EST), 203071_at (sema domain, immunoglobulin domain (Ig), short basic domain), 213946_s_at obscurin-like 1, similar to titin isoform N2-B), 201394_s_at (RNA binding motif protein 5), 203748_x_at (RNA binding motif, single stranded interacting protein 1), 223147_s_at (WD repeat domain 33), 213773_x_at (NOL/NOP2/Sun domain family, member 5), 1560049_at CUG triplet repeat, RNA binding protein 2), 243974_at (CDNA clone IMAGE:4821815), 201510_at E74-like factor 3 (ets domain transcription factor, epithelial specific), complementary sequences, fragments, alleles, variants, derivatives and/or gene products thereof.

In another preferred embodiment, prediction of prognosis of heart failure comprises detecting at least nine molecules having gene sequences comprising: 1558458_at (Hypothetical LOC401320), 1560049_at (CUG triplet repeat, RNA binding protein 2, CUGBP2), 201394_s_at (RNA binding motif protein 5, RBM5), 201655_s_at (heparan sulfate proteoglycan 2 (perlecan), HSPG2), 202379_s_at (natural killer-tumor recognition sequence, NKTR), 202808_at, 203071_at (sema domain, immunoglobulin domain (Ig), short basic domain, secreted, (semaphorin) 3B, SEMA3B), 203748_x_at (RNA binding motif, single stranded interacting protein 1, RBMS1), 203981_s_at (ATP-binding cassette, sub-family D (ALD), member 4, ABCD4), 204737_s_at (myosin, heavy chain 6, myosin, heavy chain 7, MYH6///MYH7), 204978_at (splicing factor, arginine/serine-rich 16, SFRS16), 206209_s_at (carbonic anhydrase IV, CA4), 207541_s_at (exosome component 10, EXOSC10), 207798_s_at (ataxin 2-like, ATXN2L), 208978_at (cysteine-rich protein 2, CRIP2), 209354_at (tumor necrosis factor receptor superfamily, member 14 TNFRSF14), 210628_x_at (latent transforming growth factor beta binding protein 4, LTBP4), 211909_x_at (prostaglandin E receptor 3 (subtype EP3), PTGER3), 211996_at (KIAA0220-like protein, nuclear pore complex (LOC23117), 212487_at (G patch domain containing 8, GPATCH8), 213946_s_at (obscurin-like 1, OBSL1), 214951_at (solute carrier family 26, member 10, SLC26A10), 220219_s_at (leucine rich repeat containing 37A, LRRC37A), 221071_at, 221780_s_at (DEAD (Asp-Glu-Ala-Asp) box polypeptide 27DDX27), 221806_s_at (SET domain containing 5, SETD5), 221833_at (Lon peptidase 2, peroxisomal, LONP2), 223546_x_at (LUC7-like (S. cerevisiae), LUC7L), 224260_at (CDNA clone IMAGE:4478733), 225562_at (AS p21 protein activator 3, RASA3), 226040_at (MRNA; cDNA DKFZp762N156 (from clone DKFZp762N156), 227968_at (Parkinson disease 7 domain containing 1, PDDC1), 228198_s_at (Mitochondrial ribosomal protein S9, MRPS9), 229830_at (Transcribed locus), 230683_at (CDNA: FLJ20892 fis, clone ADKA03430), 238185_at (RNA binding motif, single stranded interacting protein 1, RBMS1), 241597_at (Arginine-glutamic acid dipeptide (RE) repeats, RERE), 242551_at (Chromosome 18 open reading frame 1, C18orf1), 244208_at (Checkpoint suppressor 1, CHES1), 244494_at (Zinc finger, DHHC-type containing 1, ZDHHC1), and 244548_at (Rho GTPase activating protein 26, ARHGAP26) complementary sequences, fragments, alleles, variants, derivatives and/or gene products thereof.

In another preferred embodiment, a biochip composition comprising gene sequences: a biomarker comprises gene sequences: 232669_at (Hypoxia inducible factor 3, alpha subunit), 214951_at (solute carrier family 26, member 10), 243482_at (Epidermal growth factor receptor pathway substrate 15-like 1), 226210_s_at (maternally expressed 3), 232159_at (Epidermal growth factor receptor pathway substrate 15-like 1), 233026_s_at (PDZ domain containing), 211996_s_at (KIAA0220-like protein hypothetical gene LOC 283846), 243774_at (mucin 20, cell surface associated), 242551_at (Chromosome 18 open reading frame), 244548_at (Rho GTPase activating protein 26), 244208_at (Checkpoint suppressor 1), 239984_at (Sodium channel, voltage-gated, type VII, alpha), 230683_at (CDNA: FLJ20892 fis, clone ADKA03430), 214869_at (apolipoprotein L, 6), 241597_at (Arginine-glutamic acid dipeptide (RE) repeats), 235887_at (Smg-6 homolog, nonsense mediated mRNA decay factor (C. elegans)), 229957_at (transmembrane protein 91), 223546_x_at (LUC7L-like (S. cerevisiae)), 239567_at (Rho GTPase activating protein 10), 242194_at (Cullin 4A), 1558525_at (hypothetical protein LOC283901), 227178_at (CUG triplet repeat, RNA binding protein 2), 228198_s_at (Mitochondrial ribosomal protein S9), 202379_s_at (natural killer-tumor recognition sequence), 224260_at (CDNA clone), 238643_at (Neuroblastoma, suppression of tumorigenicity 1), 232253_at (RAD50 homolog (S. cerevisiae)), 227968_at (Parkinson disease 7 domain containing 1), 233197_at (kelch-like 9 (Drosophila)), 244512_at (transcribed locus strongly similar to XP_0010813421), 233443_at (hypothetical protein LOC389362), 231275_at (FLJ42875 protein), 226419_s_at (hypothetical protein LOC64546), 201221_s_at small nuclear ribonucleoprotein 70 kDa polypeptide), 209354_at (tumor necrosis factor receptor family member 14), 226571_s_at (protein tyrosine phosphatase receptor type, S), 220728_at (EST), 203071_at (sema domain, immunoglobulin domain (Ig), short basic domain), 213946_s_at obscurin-like 1, similar to titin isoform N2-B), 201394_s_at (RNA binding motif protein 5), 203748_x_at (RNA binding motif, single stranded interacting protein 1), 223147_s_at (WD repeat domain 33), 213773_x_at (NOL/NOP2/Sun domain family, member 5), 1560049_at CUG triplet repeat, RNA binding protein 2), 243974_at (CDNA clone IMAGE: 4821815), 201510_at E74-like factor 3 (ets domain transcription factor, epithelial specific), complementary sequences, fragments, alleles, variants, derivatives and/or gene products thereof.

In one embodiment, the biochip comprises at least ten biomolecules selected from a biomarker comprises gene sequences: 232669_at (Hypoxia inducible factor 3, alpha subunit), 214951_at (solute carrier family 26, member 10), 243482_at (Epidermal growth factor receptor pathway substrate 15-like 1), 226210_s_at (maternally expressed 3), 232159_at (Epidermal growth factor receptor pathway substrate 15-like 1), 233026_s_at (PDZ domain containing), 211996_s_at (KIAA0220-like protein hypothetical gene LOC 283846), 243774_at (mucin 20, cell surface associated), 242551_at (Chromosome 18 open reading frame), 244548_at (Rho GTPase activating protein 26), 244208_at (Checkpoint suppressor 1), 239984_at (Sodium channel, voltage-gated, type VII, alpha), 230683_at (CDNA: FLJ20892 fis, clone ADKA03430), 214869_at (apolipoprotein L, 6), 241597_at (Arginine-glutamic acid dipeptide (RE) repeats), 235887_at (Smg-6 homolog, nonsense mediated mRNA decay factor (C. elegans)), 229957_at (transmembrane protein 91), 223546_x_at (LUC7L-like (S. cerevisiae)), 239567_at (Rho GTPase activating protein 10), 242194_at (Cullin 4A), 1558525_at (hypothetical protein LOC283901), 227178_at (CUG triplet repeat, RNA binding protein 2), 228198_s_at (Mitochondrial ribosomal protein S9), 202379_s_at (natural killer-tumor recognition sequence), 224260_at (CDNA clone), 238643_at (Neuroblastoma, suppression of tumorigenicity 1), 232253_at (RAD50 homolog (S. cerevisiae)), 227968_at (Parkinson disease 7 domain containing 1), 233197_at (kelch-like 9 (Drosophila)), 244512_at (transcribed locus strongly similar to XP_0010813421), 233443_at (hypothetical protein LOC389362), 231275_at (FLJ42875 protein), 226419_s_at (hypothetical protein LOC64546), 201221_s_at small nuclear ribonucleoprotein 70 kDa polypeptide), 209354_at (tumor necrosis factor receptor family member 14), 226571_s_at (protein tyrosine phosphatase receptor type, S), 220728_at (EST), 203071_at (sema domain, immunoglobulin domain (Ig), short basic domain), 213946_s_at obscurin-like 1, similar to titin isoform N2-B), 201394_s_at (RNA binding motif protein 5), 203748_x_at (RNA binding motif, single stranded interacting protein 1), 223147_s_at (WD repeat domain 33), 213773_x_at (NOL/NOP2/Sun domain family, member 5), 1560049_at CUG triplet repeat, RNA binding protein 2), 243974_at (CDNA clone IMAGE: 4821815), 201510_at E74-like factor 3 (ets domain transcription factor, epithelial specific), complementary sequences, fragments, alleles, variants, derivatives and/or gene products thereof.

In another preferred embodiment, a biochip composition comprising gene sequences: a biomarker comprises gene sequences: 1558458_at (Hypothetical LOC401320), 1560049_at (CUG triplet repeat, RNA binding protein 2, CUGBP2), 201394_s_at (RNA binding motif protein 5, RBM5), 201655_s_at (heparan sulfate proteoglycan 2 (perlecan), HSPG2), 202379_s_at (natural killer-tumor recognition sequence, NKTR), 202808_at, 203071_at (sema domain, immunoglobulin domain (Ig), short basic domain, secreted, (semaphorin) 3B, SEMA3B), 203748_x_at (RNA binding motif, single stranded interacting protein 1, RBMS1), 203981_s_at (ATP-binding cassette; sub-family D (ALD), member 4, ABCD4), 204737_s_at (myosin, heavy chain 6, myosin, heavy chain 7, MYH6///MYH7), 204978_at (splicing factor, arginine/serine-rich 16, SFRS16), 206209_s_at (carbonic anhydrase IV, CA4), 207541_s_at (exosome component 10, EXOSC10), 207798_s_at (ataxin 2-like, ATXN2L), 208978_at (cysteine-rich protein 2, CRIP2), 209354_at (tumor necrosis factor receptor superfamily, member 14 TNFRSF14), 210628_x_at (latent transforming growth factor beta binding protein 4, LTBP4), 211909_x_at (prostaglandin E receptor 3 (subtype EP3), PTGER3), 211996_at (KIAA0220-like protein, nuclear pore complex (LOC23117), 212487_at (G patch domain containing 8, GPATCH8), 213946_s_at (obscurin-like 1, OBSL1), 214951_at (solute carrier family 26, member 10, SLC26A10), 220219_s_at (leucine rich repeat containing 37A, LRRC37A), 221071_at, 221780_s_at (DEAD (Asp-Glu-Ala-Asp) box polypeptide 27DDX27), 221806_s_at (SET domain containing 5, SETD5), 221833_at (Lon peptidase 2, peroxisomal, LONP2), 223546_x_at (LUC7-like (*S. cerevisiae*), LUC7L), 224260_at (CDNA clone IMAGE:4478733), 225562_at (AS p21 protein activator 3, RASA3), 226040_at (MRNA; cDNA DKFZp762N156 (from clone DKFZp762N156), 227968_at (Parkinson disease 7 domain containing 1, PDDC1), 228198_s_at (Mitochondrial ribosomal protein S9, MRPS9), 229830_at (Transcribed locus), 230683_at (CDNA: FLJ20892 fis, clone ADKA03430), 238185_at (RNA binding motif, single stranded interacting protein 1, RBMS1), 241597_at (Arginine-glutamic acid dipeptide (RE) repeats, RERE), 242551_at (Chromosome 18 open reading frame 1, C18orf1), 244208_at (Checkpoint suppressor 1, CHES1), 244494_at (Zinc finger, DHHC-type containing 1, ZDHHC1), and 244548_at (Rho GTPase activating protein 26, ARHGAP26) complementary sequences, fragments, alleles, variants, derivatives and/or gene products thereof.

In a preferred embodiment, a biochip comprises at least nine molecules comprising: 1558458_at (Hypothetical LOC401320), 1560049_at (CUG triplet repeat, RNA binding protein 2, CUGBP2), 201394_s_at (RNA binding motif protein 5, RBMS), 201655_s_at (heparan sulfate proteoglycan 2 (perlecan), HSPG2), 202379_s_at (natural killer-tumor recognition sequence, NKTR), 202808_at, 203071_at (sema domain, immunoglobulin domain (Ig), short basic domain, secreted, (semaphorin) 3B, SEMA3B), 203748_x_at (RNA binding motif, single stranded interacting protein 1, RBMS1), 203981_s_at (ATP-binding cassette, sub-family D (ALD), member 4, ABCD4), 204737_s_at (myosin, heavy chain 6, myosin, heavy chain 7, MYH6/// MYH7), 204978_at (splicing factor, arginine/serine-rich 16, SFRS16), 206209_s_at (carbonic anhydrase IV, CA4), 207541_s_at (exosome component 10, EXOSC10), 207798_s_at (ataxin 2-like, ATXN2L), 208978_at (cysteine-rich protein 2, CRIP2), 209354_at (tumor necrosis factor receptor superfamily, member 14 TNFRSF14), 210628_x_at (latent transforming growth factor beta binding protein 4, LTBP4), 211909_x_at (prostaglandin E receptor 3 (subtype EP3), PTGER3), 211996_at (KIAA0220-like protein, nuclear pore complex (LOC23117), 212487_at (G patch domain containing 8, GPATCH8), 213946_s_at (obscurin-like 1, OBSL1), 214951_at (solute carrier family 26, member 10, SLC26A10), 220219_s_at (leucine rich repeat containing 37A, LRRC37A), 221071_at, 221780_s_at (DEAD (Asp-Glu-Ala-Asp) box polypeptide 27DDX27), 221806_s_at (SET domain containing 5, SETD5), 221833_at (Lon peptidase 2, peroxisomal, LONP2), 223546_x_at (LUC7-like (*S. cerevisiae*), LUC7L), 224260_at (CDNA clone IMAGE:4478733), 225562_at (AS p21 protein activator 3, RASA3), 226040_at (MRNA; cDNA DKFZp762N156 (from clone DKFZp762N156), 227968_at (Parkinson disease 7 domain containing 1, PDDC1), 228198_s_at (Mitochondrial ribosomal protein S9, MRPS9), 229830_at (Transcribed locus), 230683_at (CDNA: FLJ20892 fis, clone ADKA03430), 238185_at (RNA binding motif, single stranded interacting protein 1, RBMS1), 241597_at (Arginine-glutamic acid dipeptide (RE) repeats, RERE), 242551_at (Chromosome 18 open reading frame 1, C18orf1), 244208_at (Checkpoint suppressor 1, CHES1), 244494_at (Zinc finger, DHHC-type containing 1, ZDHHC1), and 244548_at (Rho GTPase activating protein 26, ARHGAP26) complementary sequences, fragments, alleles, variants, derivatives and/or gene products thereof.

In another preferred embodiment, a method of predicting a prognosis of new onset heart failure, heart disease or conditions thereof comprising: identifying in a biological sample from a patient a biomarker comprising gene sequences: a biomarker comprises gene sequences: 232669_at (Hypoxia inducible factor 3, alpha subunit), 214951_at (solute carrier family 26, member 10), 243482_at (Epidermal growth factor receptor pathway substrate 15-like 1), 226210_s_at (maternally expressed 3), 232159_at (Epidermal growth factor receptor pathway substrate 15-like 1), 233026_s_at (PDZ domain containing), 211996_s_at (KIAA0220-like protein hypothetical gene LOC 283846), 243774_at (mucin 20, cell surface associated), 242551_at (Chromosome 18 open reading frame), 244548_at (Rho GTPase activating protein 26), 244208_at (Checkpoint suppressor 1), 239984_at (Sodium channel, voltage-gated, type VII, alpha), 230683_at (CDNA:FLJ20892 fis, clone ADKA03430), 214869_at (apolipoprotein L, 6), 241597_at (Arginine-glutamic acid dipeptide (RE) repeats), 235887_at (Smg-6 homolog, nonsense mediated mRNA decay factor (*C. elegans*)), 229957_at (transmembrane protein 91), 223546_x_at (LUC7L-like (*S. cerevisiae*)), 239567_at (Rho GTPase activating protein 10), 242194_at (Cullin 4A), 1558525_at (hypothetical protein LOC283901), 227178_at (CUG triplet repeat, RNA binding protein 2), 228198_s_at (Mitochondrial ribosomal protein S9), 202379_s_at (natural killer-tumor recognition sequence), 224260_at (CDNA clone), 238643_at (Neuroblastoma, suppression of tumorigenicity 1), 232253_at (RAD50 homolog (*S. cerevisiae*)), 227968_at (Parkinson disease 7 domain containing 1), 233197_at (kelch-like 9 (*Drosophila*)), 244512_at (transcribed locus strongly similar to XP 0010813421), 233443_at (hypothetical protein LOC389362), 231275_at (FLJ42875 protein), 226419_s_at (hypothetical protein LOC64546), 201221_s_at small nuclear ribonucleoprotein 70 kDa polypeptide), 209354_at (tumor necrosis factor receptor family member 14), 226571_s_at (protein tyrosine phosphatase receptor type, S), 220728_at (EST), 203071_at (sema domain, immunoglobulin domain (Ig), short basic domain), 213946_s_at obscurin-like 1, similar to titin isoform N2-B), 201394_s_at (RNA binding motif protein 5), 203748_x_at (RNA binding motif, single stranded interacting protein 1), 223147_s_at (WD repeat domain 33), 213773_x_at (NOL/NOP2/Sun domain family, member 5), 1560049_at CUG triplet repeat, RNA binding protein 2), 243974_at (CDNA clone IMAGE:4821815), 201510_at E74-like factor 3 (ets domain transcription factor, epithelial specific), complementary sequences, fragments, alleles, variants, derivatives and/or gene products thereof; and, assessing the probability of identification of each component gene in each sample; and assigning each to a class. An example of a preferred method is detailed in the examples which follow.

In another preferred embodiment, a method of identifying and distinguishing between patients at a high risk of heart disease and patients with a good prognosis for recovery comprising: identifying a biomarker comprising gene sequences comprising: a biomarker comprises gene sequences: 232669_at (Hypoxia inducible factor 3, alpha subunit), 214951_at (solute carrier family 26, member 10), 243482_at (Epidermal growth factor receptor pathway substrate 15-like 1), 226210_s_at (maternally expressed 3), 232159_at (Epidermal growth factor receptor pathway substrate 15-like 1), 233026_s_at (PDZ domain containing), 211996_s_at (KIAA0220-like protein hypothetical gene LOC 283846), 243774_at (mucin 20, cell surface associated), 242551_at (Chromosome 18 open reading frame), 244548_at (Rho GTPase activating protein 26), 244208_at (Checkpoint suppressor 1), 239984_at (Sodium channel, voltage-gated, type VII, alpha), 230683_at (CDNA: FLJ20892 fis, clone ADKA03430), 214869_at (apolipoprotein L, 6), 241597_at (Arginine-glutamic acid dipeptide (RE) repeats), 235887_at (Smg-6 homolog, nonsense mediated mRNA decay factor (*C. elegans*)), 229957_at (transmembrane protein 91), 223546_x_at (LUC7L-like (*S. cerevisiae*)), 239567_at (Rho GTPase activating protein 10), 242194_at (Cullin 4A), 1558525_at (hypothetical protein LOC283901), 227178_at (CUG triplet repeat, RNA binding protein 2), 228198_s_at (Mitochondrial ribosomal protein S9), 202379_s_at (natural killer-tumor recognition sequence), 224260_at (CDNA clone), 238643_at (Neuroblastoma, suppression of tumorigenicity 1), 232253_at (RAD50 homolog (*S. cerevisiae*)), 227968_at (Parkinson disease 7 domain containing 1), 233197_at (kelch-like 9 (*Drosophila*)), 244512_at (transcribed locus strongly similar to XP_0010813421), 233443_at (hypothetical protein LOC389362), 231275_at (FLJ42875 protein), 226419_s_at (hypothetical protein LOC64546), 201221_s_at small nuclear ribonucleoprotein 70 kDa polypeptide), 209354_at (tumor necrosis factor receptor family member 14), 226571_s_at (protein tyrosine phosphatase receptor type, S), 220728_at (EST), 203071_at (sema domain, immunoglobulin domain (Ig), short basic domain), 213946_s_at obscurin-like 1, similar to titin isoform N2-B), 201394_s_at (RNA binding motif protein 5), 203748_x_at (RNA binding motif, single stranded interacting protein 1), 223147_s_at (WD repeat domain 33), 213773_x_at (NOL/NOP2/Sun domain family, member 5), 1560049_at CUG triplet repeat, RNA binding protein 2), 243974_at (CDNA clone IMAGE: 4821815), 201510_at E74-like factor 3 (ets domain transcription factor, epithelial specific), complementary sequences, fragments, alleles, variants, derivatives and/or gene products thereof; assessing the probability of identification of each component gene in each sample; assigning each to a class; and, identifying and distinguishing between patients at a high risk of heart disease and patients with a good prognosis for recovery.

In another preferred embodiment, a method of identifying and distinguishing between patients at a high risk of heart disease and patients with a good prognosis for recovery comprising: identifying a biomarker comprising gene sequences comprising: a biomarker comprises gene sequences: 1558458_at (Hypothetical LOC401320), 1560049_at (CUG triplet repeat, RNA binding protein 2, CUGBP2), 201394_s_at (RNA binding motif protein 5, RBM5), 201655_s_at (heparan sulfate proteoglycan 2 (perlecan), HSPG2), 202379_s_at (natural killer-tumor recognition sequence, NKTR), 202808_at, 203071_at (sema domain, immunoglobulin domain (Ig), short basic domain, secreted, (semaphorin) 3B, SEMA3B), 203748_x_at (RNA binding motif, single stranded interacting protein 1, RBMS1), 203981_s_at (ATP-binding cassette, sub-family D (ALD), member 4, ABCD4), 204737_s_at (myosin, heavy chain 6, myosin, heavy chain 7, MYH6///MYH7), 204978_at (splicing factor, arginine/serine-rich 16, SFRS16), 206209_s_at (carbonic anhydrase IV, CA4), 207541_s_at (exosome component 10, EXOSC10), 207798_s_at (ataxin 2-like, ATXN2L), 208978_at (cysteine-rich protein 2, CRIP2), 209354_at (tumor necrosis factor receptor superfamily, member 14 TNFRSF14), 210628_x_at (latent transforming growth factor beta binding protein 4, LTBP4), 211909_x_at (prostaglandin E receptor 3 (subtype EP3), PTGER3), 211996_at (KIAA0220-like protein, nuclear pore complex (LOC23117), 212487_at (G patch domain containing 8, GPATCH8), 213946_s_at (obscurin-like 1, OBSL1), 214951_at (solute carrier family 26, member 10, SLC26A10), 220219_s_at (leucine rich repeat containing 37A, LRRC37A), 221071_at, 221780_s_at (DEAD (Asp-Glu-Ala-Asp) box polypeptide 27DDX27), 221806_s_at (SET domain containing 5, SETD5), 221833_at (Lon peptidase 2, peroxisomal, LONP2), 223546_x_at (LUC7-like (*S. cerevisiae*), LUC7L), 224260_at (CDNA clone IMAGE:4478733), 225562_at (AS p21 protein activator 3, RASA3), 226040_at (MRNA; cDNA DKFZp762N156 (from clone DKFZp762N156), 227968_at (Parkinson disease 7 domain containing 1, PDDC1), 228198_s_at (Mitochondrial ribosomal protein S9, MRPS9), 229830_at (Transcribed locus), 230683_at (CDNA: FLJ20892 fis, clone ADKA03430), 238185_at (RNA binding motif, single stranded interacting protein 1, RBMS1), 241597_at (Arginine-glutamic acid dipeptide (RE) repeats, RERE), 242551_at (Chromosome 18 open reading frame 1, C18orf1), 244208_at (Checkpoint suppressor 1, CHES1), 244494_at (Zinc finger, DHHC-type containing 1, ZDHHC1), and 244548_at (Rho GTPase activating protein 26, ARHGAP26) complementary sequences, fragments, alleles, variants, derivatives and/or gene products thereof.

Alternative Methods and Materials for Identifying Molecular Signatures or Transcriptomic Biomarkers Detection of Nucleic Acids and Proteins as Markers: In preferred embodiments, each biomarker is detected on chip based methods such as those described in detail in the examples which follow. In order to provide accurate prognosis and diagnosis of heart failure patients with good prognostic outcome, cardiac disorders and diseases, for example, heart failure, myocarditis, idiopathic cardiomyopathy and the like. Other methods are also known in the art and one or more methods can be utilized.

The methods and assays disclosed herein are directed to the examination of expression of transcriptomic biomarkers in a mammalian tissue or cell sample, wherein the determination of that expression of one or more such transcriptomic biomarkers is predictive of prognostic outcome or diagnostic of cardiac and cardiovascular diseases and disorders, such as for example, myocarditis, Coronary Heart Disease, angina, Acute Coronary Syndrome, Aortic Aneurysm and Dissection, arrhythmias, Cardiomyopathy, Congenital Heart Disease, congestive heart failure or chronic heart failure, pericarditis, and the like. The Molecular signatures or Transcriptomic biomarker comprise the biomolecules identified in Table 2. As more biomolecules are discovered, each newly identified biomolecules can be assigned to any one or more biomarker or molecular signature. Each biomolecule can also be removed, reassigned or reallocated to a molecular signature.

Preferred embodiments in the identification of biomolecules, analytical methods etc, are described in detail in the Examples which follow.

Microarrays: In general, using nucleic acid microarrays, test and control mRNA samples from test and control tissue samples are reverse transcribed and labeled to generate cDNA probes. The probes are then hybridized to an array of nucleic acids immobilized on a solid support. The array is configured such that the sequence and position of each member of the array is known. For example, a selection of genes that have potential to be expressed in certain disease states may be arrayed on a solid support. Hybridization of a labeled probe with a particular array member indicates that the sample from which the probe was derived expresses that gene. Differential gene expression analysis of disease tissue can provide valuable information. Microarray technology utilizes nucleic acid hybridization techniques and computing technology to evaluate the mRNA expression profile of thousands of genes within a single experiment. (see, e.g., WO 01/75166 published Oct. 11, 2001; (See, for example, U.S. Pat. No. 5,700,637, U.S. Pat. No. 5,445,934, and U.S. Pat. No. 5,807,522, Lockart, *Nature Biotechnology*, 14:1675-1680 (1996); Cheung, V. G. et al., *Nature Genetics* 21(Suppl):15-19 (1999) for a discussion of array fabrication). DNA microarrays are miniature arrays containing gene fragments that are either synthesized directly onto or spotted onto glass or other substrates. Thousands of genes are usually represented in a single array. A typical microarray experiment involves the following steps: 1) preparation of fluorescently labeled target from RNA isolated from the sample, 2) hybridization of the labeled target to the microarray, 3) washing, staining, and scanning of the array, 4) analysis of the scanned image and 5) generation of gene expression profiles. Currently two main types of DNA microarrays are being used: oligonucleotide (usually 25 to 70 mers) arrays and gene expression arrays containing PCR products prepared from cDNAs. In forming an array, oligonucleotides can be either prefabricated and spotted to the surface or directly synthesized on to the surface (in situ). The Affymetrix GeneChip™ system is a commercially available microarray system which comprises arrays fabricated by direct synthesis of oligonucleotides on a glass surface.

Probe/Gene Arrays:

Oligonucleotides, usually 25 mers, are directly synthesized onto a glass wafer by a combination of semiconductor-based photolithography and solid phase chemical synthesis technologies. Each array contains up to 400,000 different oligonucleotides and each oligonucleotide is present in millions of copies. Since oligonucleotide probes are synthesized in known locations on the array, the hybridization patterns and signal intensities can be interpreted in terms of gene identity and relative expression levels by the Affymetrix Microarray Suite software. Each gene is represented on the array by a series of different oligonucleotide probes. Each probe pair consists of a perfect match oligonucleotide and a mismatch oligonucleotide. The perfect match probe has a sequence exactly complimentary to the particular gene and thus measures the expression of the gene. The mismatch probe differs from the perfect match probe by a single base substitution at the center base position, disturbing the binding of the target gene transcript. This helps to determine the background and nonspecific hybridization that contributes to the signal measured for the perfect match oligonucleotide. The Microarray Suite software subtracts the hybridization intensities of the mismatch probes from those of the perfect match probes to determine the absolute or specific intensity value for each probe set. Probes are chosen based on current information from GenBank and other nucleotide repositories. The sequences are believed to recognize unique regions of the 3' end of the gene. A GeneChip Hybridization Oven ("rotisserie" oven) is used to carry out the hybridization of up to 64 arrays at one time. The fluidics station performs washing and staining of the probe arrays. It is completely automated and contains four modules, with each module holding one probe array. Each module is controlled independently through Microarray Suite software using preprogrammed fluidics protocols. The scanner is a confocal laser fluorescence scanner which measures fluorescence intensity emitted by the labeled cRNA bound to the probe arrays. The computer workstation with Microarray Suite software controls the fluidics station and the scanner. Microarray Suite software can control up to eight fluidics stations using preprogrammed hybridization, wash, and stain protocols for the probe array. The software also acquires and converts hybridization intensity data into a presence/absence call for each gene using appropriate algorithms. Finally, the software detects changes in gene expression between experiments by comparison analysis and formats the output into .txt files, which can be used with other software programs for further data analysis.

The expression of a selected biomarker may also be assessed by examining gene deletion or gene amplification. Gene deletion or amplification may be measured by any one of a wide variety of protocols known in the art, for example, by conventional Southern blotting, Northern blotting to quantitate the transcription of mRNA (Thomas, *Proc. Natl. Acad. Sci. USA,* 77:5201-5205 (1980)), dot blotting (DNA analysis), or in situ hybridization (e.g., FISH), using an appropriately labeled probe, cytogenetic methods or comparative genomic hybridization (CGH) using an appropriately labeled probe.

Detection of Polypeptides:

In another embodiment of the present invention, a polypeptide corresponding to a marker is detected. A preferred agent for detecting a polypeptide of the invention is an antibody or aptamer capable of binding to a polypeptide corresponding to a marker of the invention, preferably an antibody with a detectable label. Antibodies can be polyclonal, or more preferably, monoclonal. An intact antibody, or a fragment thereof, e.g., Fab or F(ab') 2 can be used. The term "labeled", with regard to the probe or antibody, is intended to encompass direct-labeling of the probe or antibody by coupling, i.e., physically linking, a detectable substance to the probe or antibody, as well as indirect-labeling of the probe or antibody by reactivity with another reagent that is directly-labeled. Examples of indirect labeling include detection of a primary antibody using a fluorescently-labeled secondary antibody and end-labeling of a DNA probe with biotin such that it can be detected with fluorescently-labeled streptavidin.

Proteins from individuals can be isolated using techniques that are well-known to those of skill in the art. The protein isolation methods employed can, e.g., be such as those described in Harlow & Lane (1988), supra. A variety of formats can be employed to determine whether a sample contains a protein that binds to a given antibody. Expression of various biomarkers in a sample can be analyzed by a number of methodologies, many of which are known in the art and understood by the skilled artisan, including but not limited to, immunohistochemical and/or Western analysis, quantitative blood based assays (as for example Serum ELISA) (to examine, for example, levels of protein expression), biochemical enzymatic activity assays, in situ hybridization, Northern analysis and/or PCR analysis of mRNAs, as well as any one of the wide variety of assays that can be performed by gene and/or tissue array analysis. Typical protocols for evaluating the status of genes and gene products are found, for example in Ausubel et al. eds., 1995, Current Protocols In Molecular Biology, Units 2 (Northern Blotting), 4 (Southern Blotting), 15 (Immunoblotting) and 18 (PCR Analysis). A skilled artisan can readily adapt known protein/antibody detection methods for use in determining whether cells express a marker of the present invention and the relative concentration of that specific polypeptide expression product in blood or other body tissues.

In such alternative methods, a sample may be contacted with an antibody specific for said biomarker under conditions sufficient for an antibody-biomarker complex to form, and then detecting said complex. The presence of the biomarker may be detected in a number of ways, such as by Western blotting and ELISA procedures for assaying a wide variety of tissues and samples, including plasma or serum. A wide range of immunoassay techniques using such an assay format are available, see, e.g., U.S. Pat. Nos. 4,016,043, 4,424,279 and 4,018,653. These include both single-site and two-site or "sandwich" assays of the non-competitive types, as well as in the traditional competitive binding assays. These assays also include direct binding of a labeled antibody to a target biomarker.

Sandwich assays are among the most useful and commonly used assays. A number of variations of the sandwich assay technique exist, and all are intended to be encompassed by the present invention. Briefly, in a typical forward assay, an unlabelled antibody is immobilized on a solid substrate, and the sample to be tested brought into contact with the bound molecule. After a suitable period of incubation, for a period of time sufficient to allow formation of an antibody-antigen complex, a second antibody specific to the antigen, labeled with a reporter molecule capable of producing a detectable signal is then added and incubated, allowing time sufficient for the formation of another complex of antibody-antigen-labeled antibody. Any unreacted material is washed away, and the presence of the antigen is determined by observation of a signal produced by the reporter molecule. The results may either be qualitative, by simple observation of the visible signal, or may be quantitated by comparing with a control sample containing known amounts of biomarker.

Variations on the forward assay include a simultaneous assay, in which both sample and labeled antibody are added simultaneously to the bound antibody. These techniques are well known to those skilled in the art, including any minor variations as will be readily apparent. In a typical forward sandwich assay, a first antibody having specificity for the biomarker is either covalently or passively bound to a solid surface. The solid surface is typically glass or a polymer, the most commonly used polymers being cellulose, polyacrylamide, nylon, polystyrene, polyvinyl chloride or polypropylene. The solid supports may be in the form of tubes, beads, discs of microplates, or any other surface suitable for conducting an immunoassay. The binding processes are well-known in the art and generally consist of cross-linking covalently binding or physically adsorbing, the polymer-antibody complex is washed in preparation for the test sample. An aliquot of the sample to be tested is then added to the solid phase complex and incubated for a period of time sufficient (e.g. 2-40 minutes or overnight if more convenient) and under suitable conditions (e.g. from room temperature to 40° C. such as between 25° C. and 32° C. inclusive) to allow binding of any subunit present in the antibody. Following the incubation period, the antibody subunit solid phase is washed and dried and incubated with a second antibody specific for a portion of the biomarker. The second antibody is linked to a reporter molecule which is used to indicate the binding of the second antibody to the molecular marker.

An alternative method involves immobilizing the target biomarkers in the sample and then exposing the immobilized target to specific antibody which may or may not be labeled with a reporter molecule. Depending on the amount of target and the strength of the reporter molecule signal, a bound target may be detectable by direct labeling with the antibody. Alternatively, a second labeled antibody, specific to the first antibody is exposed to the target-first antibody complex to form a target-first antibody-second antibody tertiary complex. The complex is detected by the signal emitted by the reporter molecule. By "reporter molecule", as used in the present specification, is meant a molecule which, by its chemical nature, provides an analytically identifiable signal which allows the detection of antigen-bound antibody. The most commonly used reporter molecules in this type of assay are either enzymes, fluorophores or radionuclide containing molecules (i.e. radioisotopes) and chemiluminescent molecules.

In the case of an enzyme immunoassay, an enzyme is conjugated to the second antibody, generally by means of glutaraldehyde or periodate. As will be readily recognized, however, a wide variety of different conjugation techniques exist, which are readily available to the skilled artisan. Commonly used enzymes include horseradish peroxidase, glucose oxidase, -galactosidase and alkaline phosphatase, amongst others. The substrates to be used with the specific enzymes are generally chosen for the production, upon hydrolysis by the corresponding enzyme, of a detectable color change. Examples of suitable enzymes include alkaline phosphatase and peroxidase. It is also possible to employ fluorogenic substrates, which yield a fluorescent product rather than the chromogenic substrates noted above. In all cases, the enzyme-labeled antibody is added to the first antibody-molecular marker complex, allowed to bind, and then the excess reagent is washed away. A solution containing the appropriate substrate is then added to the complex of antibody-antigen-antibody. The substrate will react with the enzyme linked to the second antibody, giving a qualitative visual signal, which may be further quantitated, usually spectrophotometrically, to give an indication of the amount of biomarker which was present in the sample. Alternately, fluorescent compounds, such as fluorescein and rhodamine, may be chemically coupled to antibodies without altering their binding capacity. When activated by illumination with light of a particular wavelength, the fluorochrome-labeled antibody adsorbs the light energy, inducing a state to excitability in the molecule, followed by emission of the light at a characteristic color visually detectable with a light microscope. As in the EIA, the fluorescent labeled antibody is allowed to bind to the first antibody-molecular marker complex. After washing off the unbound reagent, the remaining tertiary complex is then exposed to the light of the appropriate wavelength, the fluorescence observed indicates the presence of the molecular marker of interest Immunofluorescence and EIA techniques are both very well established in the art. However, other reporter molecules, such as radioisotope, chemiluminescent or bioluminescent molecules, may also be employed.

Methods of the invention further include protocols which examine the presence and/or expression of mRNAs, in a tissue or cell sample. Methods for the evaluation of mRNAs in cells are well known and include, for example, hybridization assays using complementary DNA probes (such as in situ hybridization using labeled riboprobes, Northern blot and related techniques) and various nucleic acid amplification assays (such as RT-PCR and other amplification type detection methods, such as, for example, branched DNA, SISBA, TMA and the like).

In an embodiment, the level of mRNA corresponding to the marker can be determined both by in situ and by in vitro formats in a biological sample using methods known in the art. Many expression detection methods use isolated RNA. For in vitro methods, any RNA isolation technique that does not select against the isolation of mRNA can be utilized for the purification of RNA from cells. See, e.g., Ausubel et al., Ed., Curr. Prot. Mol. Biol., John Wiley & Sons, NY (1987-1999). Additionally, large numbers of tissue samples can readily be processed using techniques well-known to those of skill in the art, such as, e.g., the single-step RNA isolation process of U.S. Pat. No. 4,843,155. The isolated mRNA can be used in hybridization or amplification assays that include, but are not limited to, Southern or Northern analyses, PCR analyses and probe arrays. One preferred diagnostic method for the detection of mRNA levels involves contacting the isolated mRNA with a nucleic acid molecule (probe) that can hybridize to the mRNA encoded by the gene being detected. The nucleic acid probe can be, e.g., a full-length cDNA, or a portion thereof, such as an oligonucleotide of at least 7, 15, 30, 50, 100, 250 or 500 nucleotides in length and sufficient to specifically hybridize under stringent conditions to a mRNA or genomic DNA encoding a marker of the present invention. Other suitable probes for use in the diagnostic assays of the invention are described herein. Hybridization of an mRNA with the probe indicates that the marker in question is being expressed.

In one format, the mRNA is immobilized on a solid surface and contacted with a probe, for example, by running the isolated mRNA on an agarose gel and transferring the mRNA from the gel to a membrane, such as nitrocellulose. In an alternative format, the probe(s) are immobilized on a solid surface and the mRNA is contacted with the probe(s), for example, in an Affymetrix gene chip array. A skilled artisan can readily adapt known mRNA detection methods for use in detecting the level of mRNA encoded by the markers of the present invention.

Although amplification of molecules is not required in the present invention as discussed in the examples section, one of skill in the art could use amplification methods. One alternative method for determining the level of mRNA corresponding to a marker of the present invention in a sample involves the process of nucleic acid amplification, e.g., by RT-PCR (the experimental embodiment set forth in Mullis, U.S. Pat. No. 4,683,202 (1987); ligase chain reaction, self-sustained sequence replication, Guatelli et al., Proc. Natl. Acad. Sci. USA, Vol. 87, pp. 1874-1878 (1990); transcriptional amplification system, Kwoh et al., Proc. Natl. Acad. Sci. USA, Vol. 86, pp. 1173-1177 (1989); Q-Beta Replicase, Lizardi et al., Biol. Technology, Vol. 6, p. 1197 (1988); rolling circle replication, U.S. Pat. No. 5,854,033 (1988); or any other nucleic acid amplification method, followed by the detection of the amplified molecules using techniques well-known to those of skill in the art. These detection schemes are especially useful for the detection of the nucleic acid molecules if such molecules are present in very low numbers. As used herein, amplification primers are defined as being a pair of nucleic acid molecules that can anneal to 5' or 3' regions of a gene (plus and minus strands, respectively, or vice-versa) and contain a short region in between. In general, amplification primers are from about 10-30 nucleotides in length and flank a region from about 50-200 nucleotides in length. Under appropriate conditions and with appropriate reagents, such primers permit the amplification of a nucleic acid molecule comprising the nucleotide sequence flanked by the primers.

For in situ methods, mRNA does not need to be isolated form the cells prior to detection. In such methods, a cell or tissue sample is prepared/processed using known histological methods. The sample is then immobilized on a support, typically a glass slide, and then contacted with a probe that can hybridize to mRNA that encodes the marker.

As an alternative to making determinations based on the absolute expression level of the marker, determinations may be based on the normalized expression level of the marker. Expression levels are normalized by correcting the absolute expression level of a marker by comparing its expression to the expression of a gene that is not a marker, e.g., a housekeeping gene that is constitutively expressed. Suitable genes for normalization include housekeeping genes, such as the actin gene or epithelial cell-specific genes. This normalization allows the comparison of the expression level in one sample, e.g., a patient sample, to another sample or between samples from different sources.

Alternatively, the expression level can be provided as a relative expression level. To determine a relative expression level of a marker, the level of expression of the marker is determined for 10 or more samples of normal versus disease biological samples, preferably 50 or more samples, prior to the determination of the expression level for the sample in question. The mean expression level of each of the genes assayed in the larger number of samples is determined and this is used as a baseline expression level for the marker. The expression level of the marker determined for the test sample (absolute level of expression) is then divided by the mean expression value obtained for that marker. This provides a relative expression level.

Preferably, the samples used in the baseline determination will be from patients who do not have the polyrhorphism. The choice of the cell source is dependent on the use of the relative expression level. Using expression found in normal tissues as a mean expression score aids in validating whether the marker assayed is specific (versus normal cells). In addition, as more data is accumulated, the mean expression value can be revised, providing improved relative expression values based on accumulated data.

Antibodies and Aptamers

In a preferred embodiment, the antibodies and aptamers specifically bind each component of the biomarkers described herein. The components include the nucleic acid sequences, complementary sequences, fragments, alleles, variants, derivatives and/or gene products thereof of each component in each biomarker.

Aptamer polynucleotides are typically single-stranded standard phosphodiester DNA (ssDNA). Close DNA analogs can also be incorporated into the aptamer as described below.

A typical aptamer discovery procedure is described below:

A polynucleotide comprising a randomized sequence between "arms" having constant sequence is synthesized. The arms can include restriction sites for convenient cloning and can also function as priming sites for PCR primers. The synthesis can easily be performed on commercial instruments.

The target protein is treated with the randomized polynucleotide. The target protein can be in solution and then the complexes immobilized and separated from unbound nucleic acids by use of an antibody affinity column. Alternatively, the target protein might be immobilized before treatment with the randomized polynucleotide.

The target protein-polynucleotide complexes are separated from the uncomplexed material and then the bound polynucleotides are separated from the target protein. The bound nucleic acid can then be characterized, but is more commonly amplified, e.g. by PCR and the binding, separation and amplification steps are repeated. In many instances, use of conditions increasingly promoting separation of the nucleic acid from the target protein, e.g. higher salt concentration, in the binding buffer used in step 2) in subsequent iterations, results in identification of polynucleotides having increasingly high affinity for the target protein.

The nucleic acids showing high affinity for the target proteins are isolated and characterized. This is typically accomplished by cloning the nucleic acids using restriction sites incorporated into the arms, and then sequencing the cloned nucleic acid.

The affinity of aptamers for their target proteins is typically in the nanomolar range, but can be as low as the picomolar range. That is $K_D$ is typically 1 pM to 500 nM, more typically from 1 pM to 100 nM. Apatmers having an affinity of $K_D$ in the range of 1 pM to 10 nM are also useful.

Aptamer polynucleotides can be synthesized on a commercially available nucleic acid synthesizer by methods known in the art. The product can be purified by size selection or chromatographic methods.

Aptamer polynucleotides are typically from about 10 to 200 nucleotides long, more typically from about 10 to 100 nucleotides long, still more typically from about 10 to 50 nucleotides long and yet more typically from about 10 to 25 nucleotides long. A preferred range of length is from about 10 to 50 nucleotides.

The aptamer sequences can be chosen as a desired sequence, or random or partially random populations of sequences can be made and then selected for specific binding to a desired target protein by assay in vitro. Any of the typical nucleic acid-protein binding assays known in the art can be used, e.g. "Southwestern" blotting using either labeled oligonucleotide or labeled protein as the probe. See also U.S. Pat. No. 5,445,935 for a fluorescence polarization assay of protein-nucleic acid interaction.

Appropriate nucleotides for aptamer synthesis and their use, and reagents for covalent linkage of proteins to nucleic acids and their use, are considered known in the art.

A desired aptamer-protein complex, for example, aptamer-thrombin complex of the invention can be labeled and used as a diagnostic agent in vitro in much the same manner as any specific protein-binding agent, e.g. a monoclonal antibody. Thus, an aptamer-protein complex of the invention can be used to detect and quantitate the amount of its target protein in a sample, e.g. a blood sample, to provide diagnosis of a disease state correlated with the amount of the protein in the sample.

A desired aptamer-target/bait molecular complex can also be used for diagnostic imaging. In imaging uses, the complexes are labeled so that they can be detected outside the body. Typical labels are radioisotopes, usually ones with short half-lives. The usual imaging radioisotopes, such as $^{123}I$, $^{124}I$, $^{125}I$, $^{131}I$, $^{99m}TC$, $^{186}Re$, $^{188}Re$, $^{64}Cu$, $^{67}Cu$, $^{212}Bi$, $^{213}Bi$, $^{67}Ga$, $^{90}Y$, hu $^{111}In$, $^{18}F$, $^{3}H$, $^{14}C$, $^{35}S$ or $^{32}P$ can be used. Nuclear magnetic resonance (NMR) imaging enhancers, such as gadolinium-153, can also be used to label the complex for detection by NMR. Methods and reagents for performing the labeling, either in the polynucleotide or in the protein moiety, are considered known in the art.

In a preferred embodiment, an antibody or aptamer is specific for each gene sequence of the biomarker comprising a biomarker comprises gene sequences: 232669_at (Hypoxia inducible factor 3, alpha subunit), 214951_at (solute carrier family 26, member 10), 243482_at (Epidermal growth factor receptor pathway substrate 15-like 1), 226210_s_at (maternally expressed 3), 232159_at (Epidermal growth factor receptor pathway substrate 15-like 1), 233026_s_at (PDZ domain containing), 211996_s_at (KIAA0220-like protein hypothetical gene LOC 283846), 243774_at (mucin 20, cell surface associated), 242551_at (Chromosome 18 open reading frame), 244548_at (Rho GTPase activating protein 26), 244208_at (Checkpoint suppressor 1), 239984_at (Sodium channel, voltage-gated, type VII, alpha), 230683_at (CDNA:FLJ20892 fis, clone ADKA03430), 214869_at (apolipoprotein L, 6), 241597_at (Arginine-glutamic acid dipeptide (RE) repeats), 235887_at (Smg-6 homolog, nonsense mediated mRNA decay factor (*C. elegans*)), 229957_at (transmembrane protein 91), 223546_x_at (LUC7L-like (*S. cerevisiae*)), 239567_at (Rho GTPase activating protein 10), 242194_at (Cullin 4A), 1558525_at (hypothetical protein LOC283901), 227178_at (CUG triplet repeat, RNA binding protein 2), 228198_s_at (Mitochondrial ribosomal protein S9), 202379_s_at (natural killer-tumor recognition sequence), 224260_at (CDNA clone), 238643_at (Neuroblastoma, suppression of tumorigenicity 1), 232253_at (RAD50 homolog (*S. cerevisiae*)), 227968_at (Parkinson disease 7 domain containing 1), 233197_at (kelch-like 9 (*Drosophila*)), 244512_at (transcribed locus strongly similar to XP 0010813421), 233443_at (hypothetical protein LOC389362), 231275_at (FLJ42875 protein), 226419_s_at (hypothetical protein LOC64546), 201221_s_at small nuclear ribonucleoprotein 70 kDa polypeptide), 209354_at (tumor necrosis factor receptor family member 14), 226571_s_at (protein tyrosine phosphatase receptor type, S), 220728_at (EST), 203071_at (sema domain, immunoglobulin domain (Ig), short basic domain), 213946_s_at obscurin-like 1, similar to titin isoform N2-B), 201394_s_at (RNA binding motif protein 5), 203748_x_at (RNA binding motif, single stranded interacting protein 1), 223147_s_at (WD repeat domain 33), 213773_x_at (NOL/NOP2/Sun domain family, member 5), 1560049_at CUG triplet repeat, RNA binding protein 2), 243974_at (CDNA clone IMAGE:4821815), 201510_at E74-like factor 3 (ets domain transcription factor, epithelial specific), complementary sequences, fragments, alleles, variants, derivatives and/or gene products thereof.

In a preferred embodiment, an antibody or aptamer is specific for each gene sequence of the biomarker comprising a biomarker comprises gene sequences: 1558458_at (Hypothetical LOC401320), 1560049_at (CUG triplet repeat, RNA binding protein 2, CUGBP2), 201394_s_at (RNA binding motif protein 5, RBMS), 201655_s_at (heparan sulfate proteoglycan 2 (perlecan), HSPG2), 202379_s_at (natural killer-tumor recognition sequence, NKTR), 202808_at, 203071_at (sema domain, immunoglobulin domain (Ig), short basic domain, secreted, (semaphorin) 3B, SEMA3B), 203748_x_at (RNA binding motif, single stranded interacting protein 1, RBMS1), 203981_s_at (ATP-binding cassette, sub-family D (ALD), member 4, ABCD4), 204737_s_at (myosin, heavy chain 6, myosin, heavy chain 7, MYH6///MYH7), 204978_at (splicing factor, arginine/serine-rich 16, SFRS16), 206209_s_at (carbonic anhydrase IV, CA4), 207541_s_at (exosome component 10, EXOSC10), 207798_s_at (ataxin 2-like, ATXN2L), 208978_at (cysteine-rich protein 2, CRIP2), 209354_at (tumor necrosis factor receptor superfamily, member 14

TNFRSF14), 210628_x_at (latent transforming growth factor beta binding protein 4, LTBP4), 211909_x_at (prostaglandin E receptor 3 (subtype EP3), PTGER3), 211996_at (KIAA0220-like protein, nuclear pore complex (LOC23117), 212487_at (G patch domain containing 8, GPATCH8), 213946_s_at (obscurin-like 1, OBSL1), 214951_at (solute carrier family 26, member 10, SLC26A10), 220219_s_at (leucine rich repeat containing 37A, LRRC37A), 221071_at, 221780_s_at (DEAD (Asp-Glu-Ala-Asp) box polypeptide 27DDX27), 221806_s_at (SET domain containing 5, SETD5), 221833_at (Lon peptidase 2, peroxisomal, LONP2), 223546_x_at (LUC7-like (S. cerevisiae), LUC7L), 224260_at (CDNA clone IMAGE: 4478733), 225562_at (AS p21 protein activator 3, RASA3), 226040_at (MRNA; cDNA DKFZp762N156 (from clone DKFZp762N156), 227968_at (Parkinson disease 7 domain containing 1, PDDC1), 228198_s_at (Mitochondrial ribosomal protein S9, MRPS9), 229830_at (Transcribed locus), 230683_at (CDNA: FLJ20892 fis, clone ADKA03430), 238185_at (RNA binding motif, single stranded interacting protein 1, RBMS1), 241597_at (Arginine-glutamic acid dipeptide (RE) repeats, RERE), 242551_at (Chromosome 18 open reading frame 1, C18orf1), 244208_at (Checkpoint suppressor 1, CHES1), 244494_at (Zinc finger, DHHC-type containing 1, ZDHHC1), and 244548_at (Rho GTPase activating protein 26, ARHGAP26) complementary sequences, fragments, alleles, variants, derivatives and/or gene products thereof.

Drug Discovery

In other preferred embodiments, the molecular signatures are useful for the identification of new drugs in the treatment of cardiovascular diseases and disorders.

Small Molecules:

Small molecule test compounds or candidate therapeutic compounds can initially be members of an organic or inorganic chemical library. As used herein, "small molecules" refers to small organic or inorganic molecules of molecular weight below about 3,000 Daltons. The small molecules can be natural products or members of a combinatorial chemistry library. A set of diverse molecules should be used to cover a variety of functions such as charge, aromaticity, hydrogen bonding, flexibility, size, length of side chain, hydrophobicity, and rigidity. Combinatorial techniques suitable for synthesizing small molecules are known in the art, e.g., as exemplified by Obrecht and Villalgordo, Solid-Supported Combinatorial and Parallel Synthesis of Small-Molecular-Weight Compound Libraries, Pergamon-Elsevier Science Limited (1998), and include those such as the "split and pool" or "parallel" synthesis techniques, solid-phase and solution-phase techniques, and encoding techniques (see, for example, Czarnik, Curr. Opin. Chem. Bio., 1:60 (1997). In addition, a number of small molecule libraries are commercially available.

Particular screening applications of this invention relate to the testing of pharmaceutical compounds in drug research. The reader is referred generally to the standard textbook "In vitro Methods in Pharmaceutical Research", Academic Press, 1997, and U.S. Pat. No. 5,030,015). Assessment of the activity of candidate pharmaceutical compounds generally involves administering a candidate compound, determining any change in the morphology, marker phenotype and expression, or metabolic activity of the cells and function of the cells that is attributable to the compound (compared with untreated cells or cells treated with an inert compound), and then correlating the effect of the compound with the observed change.

The screening may be done, for example, either because the compound is designed to have a pharmacological effect on certain cell types, or because a compound designed to have effects elsewhere may have unintended side effects. Two or more drugs can be tested in combination (by combining with the cells either simultaneously or sequentially), to detect possible drug-drug interaction effects. In some applications, compounds are screened initially for potential toxicity (Castell et al., pp. 375-410 in "In vitro Methods in Pharmaceutical Research," Academic Press, 1997). Cytotoxicity can be determined in the first instance by the effect on cell viability, survival, morphology, and expression or release of certain markers, receptors or enzymes. Effects of a drug on chromosomal DNA can be determined by measuring DNA synthesis or repair. [$^3$H] thymidine or BrdU incorporation, especially at unscheduled times in the cell cycle, or above the level required for cell replication, is consistent with a drug effect. Unwanted effects can also include unusual rates of sister chromatid exchange, determined by metaphase spread. The reader is referred to A. Vickers (PP 375-410 in "In vitro Methods in Pharmaceutical Research," Academic Press, 1997) for further elaboration.

In one embodiment of the invention, a method of identifying a candidate agent is provided said method comprising: (a) contacting a biological sample from a patient with the candidate agent and determining the level of expression of one or more biomarkers described herein; (b) determining the level of expression of a corresponding biomarker or biomarkers in an aliquot of the biological sample not contacted with the candidate agent; (c) observing the effect of the candidate agent by comparing the level of expression of the biomarker or biomarkers in the aliquot of the biological sample contacted with the candidate agent and the level of expression of the corresponding biomarker or biomarkers in the aliquot of the biological sample not contacted with the candidate agent; and (d) identifying said agent from said observed effect, wherein an at least 10% difference between the level of expression of the biomarker gene or combination of biomarker genes in the aliquot of the biological sample contacted with the candidate agent and the level of expression of the corresponding biomarker gene or combination of biomarker genes in the aliquot of the biological sample not contacted with the candidate agent is an indication of an effect of the candidate agent.

In preferred embodiments, the effects of the drug are correlated with the expression of the molecular signatures associated with a good prognosis as described in detail in the examples which follow.

In another embodiment of the invention, a candidate agent derived by the method according to the invention is provided.

In another embodiment of the invention, a pharmaceutical preparation comprising an agent according to the invention is provided.

In another preferred embodiment of the invention, a method of producing a drug comprising the steps of the method according to the invention (i) synthesizing the candidate agent identified in step (c) above or an analog or derivative thereof in an amount sufficient to provide said drug in a therapeutically effective amount to a subject; and/or (ii) combining the drug candidate the candidate agent identified in step (c) above or an analog or derivative thereof with a pharmaceutically acceptable carrier.

Vectors, Cells:

In some embodiments it is desirable to express the biomolecules that comprise a biomarker, in a vector and in cells. The applications of such combinations are unlimited. The vectors and cells expressing the one or more biomolecules can be used in assays, kits, drug discovery, diagnostics, prognostics and the like. The cells can be stem cells isolated from the bone marrow as a progenitor cell, or cells obtained from any other source, such as for example, ATCC.

"Bone marrow derived progenitor cell" (BMDC) or "bone marrow derived stem cell" refers to a primitive stem cell with the machinery for self-renewal constitutively active. Included in this definition are stem cells that are totipotent, pluripotent and precursors. A "precursor cell" can be any cell in a cell differentiation pathway that is capable of differentiating into a more mature cell. As such, the term "precursor cell population" refers to a group of cells capable of developing into a more mature cell. A precursor cell population can comprise cells that are totipotent, cells that are pluripotent and cells that are stem cell lineage restricted (i.e. cells capable of developing into less than all hematopoietic lineages, or into, for example, only cells of erythroid lineage). As used herein, the term "totipotent cell" refers to a cell capable of developing into all lineages of cells. Similarly, the term "totipotent population of cells" refers to a composition of cells capable of developing into all lineages of cells. Also as used herein, the term "pluripotent cell" refers to a cell capable of developing into a variety (albeit not all) lineages and are at least able to develop into all hematopoietic lineages (e.g., lymphoid, erythroid, and thrombocytic lineages). Bone marrow derived stem cells contain two well-characterized types of stem cells. Mesenchymal stem cells (MSC) normally form chondrocytes and osteoblasts. Hematopoietic stem cells (HSC) are of mesodermal origin that normally give rise to cells of the blood and immune system (e.g., erythroid, granulocyte/macrophage, magakaryocyte and lymphoid lineages). In addition, hematopoietic stem cells also have been shown to have the potential to differentiate into the cells of the liver (including hepatocytes, bile duct cells), lung, kidney (e.g., renal tubular epithelial cells and renal parenchyma), gastrointestinal tract, skeletal muscle fibers, astrocytes of the CNS, Purkinje neurons, cardiac muscle (e.g., cardiomyocytes), endothelium and skin.

In a preferred embodiment, a method of identifying candidate therapeutic compounds comprises culturing cells expressing at least one biomolecule selected from: 232669_at (Hypoxia inducible factor 3, alpha subunit), 214951_at (solute carrier family 26, member 10), 243482_at (Epidermal growth factor receptor pathway substrate 15-like 1), 226210_s_at (maternally expressed 3), 232159_at (Epidermal growth factor receptor pathway substrate 15-like 1), 233026_s_at (PDZ domain containing), 211996_s_at (KIAA0220-like protein hypothetical gene LOC 283846), 243774_at (mucin 20, cell surface associated), 242551_at (Chromosome 18 open reading frame), 244548_at (Rho GTPase activating protein 26), 244208_at (Checkpoint suppressor 1), 239984_at (Sodium channel, voltage-gated, type VII, alpha), 230683_at (CDNA:FLJ20892 fis, clone ADKA03430), 214869_at (apolipoprotein L, 6), 241597_at (Arginine-glutamic acid dipeptide (RE) repeats), 235887_at (Smg-6 homolog, nonsense mediated mRNA decay factor (C. elegans)), 229957_at (transmembrane protein 91), 223546_x_at (LUC7L-like (S. cerevisiae)), 239567_at (Rho GTPase activating protein 10), 242194_at (Cullin 4A), 1558525_at (hypothetical protein LOC283901), 227178_at (CUG triplet repeat, RNA binding protein 2), 228198_s_at (Mitochondrial ribosomal protein S9), 202379_s_at (natural killer-tumor recognition sequence), 224260_at (CDNA clone), 238643_at (Neuroblastoma, suppression of tumorigenicity 1), 232253_at (RAD50 homolog (S. cerevisiae)), 227968_at (Parkinson disease 7 domain containing 1), 233197_at (kelch-like 9 (Drosophila)), 244512_at (transcribed locus strongly similar to XP 0010813421), 233443_at (hypothetical protein LOC389362), 231275_at (FLJ42875 protein), 226419_s_at (hypothetical protein LOC64546), 201221_s_at small nuclear ribonucleoprotein 70 kDa polypeptide), 209354_at (tumor necrosis factor receptor family member 14), 226571_s_at (protein tyrosine phosphatase receptor type, S), 220728_at (EST), 203071_at (sema domain, immunoglobulin domain (Ig), short basic domain), 213946_s_at obscurin-like 1, similar to titin isoform N2-B), 201394_s_at (RNA binding motif protein 5), 203748_x_at (RNA binding motif, single stranded interacting protein 1), 223147_s_at (WD repeat domain 33), 213773_x_at (NOL/NOP2/Sun domain family, member 5), 1560049_at CUG triplet repeat, RNA binding protein 2), 243974_at (CDNA clone IMAGE:4821815), 201510_at E74-like factor 3 (ets domain transcription factor, epithelial specific) complementary sequences, fragments, alleles, variants, derivatives and/or gene products thereof, with a candidate therapeutic agent; identifying candidate therapeutic agents which modulate the expression of the biomolecules and identifying a candidate therapeutic agent. Preferably, a candidate therapeutic agent comprises organic molecules, inorganic molecules, vaccines, antibodies, nucleic acid molecules, proteins, peptides and vectors expressing nucleic acid molecules.

In a preferred embodiment, a method of identifying candidate therapeutic compounds comprises culturing cells expressing at least one biomolecule selected from: 1558458_at (Hypothetical LOC401320), 1560049_at (CUG triplet repeat, RNA binding protein 2, CUGBP2), 201394_s_at (RNA binding motif protein 5, RBM5), 201655_s_at (heparan sulfate proteoglycan 2 (perlecan), HSPG2), 202379_s_at (natural killer-tumor recognition sequence, NKTR), 202808_at, 203071_at (sema domain, immunoglobulin domain (Ig), short basic domain, secreted, (semaphorin) 3B, SEMA3B), 203748_x_at (RNA binding motif, single stranded interacting protein 1, RBMS1), 203981_s_at (ATP-binding cassette, sub-family D (ALD), member 4, ABCD4), 204737_s_at (myosin, heavy chain 6, myosin, heavy chain 7, MYH6///MYH7), 204978_at (splicing factor, arginine/serine-rich 16, SFRS16), 206209_s_at (carbonic anhydrase IV, CA4), 207541_s_at (exosome component 10, EXOSC10), 207798_s_at (ataxin 2-like, ATXN2L), 208978_at (cysteine-rich protein 2, CRIP2), 209354_at (tumor necrosis factor receptor superfamily, member 14 TNFRSF14), 210628_x_at (latent transforming growth factor beta binding protein 4, LTBP4), 211909_x_at (prostaglandin E receptor 3 (subtype EP3), PTGER3), 211996_at (KIAA0220-like protein, nuclear pore complex (LOC23117), 212487_at (G patch domain containing 8, GPATCH8), 213946_s_at (obscurin-like 1, OBSL1), 214951_at (solute carrier family 26, member 10, SLC26A10), 220219_s_at (leucine rich repeat containing 37A, LRRC37A), 221071_at, 221780_s_at (DEAD (Asp-Glu-Ala-Asp) box polypeptide 27DDX27), 221806_s_at (SET domain containing 5, SETD5), 221833_at (Lon peptidase 2, peroxisomal, LONP2), 223546_x_at (LUC7-like (S. cerevisiae), LUC7L), 224260_at (CDNA clone IMAGE: 4478733), 225562_at (AS p21 protein activator 3, RASA3), 226040_at (MRNA; cDNA DKFZp762N156 (from clone DKFZp762N156), 227968_at (Parkinson disease 7 domain containing 1, PDDC1), 228198_s_at (Mitochondrial ribosomal protein S9, MRPS9), 229830_at (Transcribed locus), 230683_at (CDNA: FLJ20892 fis, clone ADKA03430), 238185_at (RNA binding motif, single stranded interacting protein 1, RBMS1), 241597_at (Arginine-glutamic acid dipeptide (RE) repeats, RERE), 242551_at (Chromosome 18 open reading frame 1, C18orf1), 244208_at (Checkpoint suppressor 1, CHES1), 244494_at (Zinc finger, DHHC-type containing 1, ZDHHC1), and 244548_at (Rho GTPase activating protein 26, ARHGAP26) complementary sequences, fragments, alleles, variants, derivatives and/or gene products thereof, with a candidate therapeutic agent; identifying candidate therapeutic agents which modulate the expression of the biomolecules and identifying a candidate therapeutic agent. Preferably, a candidate therapeutic agent comprises organic molecules, inorganic molecules, vaccines, antibodies, nucleic acid molecules, proteins, peptides and vectors expressing nucleic acid-molecules.

Such compounds are useful, e.g., as candidate therapeutic compounds for the treatment of heart disease, heart disorders and conditions thereof. Thus, included herein are methods for screening for candidate therapeutic compounds for the treatment of, for example, myocarditis, Coronary Heart Disease, angina, Acute Coronary Syndrome, Aortic Aneurysm and Dissection, arrhythmias, Cardiomyopathy, Congenital Heart Disease, congestive heart failure or chronic heart failure, pericarditis, and the like. The methods include administering the compound to a model of the condition, e.g., contacting a cell (in vitro) model with the compound, or administering the compound to an animal model of the condition, e.g., an animal model of a condition associated with heart disease. The model is then evaluated for an effect of the candidate compound on the clinical outcome in the model and can be considered a candidate therapeutic compound for the treatment of the condition. Such effects can include clinically relevant effects, decreased pain; increased life span; and so on. Such effects can be determined on a macroscopic or microscopic scale. Candidate therapeutic compounds identified by these methods can be further verified, e.g., by administration to human subjects in a clinical trial.

The biomolecules can be expressed from one or more vectors. A "vector" (sometimes referred to as gene delivery or gene transfer "vehicle") refers to a macromolecule or complex of molecules comprising a polynucleotide to be delivered to a host cell, either in vitro or in vivo. The polynucleotide to be delivered may comprise a coding sequence of interest in gene therapy. Vectors include, for example, viral vectors (such as adenoviruses ("Ad"), adeno-associated viruses (AAV), and retroviruses), liposomes and other lipid-containing complexes, and other macromolecular complexes capable of mediating delivery of a polynucleotide to a host cell. Vectors_ can also comprise other components or functionalities that further modulate gene delivery and/or gene expression, or that otherwise provide beneficial properties to the targeted cells. As described and illustrated in more detail below, such other components include, for example, components that influence binding or targeting to cells (including components that mediate cell-type or tissue-specific binding); components that influence uptake of the vector nucleic acid by the cell; components that influence localization of the polynucleotide within the cell after uptake (such as agents mediating nuclear localization); and components that influence expression of the polynucleotide. Such components also might include markers, such as detectable and/or selectable markers that can be used to detect or select for cells that have taken up and are expressing the nucleic acid delivered by the vector. Such components can be provided as a natural feature of the vector (such as the use of certain viral vectors which have components or functionalities mediating binding and uptake), or vectors can be modified to provide such functionalities. Other vectors include those described by Chen et al; BioTechniques, 34: 167-171 (2003). A large variety of such vectors are known in the art and are generally available.

Kits

In another preferred embodiment, a kit is provided comprising any one or more of the biomolecules comprising: 232669_at (Hypoxia inducible factor 3, alpha subunit), 214951_at (solute carrier family 26, member 10), 243482_at (Epidermal growth factor receptor pathway substrate 15-like 1), 226210_s_at (maternally expressed 3), 232159_at (Epidermal growth factor receptor pathway substrate 15-like 1), 233026_s_at (PDZ domain containing), 211996_s_at (KIAA0220-like protein hypothetical gene LOC 283846), 243774_at (mucin 20, cell surface associated), 242551_at (Chromosome 18 open reading frame), 244548_at (Rho GTPase activating protein 26), 244208_at (Checkpoint suppressor 1), 239984_at (Sodium channel, voltage-gated, type VII, alpha), 230683_at (CDNA:FLJ20892 fis, clone ADKA03430), 214869_at (apolipoprotein L, 6), 241597_at (Arginine-glutamic acid dipeptide (RE) repeats), 235887_at (Smg-6 homolog, nonsense mediated mRNA decay factor (C. elegans)), 229957_at (transmembrane protein 91), 223546_x_at (LUC7L-like (S. cerevisiae)), 239567_at (Rho GTPase activating protein 10), 242194_at (Cullin 4A), 1558525_at (hypothetical protein LOC283901), 227178_at (CUG triplet repeat, RNA binding protein 2), 228198_s_at (Mitochondrial ribosomal protein S9), 202379_s_at (natural killer-tumor recognition sequence), 224260_at (CDNA clone), 238643_at (Neuroblastoma, suppression of tumorigenicity 1), 232253_at (RAD50 homolog (S. cerevisiae)), 227968_at (Parkinson disease 7 domain containing 1), 233197_at (kelch-like 9 (Drosophila)), 244512_at (transcribed locus strongly similar to XP 0010813421), 233443_at (hypothetical protein LOC389362), 231275_at (FLJ42875 protein), 226419_s_at (hypothetical protein LOC64546), 201221_s_at small nuclear ribonucleoprotein 70 kDa polypeptide), 209354_at (tumor necrosis factor receptor family member 14), 226571_s_at (protein tyrosine phosphatase receptor type, S), 220728_at (EST), 203071_at (sema domain, immunoglobulin domain (Ig), short basic domain), 213946_s_at obscurin-like 1, similar to titin isoform N2-B), 201394_s_at (RNA binding motif protein 5), 203748_x_at (RNA binding motif, single stranded interacting protein 1), 223147_s_at (WD repeat domain 33), 213773_x_at (NOL/NOP2/Sun domain family, member 5), 1560049_at CUG triplet repeat, RNA binding protein 2), 243974_at (CDNA clone IMAGE:4821815), 201510_at E74-like factor 3 (ets domain transcription factor, epithelial specific), complementary sequences, fragments, alleles, variants, derivatives and/or gene products thereof.

In another preferred embodiment, a kit is provided comprising any one or more of the biomolecules comprising: 1558458_at (Hypothetical LOC401320), 1560049_at (CUG triplet repeat, RNA binding protein 2, CUGBP2), 201394_s_at (RNA binding motif protein 5, RBM5), 201655_s_at (heparan sulfate proteoglycan 2 (perlecan), HSPG2), 202379_s_at (natural killer-tumor recognition sequence, NKTR), 202808_at, 203071_at (sema domain, immunoglobulin domain (Ig), short basic domain, secreted, (semaphorin) 3B, SEMA3B), 203748_x_at (RNA binding motif, single stranded interacting protein 1, RBMS1), 203981_s_at (ATP-binding cassette, sub-family D (ALD), member 4, ABCD4), 204737_s_at (myosin, heavy chain 6, myosin, heavy chain 7, MYH6///MYH7), 204978_at (splicing factor, arginine/serine-rich 16, SFRS16), 206209_s_at (carbonic anhydrase IV, CA4), 207541_s_at (exosome component 10, EXOSC10), 207798_s_at (ataxin 2-like, ATXN2L), 208978_at (cysteine-rich protein 2, CRIP2), 209354_at (tumor necrosis factor receptor superfamily, member 14 TNFRSF14), 210628_x_at (latent transforming growth factor beta binding protein 4, LTBP4), 211909_x_at (prostaglandin E receptor 3 (subtype EP3), PTGER3), 211996_at (KIAA0220-like protein, nuclear pore complex (LOC23117), 212487_at (G patch domain containing 8, GPATCH8), 213946_s_at (obscurin-like 1, OBSL1), 214951_at (solute carrier family 26, member 10, SLC26A10), 220219_s_at (leucine rich repeat containing 37A, LRRC37A), 221071_at, 221780_s_at (DEAD (Asp-Glu-Ala-Asp) box polypeptide 27DDX27), 221806_s_at (SET domain containing 5, SETD5), 221833_at (Lon peptidase 2, peroxisomal, LONP2), 223546_x_at (LUC7-like (S. cerevisiae), LUC7L), 224260_at (CDNA clone IMAGE: 4478733), 225562_at (AS p21 protein activator 3, RASA3), 226040_at (MRNA; cDNA DKFZp762N156 (from clone DKFZp762N156), 227968_at (Parkinson disease 7 domain containing 1, PDDC1), 228198_s_at (Mitochondrial ribosomal protein S9, MRPS9), 229830_at (Transcribed locus), 230683_at (CDNA: FLJ20892 fis, clone ADKA03430), 238185_at (RNA binding motif, single stranded interacting protein 1, RBMS1), 241597_at (Arginine-glutamic acid dipeptide (RE) repeats, RERE), 242551_at (Chromosome 18 open reading frame 1, C18orf1), 244208_at (Checkpoint suppressor 1, CHES1), 244494_at (Zinc finger, DHHC-type containing 1, ZDHHC1), and 244548_at (Rho GTPase activating protein 26, ARHGAP26), complementary sequences, fragments, alleles, variants, derivatives and/or gene products thereof.

For use in the applications described or suggested above, kits or articles of manufacture are also provided by the invention. Such kits may comprise a carrier means being compartmentalized to receive in close confinement one or more container means such as vials, tubes, and the like, each of the container means comprising one of the separate elements to be used in the method. For example, one of the container means may comprise a probe that is or can be detectably labeled. Where the kit utilizes nucleic acid hybridization to detect the target nucleic acid, the kit may also have containers containing nucleotide(s) for amplification of the target nucleic acid sequence and/or a container comprising a reporter-means, such as a biotin-binding protein, such as avidin or streptavidin, bound to a reporter molecule, such as an enzymatic, florescent, or radioisotope label.

The kit of the invention will typically comprise the container described above and one or more other containers comprising materials desirable from a commercial and user standpoint, including buffers, diluents, filters, needles, syringes, and package inserts with instructions for use. A label may be present on the container to indicate that the composition is used for a specific therapy or non-therapeutic application, and may also indicate directions for either in vivo or in vitro use, such as those described above.

The kits of the invention have a number of embodiments. A typical embodiment is a kit comprising a container, a label on said container, and a composition contained within said container; wherein the composition includes a primary antibody that binds to the biomolecules of each molecular signature and instructions for using the antibody for evaluating the presence of biomolecules in at least one type of mammalian cell. The kit can further comprise a set of instructions and materials for preparing a tissue sample and applying antibody and probe to the same section of a tissue sample. The kit may include both a primary and secondary antibody, wherein the secondary antibody is conjugated to a label, e.g., an enzymatic label.

Another embodiment is a kit comprising a container, a label on said container, and a composition contained within said container; wherein the composition includes a polynucleotide that hybridizes to a complement of the polynucleotides under stringent conditions, the label on said container indicates that the composition can be used to evaluate the presence of a molecular signature in at least one type of mammalian cell, and instructions for using the polynucleotide for evaluating the presence of biomolecule RNA or DNA in at least one type of mammalian cell.

Other optional components in the kit include, microarrays, one or more buffers (e.g., block buffer, wash buffer, substrate buffer, etc), other reagents such as substrate (e.g., chromogen) which is chemically altered by an enzymatic label, epitope retrieval solution, control samples (positive and/or negative controls), control slide(s) etc.

All documents mentioned herein are incorporated herein by reference. All publications and patent documents cited in this application are incorporated by reference for all purposes to the same extent as if each individual publication or patent document were so individually denoted. By their citation of various references in this document, Applicants do not admit any particular reference is "prior art" to their invention. Embodiments of inventive compositions and methods are illustrated in the following examples.

EXAMPLES

The following non-limiting Examples serve to illustrate selected embodiments of the invention. It will be appreciated that variations in proportions and alternatives in elements of the components shown will be apparent to those skilled in the art and are within the scope of embodiments of the present invention.

Example 1: Transcriptomic Biomarkers for Individual Risk Assessment in New Onset Heart Failure Accurate risk assessment and prediction of prognosis at first presentation are crucial for appropriate allocation of therapy, monitoring and patient management. In this study, a transcriptomic based biomarker (TBB) is presented which has been derived from a single endomyocardial biopsy (EMB) and which predicts the long term clinical outcome of patients with idiopathic dilated cardiomyopathy (IDCM) with very high accuracy.

Materials and Methods

Abbreviations:

NYHA, New York Heart Association classification; LV EF, left ventricular ejection fraction, LVIDD, left ventricular internal diastolic dimension; PAP, pulmonary artery pressure; PCWP, pulmonary capillary wedge pressure.

Patients:

EMBs were collected from patients that were referred to Johns Hopkins Hospital between 1997 and 2006 for evaluation of cardiomyopathy (n=35012). A clinical data base of patient outcome was maintained concurrently for a 10 year period beginning in 1997. All patients gave written informed consent for sample collection and medical chart abstraction. Transvenous EMBs from the right ventricular septum were obtained for microarray analysis as previously described (Felker G M, Thompson R E, Hare J M et al. *N Engl J Med* 2000; 342: 1077-8). In order to avoid possible disease specific confounding factors, samples from one single frequent type of cardiomyopathy (IDCM), were selected. IDCM was a diagnosis of exclusion after extensive histological work-up without any detectable pathological signs. Within a repository of 180 IDCM samples, biopsies were selected in a case-control fashion based on the phenotypic extremes in survival of the cohort. A group with good prognosis (GP, n=25), was defined as having event free survival for at least 5 years after initial presentation with heart failure symptoms; a group with bad prognosis (BP, n=18), experienced an event within the first 2 years. Events included death (n=14), requirement for left ventricular assist device (n=2) or cardiac transplantation (n=2).

Processing of Biopsies:

EMBs were immediately flash frozen in liquid nitrogen for storage in a biorepository. All steps of RNA isolation and processing were performed according to MIAME guidelines (Minimum Information about a Microarray Experiment). Tissue samples (average diameter ~2 mm) were homogenized with the MM 301 Mixer Mill (Retsch, Cat. No. 85120). Trizol reagent together with the Micro-to-Midi Total RNA Purification System (Invitrogen, Cat. No. 12183-018) was used for extraction of total RNA (success rate: 97% of samples). Concentration and integrity of total RNA was measured with the Agilent 2100 Bioanalyzer. All RNA samples exhibited intact 28S and 18S ribosomal RNA on denaturing agarose gel electrophoresis and the 260/280 nm absorbance readings fell in the acceptable range of 1.8-2.1. An average amount of 586 ng total RNA was isolated and preprocessed with the Ovation Biotin RNA Amplification and Labeling System (NuGen, Cat. No. 2300-12).

Microarray Hybridization:

Samples were hybridized to the Human Genome U133 Plus 2.0 Array from Affymetrix without additional amplification step. The microarray experiments were judged successful when RNA isolation and microarray hybridization met all the indices of quality control as specified in the Affymetrix Guideline for Assessing Sample and Array Quality. Average background and noise of all chips registered within acceptable ranges and hybridization efficiencies were similar for all samples.

Statistical Analysis:

Raw intensity values from microarray hybridization were normalized with Robust Multiarray Average (RMA) implemented in the R package for statistical computing (available at www.R-project.com) In the next step, Significance Analysis of Microarrays (SAM) was used to identify phenotype specific differences in gene expression. SAM defines significance with the q-value, an adjusted p-value for multiple comparisons (Storey J. *Journal of the Royal Statistical Society* 2007:64:479-498). For the development of a TBB, Prediction Analysis of Microarrays (PAM) was used to create a classifier in a training set (containing ⅔ of the data, n=29), with subsequent validation in a test set (containing ⅓ of the data, n=14). Overall accuracy was assessed after 50 random partitions. To test for balanced baseline conditions of subgroups in the cohort (train and test set), a t-test and One Way ANOVA was used, or Mann-Whitney Rank Sum Test and Kruskal-Wallis One Way ANOVA on Ranks if required.

Results

The ability to distinguish patients who will improve their functional status from those who will go on to circulatory collapse and require cardiac transplant or LVAD placement, remains an important clinical challenge.

Patient Characteristics:

A total of 43 EMBs were analyzed with microarray technology to identify phenotype specific differences in gene expression and to develop a prognostic TBB. Table 1 contains the baseline conditions of all patients. The table was divided into 4 subgroups according to clinical outcome and subdivisions used for PAM analysis, in order to exclude possible bias that may be caused by unbalanced risk parameters in the train and test cohorts. There were no significant differences in age, gender, ventricular function, hemodynamics or drug therapy between the subgroups. The overall population with IDCM presented at an average age of 46±15 years, with slight overrepresentation of the male gender (67%). All subgroups were at an advanced NYHA stage of 2.6±0.7 with severely compromised ejection fraction (EF) of 23±13%, average LVIDD of 6.1±1.5 cm and pulmonary capillary wedge pressure (PCWP) of 15±9 mmHg.

TABLE 1

|  | Good prognosis (n = 25) | Poor prognosis (n = 18) |
| --- | --- | --- |
| Age | 46 ± 15 | 48 ± 17 |
| Male, n (%) | 17 (68%) | 12 (67%) |
| NYHA, n (%) | | |
| I | 1 (4%) | 1 (5%) |
| II | 13 (52%) | 6 (33%) |
| III | 10 (40%) | 8 (44%) |
| IV | 1 (4%) | 4 (22%) |
| LV EF, % | 24 ± 13 | 23 ± 13 |
| LVIDD, cm | 6.4 ± 1 | 6.3 ± 2 |
| PAP, mmHg | | |
| Systolic | 36 ± 13 | 41 ± 13 |
| Diastolic | 16 ± 6 | 20 ± 11 |
| Pulmonary capillary wedge Pressure, mmHg | 13 ± 7 | 18 ± 10 |
| Medications, n (%) | | |
| 6-Antogonist | 17 (68%) | 13 (72%) |
| ACE inhibitor | 17 (68%) | 12 (67%) |
| Aldosterone antagonist | 4 (16%) | 4 (22%) |
| Diuretic | 17 (68%) | 15 (83%) |
| Intravenous inotropic therapy | 0 | 0 |

Figure 2:
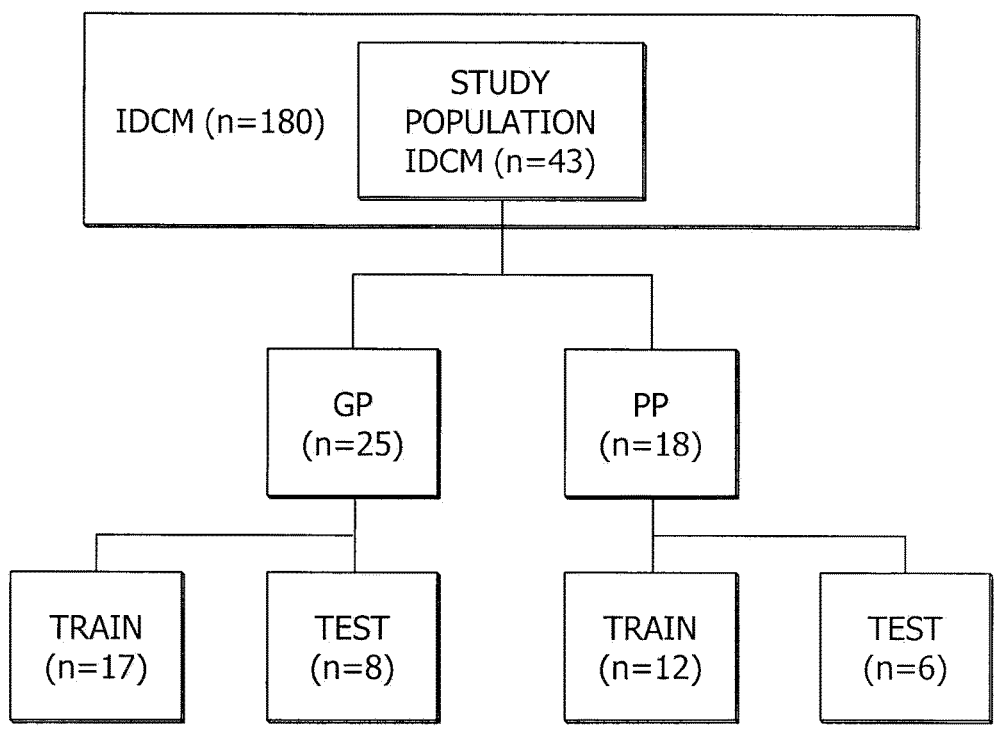
FIG. 2 is a schematic representation of train and test sets as used for the development of a classifier with Prediction Analysis of Microarrays (PAM). All samples obtained from patients with poor prognosis (PP, n=18) were selected from a biorepository (n=180) and those with good prognosis (GP, n=25) were chosen in a case-control fashion (see text for definitions of PP and GP). The classifier, a nearest shrunken centroid, was developed in ⅔ of the data (17 samples with GP; 12 samples with PP) with subsequent validation in the remaining ⅓ of data (8 samples with GP; 6 samples with PP). The overall test accuracy of the TBB was calculated from 50 random partitions into train and test sets.

Microarray Analysis:

An average of 568±92 ng of total RNA was isolated from all EMBs and tested with the Agilent 2100 Bioanalyzer, revealing high integrity and purity of RNA of all samples with consistent bands of 18S and 28S RNA (FIG. 1). There were 46 significantly overexpressed genes in patients who recovered from heart failure (q<5%, FC>1.2, Table 1) as determined with SAM. PAM was used to evaluate the predictive value of this set of genes. To achieve this and test for validity, patients were allocated into training sets consisting of ⅔ of samples (n=29), and test sets containing ⅓ of samples (n=14; FIG. 2). This approach resulted in a 'nearest shrunken centroid' of 45 genes, which distinguished with high accuracy between high risk patients and those with an excellent prognosis.

TABLE 2

46 significantly overexpressed genes in heart failure patients with good prognostic outcome (q < 5%, FC > 1.2).

| affy ID | Gene title | Fold Change |
| --- | --- | --- |
| 232669_at | Hypoxia inducible factor 3, alpha subunit | 1.8 |
| 214951_at | solute carrier family 26, member 10 | 1.8 |
| 243482_at | Epidermal growth factor receptor pathway substrate 15-like 1 | 1.8 |
| 226210_s_at | maternally expressed 3 | 1.7 |
| 232159_at | Epidermal growth factor receptor pathway substrate 15-like 1 | 1.7 |
| 233026_s_at | PDZ domain containing 2 | 1.6 |
| 211996_s_at | KIAA0220-like protein hypothetical gene LOC 283846 | 1.6 |
| 243774_at | mucin 20, cell surface associated | 1.6 |
| 242551_at | Chromosome 18 open reading frame 1 | 1.6 |
| 244548_at | Rho GTPase activating protein 26 | 1.6 |
| 244208_at | Checkpoint suppressor 1 | 1.6 |
| 239984_at | Sodium channel, voltage-gated, type VII, alpha | 1.6 |
| 230683_at | CDNA:FLJ20892 fis, clone ADKA03430 | 1.5 |
| 241869_at | apolipoprotein L, 6 | 1.5 |
| 241597_at | Arginine-glutamic acid dipeptide (RE) repeats | 1.5 |
| 235887_at | Smg-6 homolog, nonsense mediated mRNA decay factor (C. elegans) | 1.5 |
| 229957_at | transmembrane protein 91 | 1.5 |
| 223546_x_at | LUC7L-like (S. cerevisiae) | 1.5 |
| 239567_at | Rho GTPase activating protein 10 | 1.5 |
| 242194_at | Cullin 4A | 1.5 |
| 1558525_at | hypothetical protein LOC283901 | 1.4 |
| 227178_at | CUG triplet repeat, RNA binding protein 2 | 1.4 |
| 228198_s_at | Mitochondrial ribosomal protein S9 | 1.4 |
| 202379_s_at | natural killer-tumor recognition sequence | 1.4 |
| 224260_at | CDNA clone | 1.4 |
| 238643_at | Neuroblastoma, suppression of tumorigenicity 1 | 1.4 |
| 232253_at | RAD50 homolog (S. cerevisiae) | 1.4 |
| 227968_at | Parkinson diseaese 7 domain containing 1 | 1.4 |
| 233197_at | kelch-like 9 (Drosophila) | 1.4 |
| 244512_at | Transcribed locus, strongly similar to XP_001081342.1 | 1.4 |
| 233443_at | hypothetical protein LOC389362 | 1.4 |
| 231275_at | FLJ42875 protein | 1.4 |
| 226419_s_at | hypothetical protein LOC645460 | 1.4 |
| 201221_s_at | small nuclear ribonuleoprotein 70 kDa polypeptide | 1.4 |
| 209354_at | tumor necrosis factor receptor family member 14 | 1.4 |
| 226571_s_at | protein tyrosine phosphatase receptor type, S | 1.4 |
| 220728_at | EST | 1.3 |
| 203071_at | sema domain, immunoglobulin domain (Ig), short basic domain | 1.3 |
| 213946_s_at | obscurin-like 1, similar to titin isoform N2-B | 1.3 |
| 201394_s_at | RNA binding motif protein 5 | 1.3 |
| 203748_x_at | RNA binding motif, single stranded interacting protein 1 | 1.3 |
| 223147_s_at | WD repeat domain 33 | 1.3 |
| 213773_x_at | NOL1/NOP2/Sun domain family, member 5 | 1.3 |
| 1560049_at | CUG triplet repeat, RNA binding protein 2 | 1.3 |
| 243974_at | CDNA clone IMAGE: 4821815 | 1.2 |
| 201510_at | E74-like factor 3(ets domain transcription factor, epithelial specific) | 1.2 |

Validation:

To obtain the overall performance of our biomarker, 50 random partitions were performed into train and test sets, revealing an overall sensitivity of 74% (95% CI: 69%-79%) and an overall specificity of 90% (95% CI: 87%-93%). The positive predictive value was 85% (95% CI: 80%-89%), while the negative predictive value was 82% (95% CI: 78%-86%). The log odds ratio was 3.3. To assess the impact of various host factors, the 43 IDCM subjects were divided into multiple two-way strata based on age (≥ or <50 years), ejection fraction (≥ or <15%), and use of intravenous inotropes to test if the accuracy of the prognostic marker was affected by baseline parameters. The sensitivity and specificity of the TBB was then assessed, by determining the proportion of correctly classified subjects within each stratum. Notably, the predictive accuracy was perfect (sensitivity and specificity: 100%) both in patients over 50 years and patients with ejection fraction over 15%. None of our patients received inotropic medication.

Figure 3:
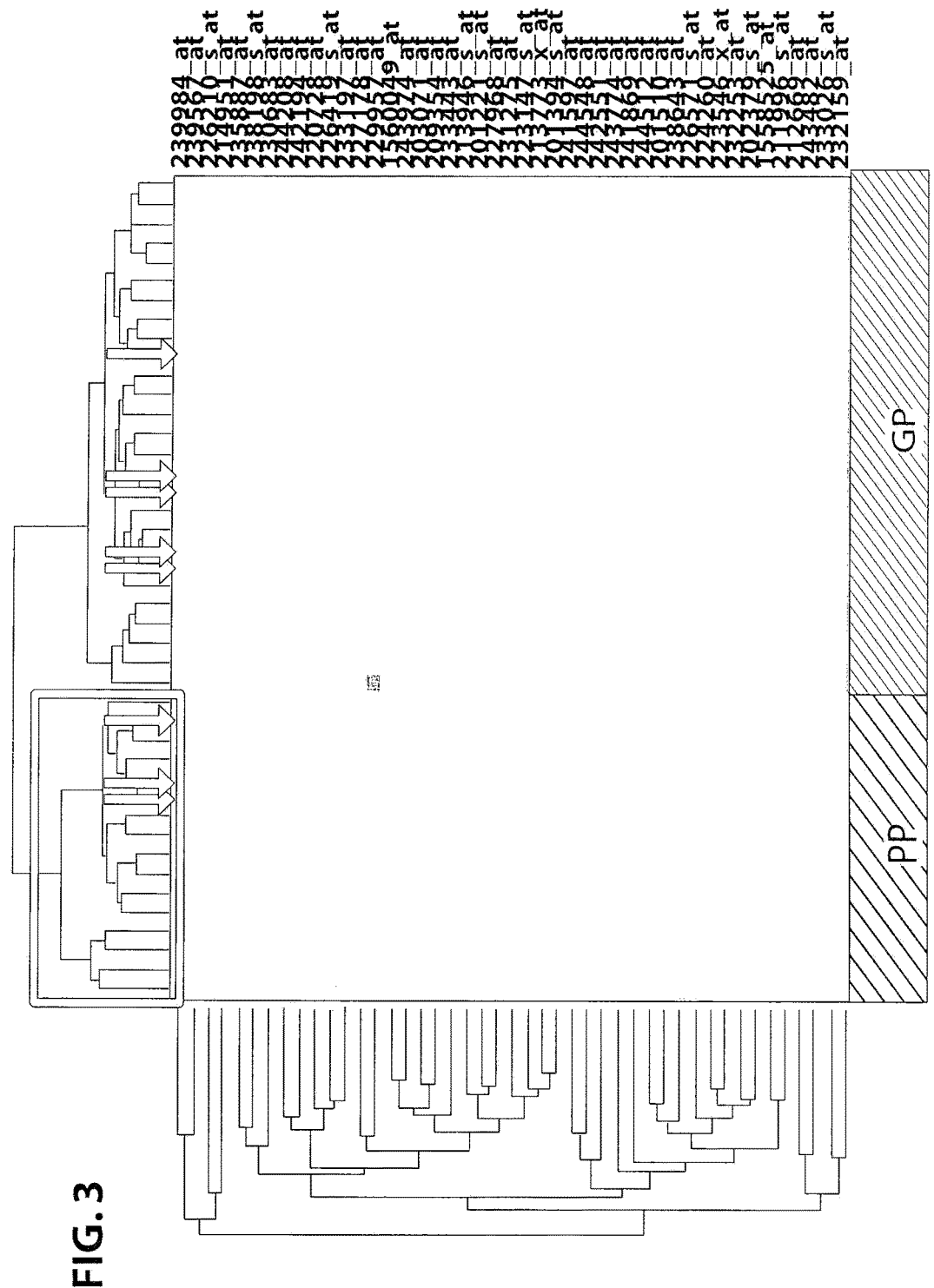
FIG. 3 is a heatmap of samples from all patients with idiopathic dilated cardiomyopathy (n=43). Each column corresponds to a patient sample and each row represents a gene. Samples classified as having PP form a distinct cluster and are highlighted in a red square. Downregulated genes are depicted with red, whereas upregulated genes are labeled blue. Yellow arrows denote misclassified samples.
Figure 4:
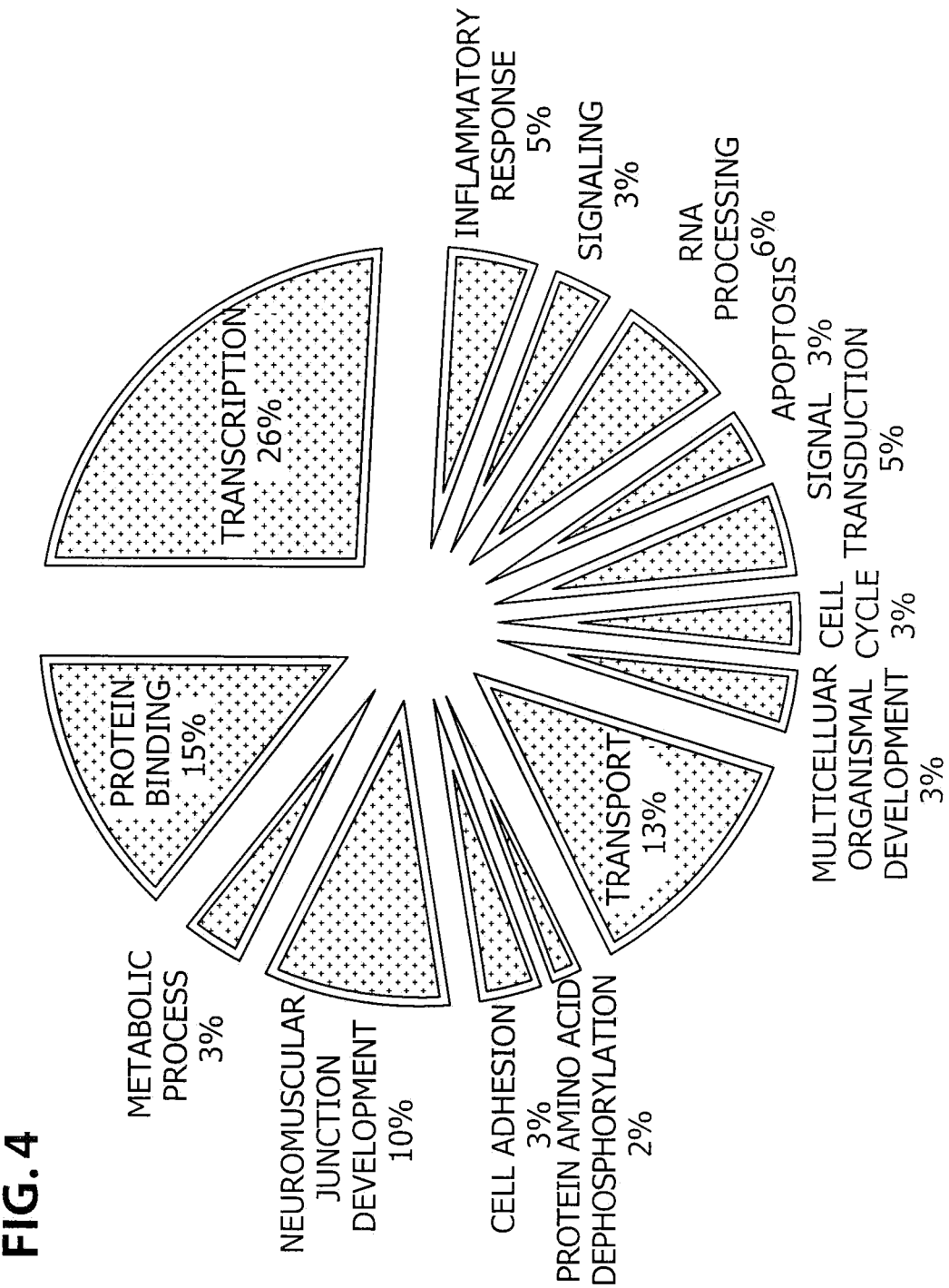
FIG. 4 is a pie chart illustrating involved pathways within the prognostic biomarker. Major pathways overexpressed in GP patients included transcription (26%), protein binding (15%), ion transport (13%) and neuromuscular development (10%).

The molecular signature is illustrated in a heatmap, which was created by Euclidean distance (FIG. 3). This independent approach of unsupervised clustering additionally confirmed the robustness of the discovered set of genes with very clear distinction of samples with BP from samples with GP. Pathways with major involvement were ion transport mechanisms (13%), neuromuscular development (10%), protein binding (15%) and transcription (26%) (www.geneontology.org, FIG. 4).

Figure 5:
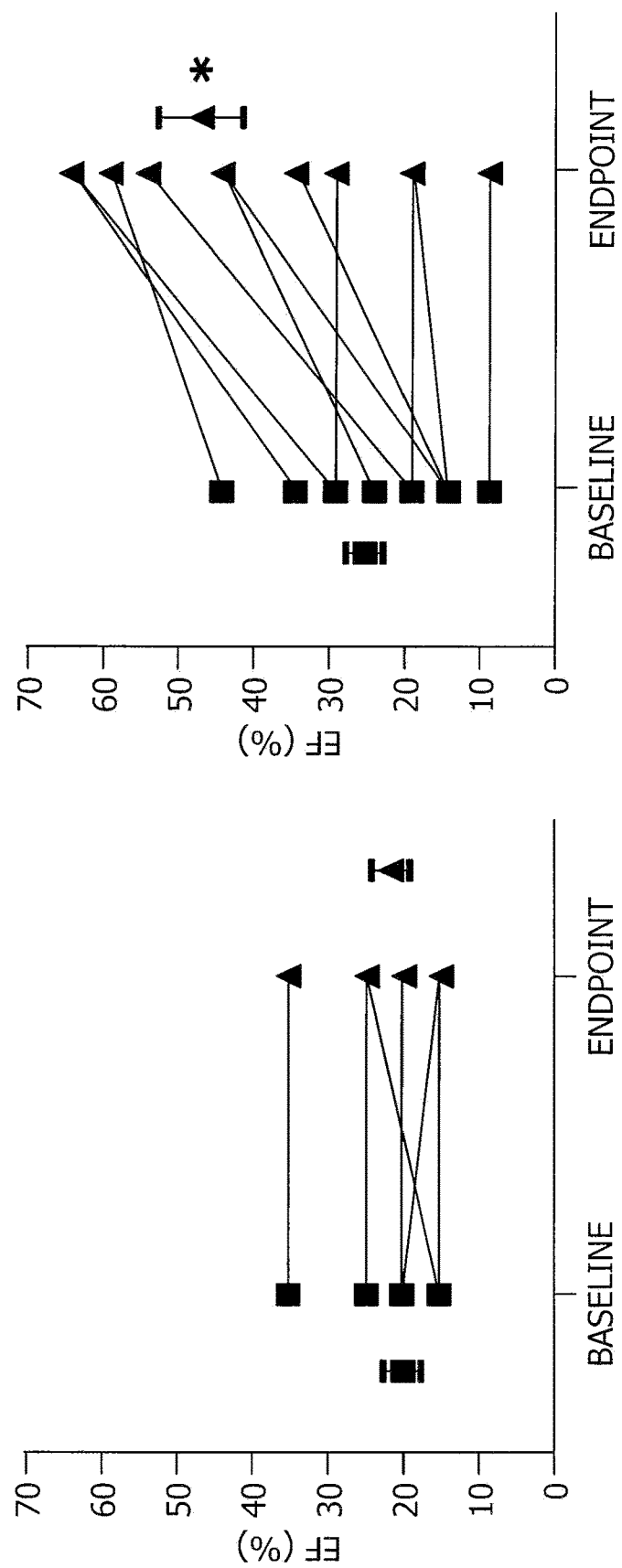
FIG. 5 shows two graphs illustrating the Functional improvement of Ejection fraction (EF) from baseline to endpoint: Within all enrolled cases of idiopathic cardiomyopathy (n=43), we further analyzed those of whom echocardiographic measurements at baseline and endpoint were available (n=17). Samples are classified into GP or PP based upon TBB prediction. Patients classified as GP (n=11, average follow-up: 49.9±21 mo) experienced improvement of EF (*P=0.0009), while PP (n=6, average follow-up: 6.2±2.9 mo) did not. Red line depicts one misclassified sample. Error bars represent SEM.

Prediction of Recovery in Left-Ventricular Function:

Improved clinical outcome is often associated with recovery in LV function. Accordingly, the hypothesis that the GP signature would be associated with improved ejection fraction was tested. Among the study sample (n=43), all subjects in whom paired echocardiography data from baseline and follow-up was available (n=17) were selected and characterized as GP or PP according to their TBB (FIG. 5). Patients classified as having GP experienced a substantial improvement in EF from 23±3% to 42±5% (P=0.0009), while patients with a PP molecular signature continued to have a depressed EF at 20±3% and 21±3% at baseline and follow-up, respectively.

Discussion:

One of the most valuable applications of genomic information has proven to be clinical prediction. Whereas the pattern of differentially expressed genes provides insight into disease etiology, it has also been used for the development of biomarkers. This approach has been highly successful in neoplastic disease and is emerging in a variety of other disease processes. Here, we sought to identify a TBB that predicted the clinical outcome of patients with new onset heart failure. We have developed a highly accurate prognostic biomarker, which is able to distinguish patients with very poor trajectory from those with excellent long-term prognosis. Importantly this study used biopsies from patients presenting at an early disease stage, without additional amplification of RNA. For two main reasons, this approach provides better accuracy and more representative results compared to previous studies: First, we are reporting initial transcriptomic differences without "noise" of unspecific compensatory changes that may be activated during the disease progress. Second, we avoided amplification bias which can occur due to different binding preferences of primers.

In addition to providing a novel and useful clinical biomarker, this study has offered insight into individual differences in gene expression that may be mechanistically involved in a poor outcome from heart failure. Most notably, we addressed a major unmet need in the management of heart failure, the ability to accurately assess patient prognosis. While there are emerging biomarkers of prognostic value, these markers do not dichotomize substantially between patients with very variable outcomes. Patients with near identical features at presentation, receiving identical therapy, can have dramatically differing prognoses. While some patients undergo complete recovery of their heart function within an average of 5 years, others progress into circulatory collapse within the first 2 years of presentation and require aggressive therapeutic interventions, such as mechanical circulatory assistance or cardiac transplantation.

The developed TBB, containing a nearest shrunken centroid of 45 genes, predicted the phenotype of samples with very high specificity (90%) suggesting its utility in particular as a rule out test and can be used in addition to current standard risk assessment. Furthermore, results of our TBB may be included in the assessment of a priority score in transplant lists. In combination with clinical data and laboratory values, our TBB is promising to provide better guidance in patient management.

It is of notice that our prognostic TBB performed perfectly in patients who were over 50 years old or who had an EF higher than 15%. In this regard, markers specific for age and function might be considered in the future. Future studies will be required to validate the precise clinical value of the TBB approach for new onset HF. Furthermore, our data strongly indicate a molecular component that impacts the recovery of patients with heart failure. Of the 46 differentially expresses genes (Table 2), all were overexpressed in patients who recovered from heart failure. Many overexpressed genes in these patients have RNA or DNA binding functions, e.g. RBMS1 and WDR33, playing a crucial role in DNA replication, gene transcription, cell cycle progression and apoptosis Various genes with critical regulatory functions were identified, i.e.: SNRP70; the nuclear transcription factors ELF3, CHES1, and RERE; NSUN4, a gene with methyltransferase activity, and the transcription factor HIF3A. HIF3A has been discussed as an inductor of glucose transporters, vascular endothelial growth factor and erythropoietin similar to HIF1A and HIF2A, while others postulated its counteraction with the other two subunits.

The genes CUGBP2, LUC7-like and SEMA3B are involved in neuromuscular development, axon guidance and regulation of heart contractility (www.geneontology.org/). Closely related in its function is also the overexpressed obscurin-like 1 gene, a linker that stabilizes cell contacts and organelles within the cytoskeleton and which is located at the intercalated discs in the adult cardiomyocyte. Obscurin-like 1 gene is supposed to have similar functions to obscurin, a multifunctional protein responsible for assembly of myofibrils and myocyte cellular organization. By its interaction with titin and ankyrin, as well as linking sarcomere and sarcoplasmic reticulum, it provides the required alignments for contraction.

Further we discovered two regenerative genes, Rad50 and SMG6, important key regulators in telomerase activity and DNA repair. Rad50 is part of the Mre1 1/Rad50/Nbs1 (MRN) complex, a functional unit that generates t-loops by inserting 3' G-overhangs at human telomere ends. These t-loops prevent chromosome ends from being recognized as damaged DNA and provide a template for telomerase and preservation of genome stability. The increase in telomerase activity might explain a protective effect against degenerative processes and aging in the heart of patients with good prognosis. It is attractive to speculate that the reason for better recovery may be due to increased cellular regenerative capacity since Rad50 may be important for viability of stem cells. Several genes within our prognostic TBB (SNRP 70 kDa, Obscurin like 1 and RNA binding motif) were consistent with findings of a study of 199 human LVAD samples that indicated that these genes are involved in recovery. There was no overlap with results published by Lowes et al. (*N Engl J Med* 2002 May 2; 346(18):1357-65; Lowes B D, et al. *J Heart Lung Transplant* 2006 May; 25(5):579-88), who investigated genes overexpressed during recovery from HF. This may indicate that there are important differences between gene expression changes caused by therapy and characteristics of gene expression which may predict clinical outcome.

Several technical features of this study warrant mention. While most previous studies have used cardiac tissues obtained at advanced stages of cardiomyopathy (often at transplantation), we investigated biopsies from patients obtained at first presentation with heart failure. Therefore, the obtained biomarkers are very relevant for a possible clinical application and suggest initial pathologic changes in the transcriptome, which may be causative for the disease and possible therapeutic targets. Additionally, we used a highly efficient RNA processing technique, allowing microarray analysis without additional amplification, and thus avoiding possible bias due to different binding preferences of primers and reduction of time and costs with regards to a later clinical application.

Although endomyocardial biopsy is a low risk procedure, alternative methods for obtaining transcriptomic biomarkers can be developed. There has been evidence that affected tissue and circulating blood cells share a high percentage of common genes. Easy accessibility of PBMCs by a simple venous puncture makes those cells very attractive for a clinical application.

In summary, we have developed a novel transcriptomic biomarker for prognosis in heart failure obtainable from a single endomyocardial biopsy with potential for a direct clinical application. This approach should improve individualization of cardiac care and help identify patients at highest risk for circulatory collapse within the first years of presentation with heart failure. The involvement of genes in neuromuscular development, angiogenesis and DNA repair mechanism including telomerase activity within the TBB for patients with excellent clinical outcome offers biological plausibility regarding an advantage in recovery.

Example 2: Transcriptomic Biomarker for Predicting Clinical Outcome and Prognosis in Heart Failure Using a Transcriptomic Biomarker To identify this biomarker (gene signature) heart samples were collected from patients undergoing heart biopsy early in their clinical course. Following this the samples were stored in a biorepository for 5-10 years during which time the outcome of patients were determined.

Endomyocardial biopsy samples from patients with idiopathic cardiomyopathy have been collected at the Johns Hopkins Hospital between 1997-2004 and stored in liquid nitrogen. Biopsy samples from patients with idiopathic cardiomyopathy were chosen from this biorepsitory—18 patients with good prognosis and 12 patients with bad prognosis. Bad prognosis was defined as occurrence of death or an intervention, namely left-ventricular assist device placement or cardiac transplant, in the first 2 years after diagnosis, while good prognosis was defined as event free survival for greater than 5 years after diagnosis. The MIAME (Minimum information about a microarray experiment) guidelines were followed for all experiments. The tissue was homogenized with the MM301 instrument from Retsch and total RNA was isolated with the Micro-to-Midi Total RNA purification system from Invitrogen. Microarray analysis of total RNA was performed with the Human Genome U133 Plus 2.0 Array from Affymetrix. In all samples, both RNA isolation and microarray hybridization met all indices of quality control as specified in the Affymetrix Guideline for Assessing Sample and Array Quality.

Figure 6:
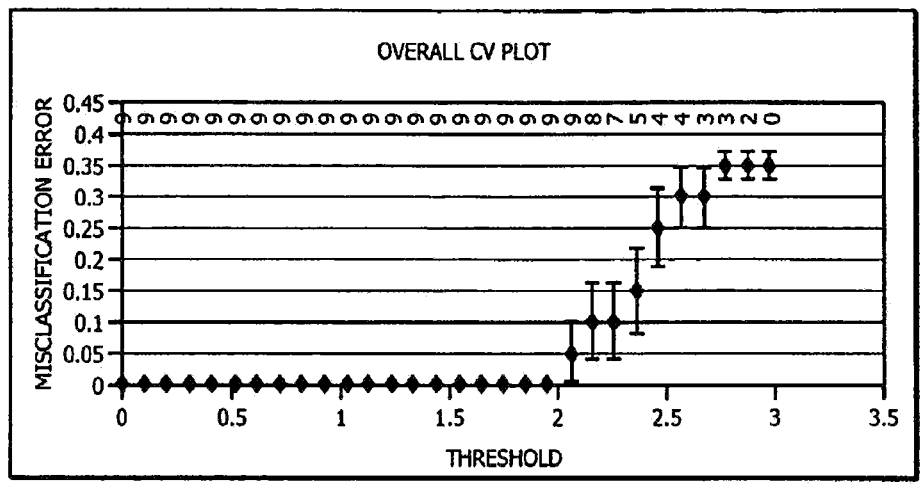
FIG. 6 is a graph showing the crossvalidation of the training set: starting from a set of 9 genes, increasing the threshold leads to a constant increase of the misclassification error after a limit of 2.1
Figure 7:
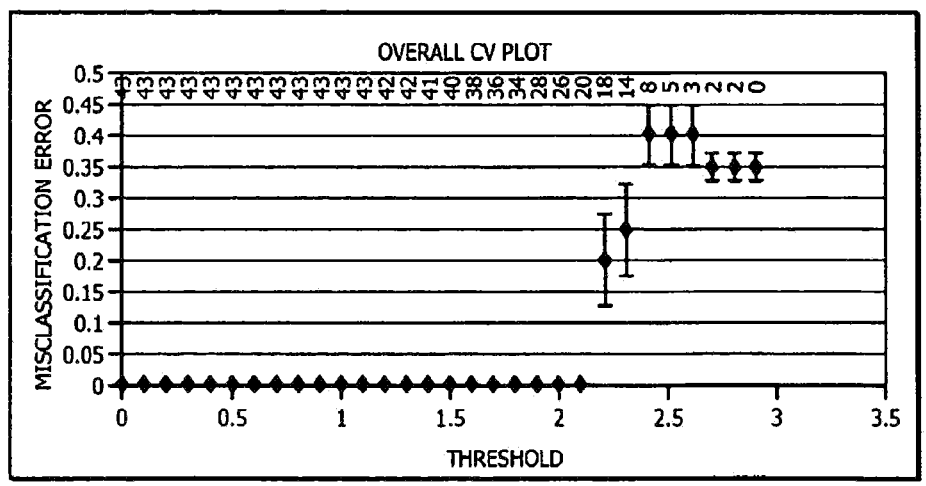
FIG. 7 is a graph showing crossvalidation of the training set: Increasing the threshold constantly increases the misclassification error after a limit of 2.1
Figure 8:
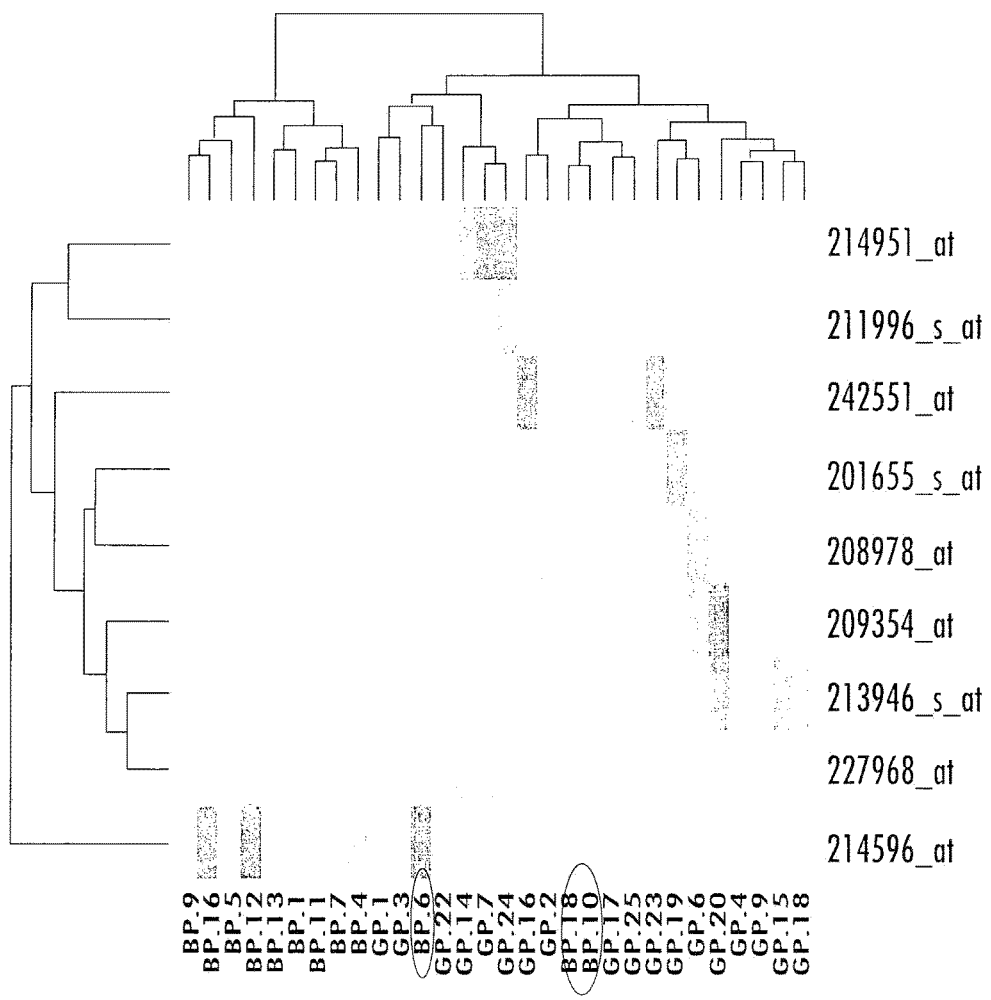
FIG. 8 is a heatmap using 9 genes signature: this heatmap was created by an unsupervised clustering approach using standardization by mean levels of expression. Each column represents a sample and each line corresponds to a gene, for which the IDs from affymetrix are listed on the right side. For further details about the gene annotations see table 5. A red color means low expression of the gene, whereas a blue color demonstrates high gene expression levels. Three samples from patients with bad prognosis were grouped wrong (encircled).
Figure 9:
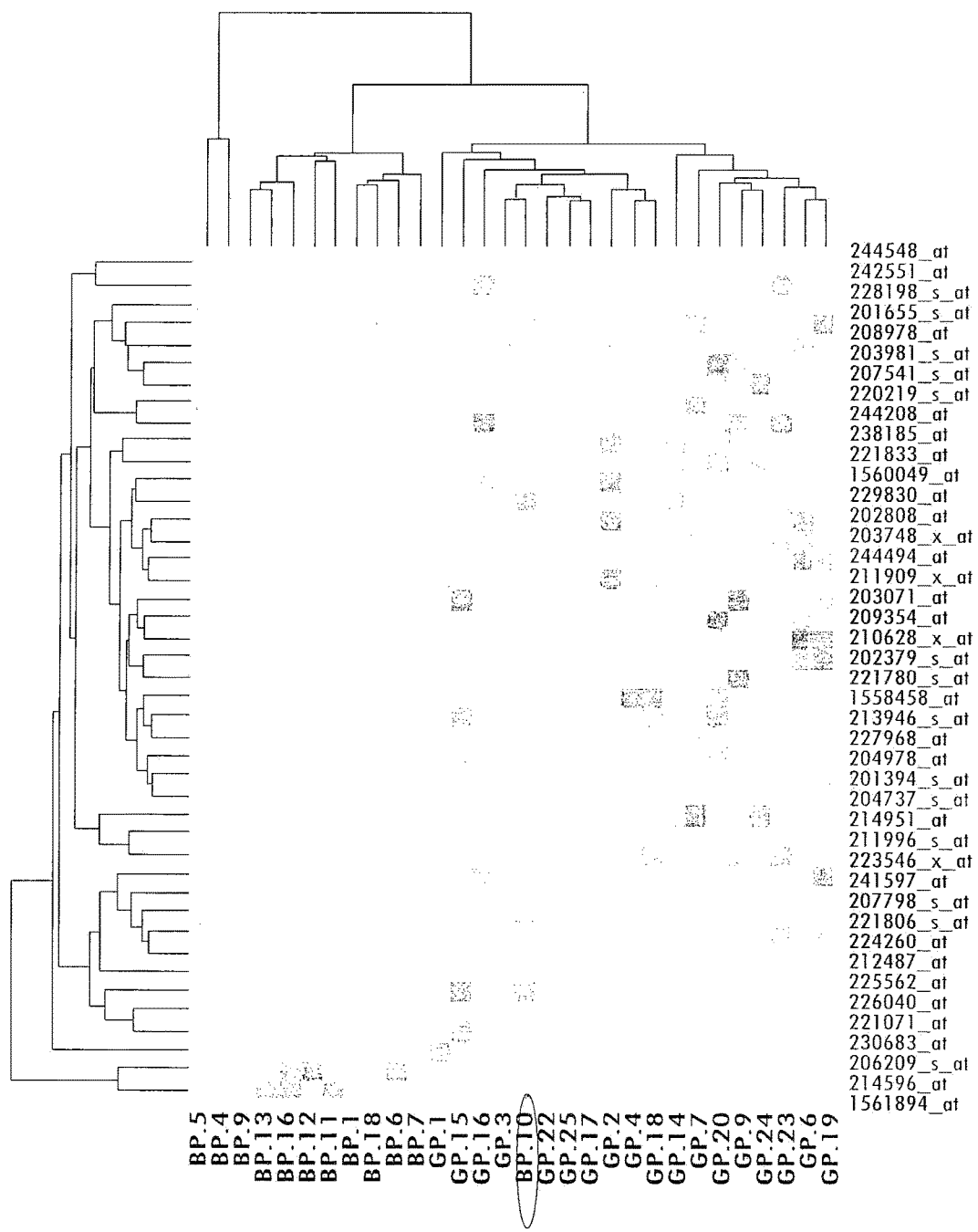
FIG. 9 shows a heatmap using 43 genes signature: this heatmap was created with the same unsupervised hierarchical clustering algorithm. Only one sample was classified wrong (BP-10). The history of this patient, it was later found out, was that he was first diagnosed with heart failure more than 5 years before he died, which suggests that he was actually a long term survivor and recognized correctly by our algorithm. In this study, he was categorized as a patient with poor prognosis, because the biopsy was obtained one year before he died.
Figure 10:
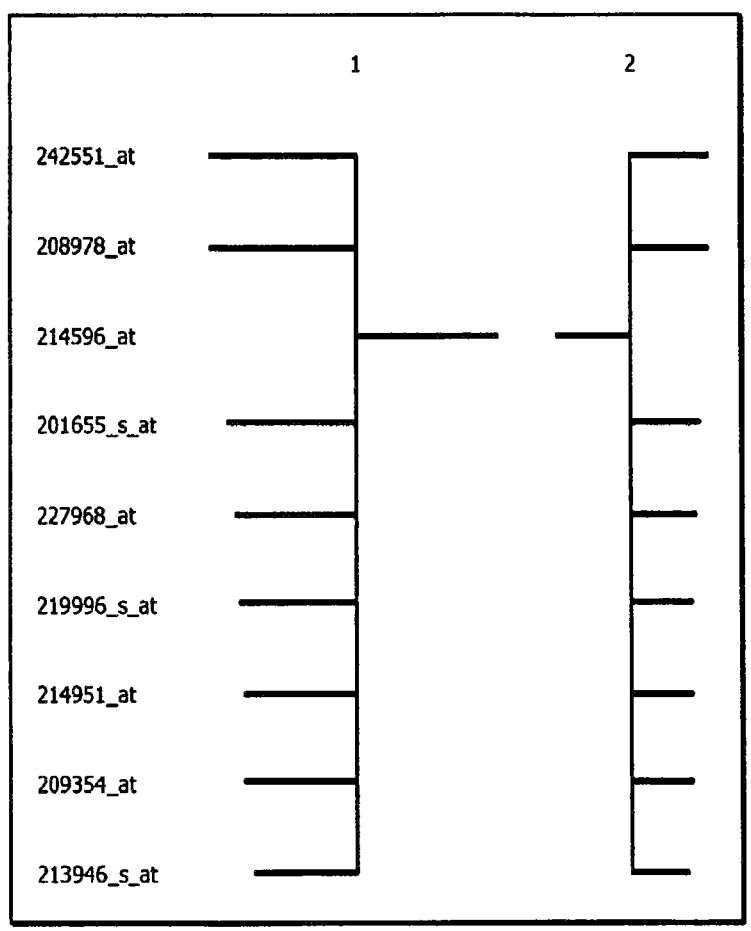
FIG. 10 is a graph showing the nearest shrunken centroid of the "9 genes classifier": The centroids were calculated in PAM from the average expression for each gene in each class divided by the within-class standard deviation for that gene. The nearest shrunken centroid classification "shrinks" each of the class centroids toward the overall centroid for all classes by the threshold. Nearest centroid classification takes the gene expression profile of a new sample, and compares it to each of these class centroids. The class whose centroid that it is closest to, in squared distance, is the predicted class for that new sample. Each line in the graph represents a gene. The red centroid characterizes group 1 (bad prognosis), the green centroid characterizes group 2 (good prognosis). All genes, except one, that were upregulated in the group with good prognosis were underexpressed in the group with poor clinical outcome.
Figure 11:
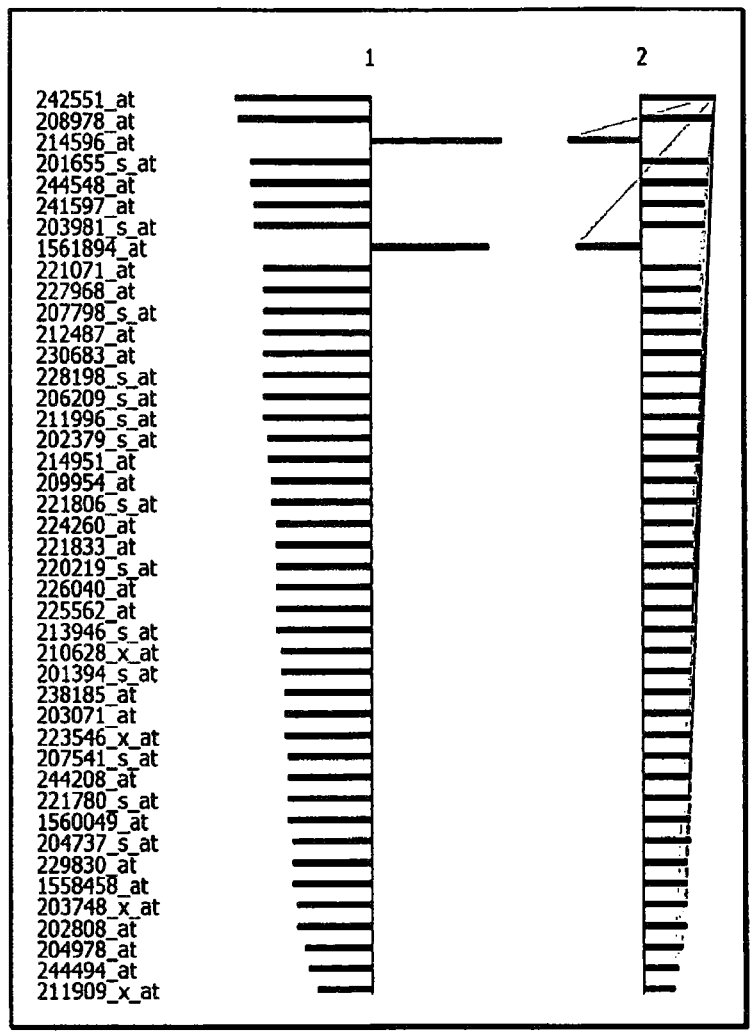
FIG. 11 shows the nearest shrunken centroid of the "43 genes classifier": After extending our classifier to 43 genes, a second upregulated gene appeared in the group with poor prognosis.

Raw expression values of all microarray chips were preprocessed with Robust Multiarray Average (RMA) in R. In order to find a transcriptomic biomarker for class prediction of either bad or good prognosis, Prediction Analysis of Microarrays (PAM) implemented in R was used. PAM uses the "nearest shrunken centroid" method for class prediction. After training of the classifier (supervised clustering) in a subset of 13 samples of patients with good prognosis and 7 samples of patients with bad prognosis, a cluster of 9 genes that predicted clinical outcome with 60% sensitivity and 100% specificity (FIG. 6, FIG. 10, Table 3, Table 5) was found. The same 9 genes were used to produce a heatmap (unsupervised clustering), standardized by mean levels of expression (FIG. 8). Each row represented one of the 9 genes, and each column was a patient sample. A red cell depicts an underexpressed gene in a given patient relative to the average gene expression in all patients, while a blue cell denotes an overexpressed gene. The dendrogram at the top is an unsupervised hierarchical clustering algorithm that divides samples into groups based on the similarity of the gene expression profiles. The "good prognosis samples" and the "poor prognosis samples" segregate into two dominant clusters. However, 3 samples were misclassified with this approach (sensitivity 75%, specificity 100%). In all cases the misclassifications were bad prognosis patients being misclassified as good prognosis. The number of genes were increased to 43, in order to minimize misclassification error (FIG. 6, FIG. 7) and developed a classifier in PAM on the same training set (n=20), which predicted again with 60% sensitivity and 100% specificity. However, the individual probabilities for correct class prediction ameliorated slightly, as denoted in Table 5. With a heatmap including those 43 genes, a higher accuracy than with PAM was achieved, misclassifying only one sample in 30 total (92% sensitivity and 100% specificity). One sample (BP-10) was misclassified in all approaches, presumably an outlier (FIG. 9). The fact that the discovered set of genes performed very accurately on all samples, strengthens the results of the biomarker signature. Of all genes contributing to the 9 genes transcriptomic biomarker, only one was significantly upregulated in the group with bad prognosis. The set of 43 genes contained one additional upregulated unidentified transcript in the group with bad prognosis (FIG. 11). Tables 6 and 7 list all genes comprised within the 9 and 43 genes signature and that were overexpressed in the group of patients with long term survival. The 43 gene biomarker contained genes that are of prognostic relevance, as for example Myosin heavy polypeptide 7. Its mutations have been shown to be associated with severity of heart failure, in particular in familial dilated cardiomyopathy. The outliers can be reduced by training the classifier on a higher number of investigated samples. The presented biomarker achieved significantly higher prognostic accuracy than classic risk factors and schemes that have been suggested by other groups, e.g. Seattle Heart Failure Index.

TABLE 3

| Prediction for Threshold = 0 Settings Name: Settings4 | | | | | | | | | | |
|---|---|---|---|---|---|---|---|---|---|---|
| Offset Quantile | | | 50 both | | Offset Value RNG Seed | | | | 0.3 420 | |
| Prior Distribution (Sample Prior) | | | | | | | | | | |
| Class Prob. | | | 1 0.35 | | | | 2 0.65 | | | |
| Test set Prediction Confusion Matrix | | | | | | | | | | |
| True\Predicted 1 2 | | | 1 3 0 | | | | 2 2 5 | | | |
| Actual, Predicted Classes and Predicted Posterior Probabilities | | | | | | | | | | |
| Sample Labels | BP-10 | BP-18 | BP-6 | BP-7 | BP-9 | GP-20 | GP-22 | GP-23 | GP-24 | GP-25 |
| Class Labels | 1 | 1 | 1 | 1 | 1 | 2 | 2 | 2 | 2 | 2 |
| Predicted | 2 | 2 | 1 | 1 | 1 | 2 | 2 | 2 | 2 | 2 |
| Bad prognosis | 0.00842577 | 0.08808878 | 0.806138 | 0.73512 | 0.999652 | 0.000469 | 0.098695 | 0.0002 | 0.000244 | 0.00194 |
| Good prognosis | 0.99157422 | 0.91191122 | 0.193861 | 0.26488 | 0.000348 | 0.999531 | 0.901305 | 0.9998 | 0.999756 | 0.99805 |

Prediction Result of the Test Set (n=10):

9 genes signature was used (Table 3). The sample labels are listed in the fifth row from below, followed by the actual class labels and the predicted classes. Bad prognosis (BP) samples were assigned to class 1-good prognosis (GP) samples were assigned to class 2. 8 samples were correctly classified (probabilities between 73 and 99%). Only two samples were misclassified (with a probability higher than 90%). Predicted probabilities are listed for each class in the last two lines.

TABLE 4

Prediction for Threshold = 0
Settings Name: Settings5

| Offset Quantile | 50 | Offset Value | 0.350764 |
|---|---|---|---|
| | both | RNG Seed | 420473 |

Prior Distribution (Sample Prior)

| Class | 1 | 2 |
|---|---|---|
| Prob. | 0.35 | 0.65 |

Test set Prediction Confusion Matrix (Threshold = 0)

| True\Predicted | 1 | 2 |
|---|---|---|
| 1 | 3 | 2 |
| 2 | 0 | 5 |

Actual, Predicted Classes and Predicted Posterior Probabilities

| Sample Labels | BP-18 | BP-10 | BP-6 | BP-7 | BP-9 | GP-20 | GP-22 | GP-23 | GP-24 | GP-25 |
|---|---|---|---|---|---|---|---|---|---|---|
| Class Labels | 1 | 1 | 1 | 1 | 1 | 2 | 2 | 2 | 2 | 2 |
| Predicted Class Labels | 2 | 2 | 1 | 1 | 1 | 2 | 2 | 2 | 2 | 2 |
| Bad prognosis | 0.011971912 | 1.92842E-06 | 0.995824315 | 0.896715 | 1 | 2.3E-13 | 1.47E-05 | 2.74E-13 | 1.48E-12 | 3.69E-08 |
| Good prognosis | 0.988028088 | 0.999998072 | 0.004175685 | 0.103285 | 4.51E-08 | 1 | 0.999985 | 1 | 1 | 1 |

Prediction Result of the Test Set (n=10):
43 genes signature (Table 4). Description of the table is the same as in table 6. The probabilities for the right classification increased slightly.

TABLE 5

| Sample Labels | BP-10 | BP-18 | BP-6 | BP-7 | BP-9 | GP-20 | GP-22 | GP-23 | GP-24 | GP-25 |
|---|---|---|---|---|---|---|---|---|---|---|
| 9 genes signature | | | | | | | | | | |
| Bad prognosis | 0.008425774 | 0.08808878 | 0.806138017 | 0.73512 | 0.999652 | 0.000469 | 0.098695 | 0.0002 | 0.000244 | 0.001943 |
| Good prognosis | 0.991574226 | 0.91191122 | 0.193861983 | 0.26488 | 0.000348 | 0.999531 | 0.901305 | 0.9998 | 0.999756 | 0.998057 |
| 43 genes signature | | | | | | | | | | |
| Bad prognosis | 0.011971912 | 1.92842E-06 | 0.995824315 | 0.896715 | 1 | 2.3E-13 | 1.47E-05 | 2.74E-3 | 1.48E-12 | 3.69E-08 |
| Good prognosis | 0.988028088 | 0.999998072 | 0.004175685 | 0.103285 | 4.51E-08 | 1 | 0.999985 | 1 | 1 | 1 |

Table 5 shows the results from PAM: performance of both 9 genes signature and 43 genes signature. Each sample labeled BP was derived from a patient with bad prognosis, each sample labeled with GP from a patient with good prognosis. The predicted probability for each class using the developed classifier is listed in each row. Probabilities for correct classification increased slightly with increasing the number of genes.

TABLE 6

| Method used | Sensitivity | Specificity |
|---|---|---|
| PAM: 9 genes | 60% | 100% |
| PAM: 43 genes | 60% | 100% |

TABLE 6-continued

| Method used | Sensitivity | Specificity |
|---|---|---|
| Heatmap: 9 genes | 75% | 100% |
| Heatmap: 43 genes | 92% | 100% |

Table 6 is an overview of performance of all applied algorithms. Every method used was able to predict poor prognostic outcome with 100% specificity. However, unsupervised clustering (heatmap) predicted with higher sensitivity in general and performed better, especially when increasing the number of genes in the molecular signature from 9 to 43 genes.

TABLE 7

| Probe | Gene Title | Gene Symbol | GO Biological Process Description |
|---|---|---|---|
| 201655 | heparan sulfate proteoglycan 2 (perlecan) | HSPG2 | cell adhesion, protein localization |
| 208978 | cysteine-rich protein 2 | CRIP2 | — |
| 209354 | tumor necrosis factor receptor superfamily, member 14 | TNFRSF14 | apoptosis, immune response, cell surface receptor linked signal |
| 211996 | KIAA0220-like protein, nuclear pore complex | LOC23117 | biological_process |
| 213946 | obscurin-like 1, similar to titin isoform N2-B | OBSL1 | — |
| 214951 | solute carrier family 26, member 10 | SLC26A10 | transport, regulation of Rho protein signal transduction |
| 227968 | Parkinson disease 7 domain containing 1 | PDDC1 | — |
| 241597 | Arginine-glutamic acid dipeptide (RE) repeats | RERE | chromatin remodeling, transcription, NLS-bearing substrate import |
| 242551 | Chromosome 18 open reading frame 1 | C18orf1 | biological_process |

Table 7 shows 8 upregulated genes in patients with good prognosis: first column contains the IDs from Affymetrix for all upregulated transcripts of the 9 genes biomarker. Only 1 gene was downregulated, namely the muscarinic acetylcholine receptor M3. Annotations for biological function were obtained from the Gene Ontology website (GO).

TABLE 8

| Probe | Gene Title | Gene Symbol | GO Biological Process Description |
|---|---|---|---|
| 155845 | Hypothetical LOC401320 | LOC401320 | — |
| 156004 | CUG triplet repeat, RNA binding protein 2 | CUGBP2 | RNA processing, neuromuscular junction development, regulation of |
| 201394 | RNA binding motif protein 5 | RBM5 | RNA processing, cell cycle, negative regulation of progression |
| 201655 | heparan sulfate proteoglycan 2 (perlecan) | HSPG2 | cell adhesion, protein localization |
| 202379 | natural killer-tumor recognition sequence | NKTR | protein folding |
| 202808 | — | — | — |
| 203071 | sema domain, immunoglobulin domain (Ig), short basic | SEMA3B | cell-cell signaling, development, axon guidance |
| 203748 | RNA binding motif, single stranded interacting protein 1 | RBMS1 | DNA replication, RNA processing, regulation of translation |
| 203981 | ATP-binding cassette, sub-family D (ALD), member 4 | ABCD4 | transport |
| 204737 | myosin, heavy chain 6, myosin, heavy chain 7 | MYH6 /// MYH7 | striated muscle contraction, muscle contraction |
| 204978 | splicing factor, arginine/serine-rich 16 | SFRS16 | mRNA processing, RNA splicing |
| 206209 | carbonic anhydrase IV | CA4 | one-carbon compound metabolism, visual perception, response to |
| 207541 | exosome component 10 | EXOSC10 | mRNA catabolism, nonsense-mediated decay, rRNA processing |
| 207798 | ataxin 2-like | ATXN2L | biological_process |
| 208978 | cysteine-rich protein 2 | CRIP2 | — |
| 209354 | tumor necrosis factor receptor superfamily, member 14 | TNFRSF14 | apoptosis, immune response, cell surface receptor linked signal |
| 210628 | latent transforming growth factor beta binding protein 4 | LTBP4 | regulation of cell growth, protein folding, development, regulation of |
| 211909 | prostaglandin E receptor 3 (subtype EP3) | PTGER3 | transcription, DNA-dependent, signal transduction, G-protein coupled |
| 211996 | KIAA0220-like protein, nuclear pore complex | LOC23117 | biological_process |
| 212487 | G patch domain containing 8 | GPATCH8 | biological_process |
| 213946 | obscurin-like 1, similar to titin isoform N2-B | OBSL1 | — |
| 214951 | solute carrier family 26, member 10 | SLC26A10 | transport, regulation of Rho protein signal transduction |
| 220219 | leucine rich repeat containing 37A | LRRC37A | — |
| 221071 | — | — | — |
| 221780 | DEAD (Asp-Glu-Ala-Asp) box polypeptide 27 | DDX27 | — |
| 221806 | SET domain containing 5 | SETD5 | — |
| 221833 | Lon peptidase 2, peroxisomal | LONP2 | proteolysis, ATP-dependent proteolysis |
| 223546 | LUC7-like (S. cerevisiae) | LUC7L | negative regulation of striated muscle development |
| 224260 | CDNA clone IMAGE: 4478733 | — | — |

TABLE 8-continued

| Probe | Gene Title | Gene Symbol | GO Biological Process Description |
|---|---|---|---|
| 225562 | RAS p21 protein activator 3 | RASA3 | intracellular signaling cascade, regulation of small GTPase mediated |
| 226040 | MRNA; cDNA DKFZp762N156 (from clone | — | — |
| 227968 | Parkinson disease 7 domain containing 1 | PDDC1 | — |
| 228198 | Mitochondrial ribosomal protein S9 | MRPS9 | protein biosynthesis, DNA damage response, detection of DNA |
| 229830 | Transcribed locus | — | — |
| 230683 | CDNA: FLJ20892 fis, clone ADKA03430 | — | — |
| 238185 | RNA binding motif, single stranded interacting protein 1 | RBMS1 | DNA replication, RNA processing /// regulation of translation |
| 241597 | Arginine-glutamic acid dipeptide (RE) repeats | RERE | chromatin remodeling, transcription, NLS-bearing substrate import into |
| 242551 | Chromosome 18 open reading frame 1 | C18orf1 | biological_process |
| 244208 | Checkpoint suppressor 1 | CHES1 | DNA damage checkpoint, G2 phase of mitotic cell cycle |
| 244494 | Zinc finger, DHHC-type containing 1 | ZDHHC1 | biological_process, protein palmitoylation |
| 244548 | Rho GTPase activating protein 26 | ARHGAP26 | signal transduction, nervous system development, actin cytoskeleton |

Table 8: 41 upregulated genes in patients with good prognosis: 41 transcripts of the 43 genes biomarker were overexpressed in the group with good clinical outcome. Only 2 genes were downregulated—again the muscarinic acetylcholine receptor M3, as in the 9 genes molecular signature, and a transcript with unknown function.

Although the invention has been illustrated and described with respect to one or more implementations, equivalent alterations and modifications will occur to others skilled in the art upon the reading and understanding of this specification and the annexed drawings. In addition, while a particular feature of the invention may have been disclosed with respect to only one of several implementations, such feature may be combined with one or more other features of the other implementations as may be desired and advantageous for any given or particular application.

The Abstract of the disclosure will allow the reader to quickly ascertain the nature of the technical disclosure. It is submitted with the understanding that it will not be used to interpret or limit the scope or meaning of the following claims.

What is claimed is:

1. A method of identifying and treating a patient with heart failure with good prognosis comprising:
   obtaining an endomyocardial biopsy sample from the patient with heart failure;
   measuring the expression of a set of genes in the sample by PCR,
   wherein the set of genes consists of HSPG2, CRIP2, TNFRSF14, LOC23117, OBSL1, SLC26A10, PDDC1, RERE, C18orf1, LOC401320, CUGBP2, RBM5, NKTR, SEMA3B, RBMS1, ABCD4, MYH6, MYH7, SFRS16, CA4, EXOSC10, ATXN2L, LTBP4, PTGER3, GPATCH8, LRRC37A, DDX27, SETD5, LONP2, LUC7L, RASA3, MRPS9, RBMS1, CHES1, ZDHHC1, and ARHGAP26,
   wherein the patient is identified as having a good prognosis for recovery when the expression of the set of genes is increased at least 1.2 times as compared to a normal control; and
   treating the identified patient with a good prognosis with a diuretic, ACE inhibitor, aldosterone antagonist, 6-Antogonist, or ionotropic therapy.

2. The method of claim 1, wherein the expression of the set of genes is measured on a chip.

3. The method of claim 1, wherein the PCR is RT-PCR.

* * * * *

UNITED STATES PATENT AND TRADEMARK OFFICE
CERTIFICATE OF CORRECTION

| | | |
|---|---|---|
| PATENT NO. | : 10,131,948 B2 | Page 1 of 1 |
| APPLICATION NO. | : 14/334024 | |
| DATED | : November 20, 2018 | |
| INVENTOR(S) | : Joshua M. Hare et al. | |

It is certified that error appears in the above-identified patent and that said Letters Patent is hereby corrected as shown below:

In the Specification

At Column 1, Line 23 the paragraph under STATEMENT REGARDING FEDERALLY SPONSORED RESEARCH, which states:
This invention was made with U.S. government support under grant numbers M400-217-2954 and RO-1 HL-65455 both awarded by the National Institutes of Health. The U.S. government may have certain rights in the invention.

Should be replaced with the following paragraph:
--This invention was made with government support under grant number HL065455 awarded by the National Institutes of Health. The government has certain rights in the invention.--

Signed and Sealed this
Fifth Day of May, 2020

Andrei Iancu
*Director of the United States Patent and Trademark Office*